US012247212B2

United States Patent
De Graag et al.

(10) Patent No.: US 12,247,212 B2
(45) Date of Patent: Mar. 11, 2025

(54) CYSDV RESISTANCE IN MEMBERS OF THE CUCURBITACEAE FAMILY

(71) Applicant: RIJK ZWAAN ZAADTEELT EN ZAADHANDEL B.V., De Lier (NL)

(72) Inventors: Paul De Graag, De Lier (NL); Lena Johanna Huijbregts-Doorduin, De Lier (NL); Raoul Jacobus Johannes Maria Frijters, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 717 days.

(21) Appl. No.: 17/158,275

(22) Filed: Jan. 26, 2021

(65) Prior Publication Data

US 2021/0222190 A1    Jul. 22, 2021

Related U.S. Application Data

(63) Continuation-in-part of application No. PCT/EP2019/070534, filed on Jul. 30, 2019.

(51) Int. Cl.
| | | |
|---|---|---|
| C12N 15/82 | (2006.01) | |
| A01H 1/04 | (2006.01) | |
| A01H 5/08 | (2018.01) | |
| C12Q 1/6895 | (2018.01) | |
| C07K 14/415 | (2006.01) | |

(52) U.S. Cl.
CPC ......... *C12N 15/8283* (2013.01); *A01H 1/045* (2021.01); *A01H 5/08* (2013.01); *C12Q 1/6895* (2013.01); *C07K 14/415* (2013.01); *C12Q 2600/13* (2013.01); *C12Q 2600/158* (2013.01)

(58) Field of Classification Search
None
See application file for complete search history.

(56) References Cited

FOREIGN PATENT DOCUMENTS

| EP | 1800535 A1 | 6/2007 |
|---|---|---|
| EP | 3005862 A1 | 4/2016 |
| WO | 02/22836 A2 | 3/2002 |
| WO | 2010/071431 A1 | 6/2010 |

OTHER PUBLICATIONS

PARIS (2015 Annals of Botany 116:133-148 "Origin and emergence of the sweet dessert watermelon, Citrullus lanatus"). (Year: 2015).*
Database NCBI Accession No. XM 008453007: PREDICTED: Cucumis melo putalive clathrin assembly protein At5g57200 (LOC103492585), partial mRNA (Jun. 7, 2016).
International Search Report and Written Opinion issued Oct. 24, 2019 in Int'l Application No. PCT/EP2019/070534.

* cited by examiner

*Primary Examiner* — Matthew R Keogh
*Assistant Examiner* — Rebecca Stephens
(74) *Attorney, Agent, or Firm* — Duane Morris LLP; Thomas J. Kowalski

(57) ABSTRACT

The present invention relates to a modified gene that provides resistance to Cucurbit Yellow Stunting Disorder virus (CYSDV) when present in a plant of the Cucurbitaceae family. The invention further relates to progeny, seed, and fruit of the plant that is resistant against CYSDV. The invention also relates to propagation material suitable for producing the plant that is resistant to CYSDV. Additionally, the invention relates to methods for producing, identifying, and selecting a plant of the Cucurbitaceae family having resistance against CYSDV.

11 Claims, 7 Drawing Sheets

Specification includes a Sequence Listing.

FIG. 1

InterPro
Protein sequence analysis & classification

Home | Search | Release notes | Download | About | Help | Contact

Overview
Similar proteins
Structures

Filter view on

Entry type
- ☑ [H] Homologous superfamily
- ☑ [F] Family
- ☑ [D] Domain
- ☑ [R] Repeats
- ☑ [S] Site Status
- ☑ [?] Unintegrated Per-residue features
- ☑ Residue annotation Colour by
domain relationship
source database

Submitted sequence           [Export ⬇]

Length 592 amino acids

Protein family membership
None predicted

Homologous superfamilies

▷Homologous superfamily
1   100   200   300   400   500   592

Domains and repeats

▷Domain
▷Domain
1   100   200   300   400   500   592

Detailed signature matches

[H] PR008942  ENTH/VHS
▷SSF48464(ENTH/VHS..)
▷G3DSA:1.25.40.90

[H] PR014712  Phosphoinositide-binding clathrin adaptor, domain 2
▷G3DSA:1.20.58..

[D] PR013809  ENTH domain
▷PS50942(ENTH)
▷SM00273(enth_2)

[D] PR011417  AP180 N-terminal homology (ANTH) domain
▷PF07651(ANTH)

[?] no IPR  Unintegrated signatures
▷Coil
▷PTHR22951(CLATHRIN..)
▷PTHR22951:SF56 (SUB..)
▷SSF89009(GAT-like..)
▷cd03564(ANTH_AP180..)
▷mobidb-lite(disord..)

Residue annotation

▷PtdIns(4,5)P2-bind..

SEQUENCE LISTING

```
<160> NUMBER OF SEQ ID NOS: 15

<210> SEQ ID NO 1
<211> LENGTH: 1779
<212> TYPE: DNA
<213> ORGANISM: Cucumis melo
<220> FEATURE:
<223> OTHER INFORMATION: CLARP1

<400> SEQUENCE: 1
atgggcacat ttcagagctt ccgcaaagct tatggcgctc tcaaagattc caccaaggtc      60
ggcctcgcta aggtcaacag cgaattcaag gatttggata tcgccatcgt taaggctacc     120
aatcacgttg aatgtccgcc taaagaacgt catgttcgaa aaattttttc ggctacgtcc     180
gttgtgagac ctcgggcaga tgtggcgtat tgtattcatg cattggcgaa gagattgtcg     240
aagacgcgga attggatcgt tgccttgaag acgttgatag ttgtacatag gacattgaga     300
gagggagatc ccaccttcag ggaagaactt cttaattatt cacacagagg acatattctc     360
caaatatcca attttaagga tgattcgagt cctcttgctt gggattgttc tgcttgggta     420
aggacatatg ccctttttct agaagagaga cttgaatgtt atagaatctt gaagtatgat     480
attgaatcgg aacgtctaac gaaaacatca cctggatcga cgaaggtcca tagtaggaca     540
cgattgctga actctgatga gctactggag cagctacccg cattgcagca acttctctac     600
cgccttatgg gatgtcagcc agaaggagga gcttacagca actatcttat ccagtatgcc     660
ctggctttgg tactcaaaga gagctttaaa atatattgtg cgataaatga tggaataata     720
aatcttgtgg acatgttctt tgatatgcca aggcatgatg cagttaaagc tctcaatata     780
tacaaaagag caagcaacca ggctgaaaat cttgcggatt tttacgaata ctgtaaggga     840
ttggaacttg ctagaacttt tcagtttccc actttgaagc agccacctcc atcatttctt     900
tcaacaatgg aggagtatat aagagaagca ccacagactg ttctgttaa taagagactg     960 gaataccgag agacagagct attgacacag gaagaggata gcccgaaga atcagccgaa    1020 attgaaaagg aggttgaaaa tgttgaggac aacaaaccac tggttgaaac agaggaagaa    1080
ccccaacaga aggaagagga ggttgctgaa cctccacctc taatagaaac ccacgaccca    1140
agtgatcttc tgggtctgaa tgaaataaat cccaaagctg cagaaataga agaaagcaat    1200
gctttagctc ttgctattgt tacaaatggg aatgacccat cttcttcaaa tcgtgcattg    1260
agtgaaattg gcggtagtgg ttgggagcta gcgcttgtta ccacaccaag caataatact    1320
ggtccttctg tcgaaggcag actggccggg ggctttgaca agctattgct tgatagcttg    1380
```

-continued

```
tatgaagatg aacatgccag aagacatctt cagcttcaga atgctggata tggaccatac    1440
ggggaaatga tggtacagaa tccattcgaa cagcatgacc cgttttcatt gtcgagcaac    1500
atagcgcctc ctccgaacgt gcaaatggca atgatggctc aacaacaaca aatgcttttc    1560
caacaccaac aacaaccatt acaaagcaat accttccctc agcaacaaca gcagttacat    1620
tcaaatgact caatgatgat ggttccttat caacaacagt tgcctcaata cccacaacaa    1680
caaatgcaac aaattggtcc ttctaatcca tttggtgacc ttttcttttc ctttcctcaa    1740
acttcagtac ccccaggagg acatcataat ctaatctag                           1779
```

<210> SEQ ID NO 2
<211> LENGTH: 592
<212> TYPE: PRT
<213> ORGANISM: Cucumis melo
<220> FEATURE:
<223> OTHER INFORMATION: CLARP1

<400> SEQUENCE: 2

```
Met Gly Thr Phe Gln Ser Phe Arg Lys Ala Tyr Gly Ala Leu Lys Asp
 1               5                  10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Ser Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser His Arg Gly His Ile Leu Gln Ile Ser Asn Phe Lys Asp Asp
        115                 120                 125

Ser Ser Pro Leu Ala Trp Asp Cys Ser Ala Trp Val Arg Thr Tyr Ala
    130                 135                 140

Leu Phe Leu Glu Glu Arg Leu Glu Cys Tyr Arg Ile Leu Lys Tyr Asp
145                 150                 155                 160

Ile Glu Ser Glu Arg Leu Thr Lys Thr Ser Pro Gly Ser Thr Lys Val
                165                 170                 175

His Ser Arg Thr Arg Leu Leu Asn Ser Asp Glu Leu Leu Glu Gln Leu
            180                 185                 190

Pro Ala Leu Gln Gln Leu Leu Tyr Arg Leu Met Gly Cys Gln Pro Glu
        195                 200                 205

Gly Gly Ala Tyr Ser Asn Tyr Leu Ile Gln Tyr Ala Leu Ala Leu Val
    210                 215                 220

Leu Lys Glu Ser Phe Lys Ile Tyr Cys Ala Ile Asn Asp Gly Ile Ile
225                 230                 235                 240

Asn Leu Val Asp Met Phe Phe Asp Met Pro Arg His Asp Ala Val Lys
                245                 250                 255

Ala Leu Asn Ile Tyr Lys Arg Ala Ser Asn Gln Ala Glu Asn Leu Ala
            260                 265                 270

Asp Phe Tyr Glu Tyr Cys Lys Gly Leu Glu Leu Ala Arg Thr Phe Gln
        275                 280                 285

Phe Pro Thr Leu Lys Gln Pro Pro Pro Ser Phe Leu Ser Thr Met Glu
```

```
                290                 295                 300
Glu Tyr Ile Arg Glu Ala Pro Gln Thr Gly Ser Val Asn Lys Arg Leu
305                 310                 315                 320
Glu Tyr Arg Glu Thr Glu Leu Leu Thr Gln Glu Asp Lys Pro Glu
            325                 330                 335
Glu Ser Ala Glu Ile Glu Lys Glu Val Glu Asn Val Glu Asp Asn Lys
            340                 345                 350
Pro Leu Val Glu Thr Glu Glu Pro Gln Gln Lys Glu Glu Val
            355                 360                 365
Ala Glu Pro Pro Leu Ile Glu Thr His Asp Pro Ser Asp Leu Leu
370                 375                 380
Gly Leu Asn Glu Ile Asn Pro Lys Ala Ala Glu Ile Glu Ser Asn
385                 390                 395                 400
Ala Leu Ala Leu Ala Ile Val Thr Asn Gly Asn Asp Pro Ser Ser Ser
            405                 410                 415
Asn Arg Ala Leu Ser Glu Ile Gly Gly Ser Gly Trp Glu Leu Ala Leu
            420                 425                 430
Val Thr Thr Pro Ser Asn Asn Thr Gly Pro Ser Val Glu Gly Arg Leu
            435                 440                 445
Ala Gly Gly Phe Asp Lys Leu Leu Leu Asp Ser Leu Tyr Glu Asp Glu
            450                 455                 460
His Ala Arg Arg His Leu Gln Leu Gln Asn Ala Gly Tyr Gly Pro Tyr
465                 470                 475                 480
Gly Glu Met Met Val Gln Asn Pro Phe Glu Gln His Asp Pro Phe Ser
                485                 490                 495
Leu Ser Ser Asn Ile Ala Pro Pro Asn Val Gln Met Ala Met Met
                500                 505                 510
Ala Gln Gln Gln Gln Met Leu Phe Gln His Gln Gln Pro Leu Gln
            515                 520                 525
Ser Asn Thr Phe Pro Gln Gln Gln Gln Leu His Ser Asn Asp Ser
            530                 535                 540
Met Met Met Val Pro Tyr Gln Gln Gln Leu Pro Gln Tyr Pro Gln Gln
545                 550                 555                 560
Gln Met Gln Gln Ile Gly Pro Ser Asn Pro Phe Gly Asp Pro Phe Leu
                565                 570                 575
Ser Phe Pro Gln Thr Ser Val Pro Pro Gly Gly His His Asn Leu Ile
                580                 585                 590

<210> SEQ ID NO 3
<211> LENGTH: 1788
<212> TYPE: DNA
<213> ORGANISM: Cucumis melo
<220> FEATURE:
<223> OTHER INFORMATION: CLARP1 with c.1599_1600insCAGCAACAA

<400> SEQUENCE: 3
atgggcacat tcagagctt ccgcaaagct tatggcgctc tcaaagattc caccaaggtc      60
ggcctcgcta aggtcaacag cgaattcaag gatttggata tcgccatcgt taaggctacc     120
aatcacgttg aatgtccgcc taagaacgt catgttcgaa aaattttttc ggctacgtcc     180
gttgtgagac ctcgggcaga tgtggcgtat tgtattcatg cattggcgaa gagattgtcg     240
aagacgcgga attggatcgt tgccttgaag acgttgatag ttgtacatag gacattgaga     300
gagggagatc ccaccttcag gaagaaactt cttaattatt cacacagagg acatattctc     360
caaatatcca attttaagga tgattcgagt cctcttgctt gggattgttc tgcttgggta     420
```

-continued

```
aggacatatg ccctttttct agaagagaga cttgaatgtt atagaatctt gaagtatgat    480
attgaatcgg aacgtctaac gaaaacatca cctggatcga cgaaggtcca tagtaggaca    540
cgattgctga actctgatga gctactggag cagctacccg cattgcagca acttctctac    600
cgccttatgg gatgtcagcc agaaggagga gcttacagca actatcttat ccagtatgcc    660
ctggctttgg tactcaaaga gagctttaaa atatattgtg cgataaatga tggaataata    720
aatcttgtgg acatgttctt tgatatgcca aggcatgatg cagttaaagc tctcaatata    780
tacaaaagag caagcaacca ggctgaaaat cttgcggatt tttacgaata ctgtaaggga    840
ttggaacttg ctagaacttt tcagtttccc actttgaagc agccacctcc atcatttctt    900
tcaacaatgg aggagtatat aagagaagca ccacagactg ttctgttaa taagagactg     960
gaataccgag agacagagct attgacacag gaagaggata gcccgaaga tcagccgaa     1020
attgaaaagg aggttgaaaa tgttgaggac aacaaaccac tggttgaaac agaggaagaa   1080
ccccaacaga aggaagagga ggttgctgaa cctccacctc taatagaaac ccacgaccca   1140
agtgatcttc tgggtctgaa tgaaataaat cccaaagctg cagaaataga agaaagcaat   1200
gctttagctc ttgctattgt tacaaatggg aatgacccat cttcttcaaa tcgtgcattg   1260
agtgaaattg gcggtagtgg ttgggagcta gcgcttgtta ccacaccaag caataatact   1320
ggtccttctg tcgaaggcag actggccggg ggctttgaca agctattgct tgatagcttg   1380
tatgaagatg aacatgccag aagacatctt cagcttcaga atgctggata tggaccatac   1440
ggggaaatga tggtacagaa tccattcgaa cagcatgacc cgttttcatt gtcgagcaac   1500
atagcgcctc ctccgaacgt gcaaatggca atgatggctc aacaacaaca aatgcttttc   1560
caacaccaac aacaaccatt acaaagcaat accttccctc agcaacaaca gcaacaacag   1620
cagttacatt caaatgactc aatgatgatg gttccttatc aacaacagtt gcctcaatac   1680
ccacaacaac aaatgcaaca aattggtcct tctaatccat ttggtgaccc ttttctttcc   1740
tttcctcaaa cttcagtacc cccaggagga catcataatc taatctag              1788
```

<210> SEQ ID NO 4
<211> LENGTH: 595
<212> TYPE: PRT
<213> ORGANISM: Cucumis melo
<220> FEATURE:
<223> OTHER INFORMATION: CLARP1 with c.1599_1600insCAGCAACAA

<400> SEQUENCE: 4

```
Met Gly Thr Phe Gln Ser Phe Arg Lys Ala Tyr Gly Ala Leu Lys Asp
1               5                   10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Ser Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser His Arg Gly His Ile Leu Gln Ile Ser Asn Phe Lys Asp Asp
```

```
            115                 120                 125
Ser Ser Pro Leu Ala Trp Asp Cys Ser Ala Trp Val Arg Thr Tyr Ala
130                 135                 140
Leu Phe Leu Glu Glu Arg Leu Glu Cys Tyr Arg Ile Leu Lys Tyr Asp
145                 150                 155                 160
Ile Glu Ser Glu Arg Leu Thr Lys Thr Ser Pro Gly Ser Thr Lys Val
                165                 170                 175
His Ser Arg Thr Arg Leu Leu Asn Ser Asp Glu Leu Leu Glu Gln Leu
            180                 185                 190
Pro Ala Leu Gln Gln Leu Leu Tyr Arg Leu Met Gly Cys Gln Pro Glu
        195                 200                 205
Gly Gly Ala Tyr Ser Asn Tyr Leu Ile Gln Tyr Ala Leu Ala Leu Val
    210                 215                 220
Leu Lys Glu Ser Phe Lys Ile Tyr Cys Ala Ile Asn Asp Gly Ile Ile
225                 230                 235                 240
Asn Leu Val Asp Met Phe Phe Asp Met Pro Arg His Asp Ala Val Lys
                245                 250                 255
Ala Leu Asn Ile Tyr Lys Arg Ala Ser Asn Gln Ala Glu Asn Leu Ala
            260                 265                 270
Asp Phe Tyr Glu Tyr Cys Lys Gly Leu Glu Leu Ala Arg Thr Phe Gln
        275                 280                 285
Phe Pro Thr Leu Lys Gln Pro Pro Ser Phe Leu Ser Thr Met Glu
    290                 295                 300
Glu Tyr Ile Arg Glu Ala Pro Gln Thr Gly Ser Val Asn Lys Arg Leu
305                 310                 315                 320
Glu Tyr Arg Glu Thr Glu Leu Leu Thr Gln Glu Asp Lys Pro Glu
                325                 330                 335
Glu Ser Ala Glu Ile Glu Lys Glu Val Glu Asn Val Glu Asp Asn Lys
            340                 345                 350
Pro Leu Val Glu Thr Glu Glu Pro Gln Gln Lys Glu Glu Glu Val
        355                 360                 365
Ala Glu Pro Pro Pro Leu Ile Glu Thr His Asp Pro Ser Asp Leu Leu
    370                 375                 380
Gly Leu Asn Glu Ile Asn Pro Lys Ala Ala Glu Ile Glu Glu Ser Asn
385                 390                 395                 400
Ala Leu Ala Leu Ala Ile Val Thr Asn Gly Asn Asp Pro Ser Ser Ser
                405                 410                 415
Asn Arg Ala Leu Ser Glu Ile Gly Gly Ser Gly Trp Glu Leu Ala Leu
            420                 425                 430
Val Thr Thr Pro Ser Asn Asn Thr Gly Pro Ser Val Glu Gly Arg Leu
        435                 440                 445
Ala Gly Gly Phe Asp Lys Leu Leu Asp Ser Leu Tyr Glu Asp Glu
    450                 455                 460
His Ala Arg Arg His Leu Gln Leu Gln Asn Ala Gly Tyr Gly Pro Tyr
465                 470                 475                 480
Gly Glu Met Met Val Gln Asn Pro Phe Glu Gln His Asp Pro Phe Ser
                485                 490                 495
Leu Ser Ser Asn Ile Ala Pro Pro Asn Val Gln Met Ala Met Met
            500                 505                 510
Ala Gln Gln Gln Gln Met Leu Phe Gln His Gln Gln Pro Leu Gln
        515                 520                 525
Ser Asn Thr Phe Pro Gln Gln Gln Gln Gln Gln Leu His Ser
    530                 535                 540
```

Asn Asp Ser Met Met Met Val Pro Tyr Gln Gln Gln Leu Pro Gln Tyr
545                 550                 555                 560

Pro Gln Gln Gln Met Gln Gln Ile Gly Pro Ser Asn Pro Phe Gly Asp
            565                 570                 575

Pro Phe Leu Ser Phe Pro Gln Thr Ser Val Pro Pro Gly Gly His His
        580                 585                 590

Asn Leu Ile
    595

<210> SEQ ID NO 5
<211> LENGTH: 1791
<212> TYPE: DNA
<213> ORGANISM: Cucumis sativus
<220> FEATURE:
<223> OTHER INFORMATION: CLARP1

<400> SEQUENCE: 5

| | | | |
|---|---|---|---|
| atgggcacat tcagagcttt cgcaaagct tatggggctc tcaaagattc caccaaggtc | | | 60 |
| ggcctcgcta aggtcaacag cgagttcaag gatttggata tcgccattgt taaggctacc | | | 120 |
| aatcacgttg aatgtccgcc taaggaacgt catgttcgaa aaattttttc ggctacgtcc | | | 180 |
| gttgtgagac taggggcaga tgtggcgtat tgtattcatg cattggcgaa gagattgtcg | | | 240 |
| aagacgcgga attggatcgt tgccttgaag acgttgatag ttgtacatag acattgaga | | | 300 |
| gagggagatc caaccttcag gaagaacttc tcaattatt cacacagagg acatattctc | | | 360 |
| caaatatcaa attttaagga tgattcaagt cctcttgctt gggattgttc agcttgggta | | | 420 |
| aggacatatg cccttttcct agaagagaga cttgaatgtt atagaatctt gaagtatgat | | | 480 |
| attgaatcgg aacgtctaac gaaaacatca cctggatcaa cgaaggtcca tagtaggaca | | | 540 |
| cgattgctga actctgatga gctactggag cagctacccg cattgcagca acttctctac | | | 600 |
| cgccttatgg gatgtcagcc agaaggagga gcttacagca attatcttat ccaatatgcc | | | 660 |
| ctggctttgg tactcaaaga gagctttaaa atatattgtg cgataaatga tggaataata | | | 720 |
| aatcttgtgg acatgttctt tgatatgcca aggcatgatg cagttaaagc tctcaatata | | | 780 |
| tacaaaagag caagcaacca ggctgaaaat cttgcggatt tttacgaata ctgtaaggga | | | 840 |
| ttggaacttg ctagaacttt tcagtttccc acattgaagc agccacctcc atcatttctt | | | 900 |
| tcaacaatgg aggagtatat aagagaagca ccacaaactg ttctgttaa taagagacta | | | 960 |
| gaataccgag aggcagagca attgacacag gaacaagata gcccgaaga ccaggcgaa | | | 1020 |
| attgaaaagg aagttgaaaa tgttgaggac aacaaaccac cggttgaaac agaggaagaa | | | 1080 |
| ccccaacaga aggaaggga ggttgctgaa cctccacctc taatagcaac ccacgacgca | | | 1140 |
| agtgatcttc tgggtctgaa tgaaataaat cccagagctg cagaaataga agaaagcaat | | | 1200 |
| gctttagctc ttgctattat tacaaatggg aatgatccat cttcttcaaa tcgtgcattg | | | 1260 |
| agtgaaattg gcggtagtgg ttgggagcta gcgcttgtta ccacaccaag caataatgct | | | 1320 |
| ggtccttctg tcgaaggcaa actggccggg ggctttgaca agctattgct tgatagcttg | | | 1380 |
| tatgaagatg aacatgccag aagacatctt cagcttcaga tgccggata tggaccttac | | | 1440 |
| ggagaaatga tggtacataa tccatttgaa cagcatgacc cgttttcatt gtcgagcaac | | | 1500 |
| atagcgcctc ctccgagcgt gcaaatggca atgatggctc aacaacaaca atgctttc | | | 1560 |
| caacaccaac aacaacaacc attacaaagc aatgccttcc ctcagcaaca acaacaatta | | | 1620 |
| cattcaaatg actcaatgat gatggttcct tatcaacaac agttgcctca ataccctcaa | | | 1680 |

```
caacaaatgc aacaaatgca acaaattggt ccttctaatc catttggtga cccttttctt    1740
tcctttcctc aaacttcagt accccccagga ggacatcata atctaatcta g            1791
```

<210> SEQ ID NO 6
<211> LENGTH: 596
<212> TYPE: PRT
<213> ORGANISM: Cucumis sativus
<220> FEATURE:
<223> OTHER INFORMATION: CLARP1

<400> SEQUENCE: 6

```
Met Gly Thr Phe Gln Ser Phe Arg Lys Ala Tyr Gly Ala Leu Lys Asp
1               5                   10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Ser Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser His Arg Gly His Ile Leu Gln Ile Ser Asn Phe Lys Asp Asp
        115                 120                 125

Ser Ser Pro Leu Ala Trp Asp Cys Ser Ala Trp Val Arg Thr Tyr Ala
    130                 135                 140

Leu Phe Leu Glu Glu Arg Leu Glu Cys Tyr Arg Ile Leu Lys Tyr Asp
145                 150                 155                 160

Ile Glu Ser Glu Arg Leu Thr Lys Thr Ser Pro Gly Ser Thr Lys Val
                165                 170                 175

His Ser Arg Thr Arg Leu Leu Asn Ser Asp Glu Leu Leu Glu Gln Leu
            180                 185                 190

Pro Ala Leu Gln Gln Leu Leu Tyr Arg Leu Met Gly Cys Gln Pro Glu
        195                 200                 205

Gly Gly Ala Tyr Ser Asn Tyr Leu Ile Gln Tyr Ala Leu Ala Leu Val
    210                 215                 220

Leu Lys Glu Ser Phe Lys Ile Tyr Cys Ala Ile Asn Asp Gly Ile Ile
225                 230                 235                 240

Asn Leu Val Asp Met Phe Phe Asp Met Pro Arg His Asp Ala Val Lys
                245                 250                 255

Ala Leu Asn Ile Tyr Lys Arg Ala Ser Asn Gln Ala Glu Asn Leu Ala
            260                 265                 270

Asp Phe Tyr Glu Tyr Cys Lys Gly Leu Glu Leu Ala Arg Thr Phe Gln
        275                 280                 285

Phe Pro Thr Leu Lys Gln Pro Pro Ser Phe Leu Ser Thr Met Glu
    290                 295                 300

Glu Tyr Ile Arg Glu Ala Pro Gln Thr Gly Ser Val Asn Lys Arg Leu
305                 310                 315                 320

Glu Tyr Arg Glu Ala Glu Gln Leu Thr Gln Glu Gln Asp Lys Pro Glu
                325                 330                 335

Glu Pro Gly Glu Ile Glu Lys Glu Val Glu Asn Val Glu Asp Asn Lys
            340                 345                 350
```

```
Pro Pro Val Glu Thr Glu Glu Pro Gln Gln Lys Glu Gly Glu Val
        355                 360                 365
Ala Glu Pro Pro Leu Ile Ala Thr His Asp Ala Ser Asp Leu Leu
    370                 375                 380
Gly Leu Asn Glu Ile Asn Pro Arg Ala Ala Glu Ile Glu Glu Ser Asn
385                 390                 395                 400
Ala Leu Ala Leu Ala Ile Ile Thr Asn Gly Asn Asp Pro Ser Ser Ser
                405                 410                 415
Asn Arg Ala Leu Ser Glu Ile Gly Gly Ser Gly Trp Glu Leu Ala Leu
                420                 425                 430
Val Thr Thr Pro Ser Asn Asn Ala Gly Pro Ser Val Gly Lys Leu
                435                 440                 445
Ala Gly Gly Phe Asp Lys Leu Leu Leu Asp Ser Leu Tyr Glu Asp Glu
    450                 455                 460
His Ala Arg Arg His Leu Gln Leu Gln Asn Ala Gly Tyr Gly Pro Tyr
465                 470                 475                 480
Gly Glu Met Met Val His Asn Pro Phe Glu Gln His Asp Pro Phe Ser
                485                 490                 495
Leu Ser Ser Asn Ile Ala Pro Pro Ser Val Gln Met Ala Met Met
                500                 505                 510
Ala Gln Gln Gln Gln Met Leu Phe Gln His Gln Gln Gln Pro Leu
    515                 520                 525
Gln Ser Asn Ala Phe Pro Gln Gln Gln Gln Leu His Ser Asn Asp
    530                 535                 540
Ser Met Met Met Val Pro Tyr Gln Gln Gln Leu Pro Gln Tyr Pro Gln
545                 550                 555                 560
Gln Gln Met Gln Gln Met Gln Gln Ile Gly Pro Ser Asn Pro Phe Gly
                565                 570                 575
Asp Pro Phe Leu Ser Phe Pro Gln Thr Ser Val Pro Pro Gly Gly His
                580                 585                 590
His Asn Leu Ile
        595

<210> SEQ ID NO 7
<211> LENGTH: 1797
<212> TYPE: DNA
<213> ORGANISM: Momordica charantia
<220> FEATURE:
<223> OTHER INFORMATION: CLARP1

<400> SEQUENCE: 7
atgggcacgt tcagagctt tcgcaaagct tatggagctc tcaaggactc caccaaggtc      60
ggtctcgcca aggtcaacag cgagttcaag gatttggata tcgccattgt taaggccacc     120
aatcacgtcg agtgccctcc taaagagcgt catgttcgaa aaatattttc cgcgacgtcg     180
gtggtgaggc ctcgggcgga tgtggcgtat tgcattcatg cgttggcgaa agattgtcg     240 aagacgcgga actggatcgt tgccttgaag acgttgatag ttgtacatag acattgaga     300 gagggtgatc caaccttcag ggaggaactt ctcaactatt cacacagagg acacattctt     360
caaatatcta attttaagga cgattcaagt cctcttgctt gggattgttc tgcatgggta     420
aggacgtatg cccttttctc agaagagcga cttgaatgtt acagaatctt gaagtatgat     480
atcgaatcag aacgttaac gaaaacatca ccaggatcaa gcaaggtaca tagtaggaca     540
cgcttgctga attctgatga gctactggaa cagttacccg cattgcagca gcttctttac     600
```

```
cgcctaattg gatgtcagcc agaaggagca gcttacagta attatctgat ccagtatgcc    660
ctggctctgg tacttaaaga gagctttaag atatattgtg cgataaatga cggaataata    720
aatcttgtgg acatgttctt tgatatgcca aggcacgatg cagttaaagc tctcaatata    780
tacaaaagag ccagcaacca ggctgaaaat cttgcagatt tttatgaata ttgtaaggga    840
ttggaacttg ctagaacttt tcagtttccc acgttgaagc agccacctcc atcatttctt    900
gcaacaatgg aagaatatat aagagaggca ccacagacag ttctgttaa caagagactg    960 gaataccgag aggcagagct attgactcac aaaccagaag agcctgaaga acccaccgaa   1020
accgaaaaga aggttgagaa tgttgatgat gacgaaccac tggtggcaac agaggaagaa   1080
ccccaacaga aggaagagga ggtcgcagaa cctccacctc ttatagcaac tgataatact   1140
agtgatcttc tgggtctgag tgaaataaat cctagagccg cagaaataga ggaaagtaat   1200
gctttagctc ttgcgatagt tacacctggg aatgatacgt cttcttcaag tcgtgcttta   1260
catgacatcg gtggaactag aggttgggag ctagcccttg ttaccacacc aagcaataat   1320
actggtccaa tggtcgacag caaactggcc ggtgggttcg acaagctatt gctcgatagc   1380
ttgtatgaag atgaacatgc cagaagacat cttcagctgc agaacgcagg atatggaaca   1440
tatggcgaaa tgtcagtgca gaatccattc gaacaacacc aacacgaccc gtttgcaatg   1500
tcaagcggag tagcgcctcc cccgaacgtg caaatggcaa tgatgcagca gcagcaaatg   1560
cttttacaac accagcagca acaacagtta caaccaaacg cattcccaca gcagcatcag   1620
cagcaacatc caaatgactc catgatgatg gtaccttatc aacaacagtt gcctcagtac   1680
cctcagcagc aacaacaaca aatgcagcaa cttggcccctt ctaatccatt tggtgaccct   1740
tttctttcct ttcctcaaac ctcggtaccg ccccgaggaa atcataatct aatctaa      1797
```

<210> SEQ ID NO 8
<211> LENGTH: 598
<212> TYPE: PRT
<213> ORGANISM: Momordica charantia
<220> FEATURE:
<223> OTHER INFORMATION: CLARP1

<400> SEQUENCE: 8

```
Met Gly Thr Phe Gln Ser Phe Arg Lys Ala Tyr Gly Ala Leu Lys Asp
1               5                   10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Ser Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser His Arg Gly His Ile Leu Gln Ile Ser Asn Phe Lys Asp Asp
        115                 120                 125

Ser Ser Pro Leu Ala Trp Asp Cys Ser Ala Trp Val Arg Thr Tyr Ala
    130                 135                 140

Leu Phe Leu Glu Glu Arg Leu Glu Cys Tyr Arg Ile Leu Lys Tyr Asp
145                 150                 155                 160
```

```
Ile Glu Ser Glu Arg Leu Thr Lys Thr Ser Pro Gly Ser Ser Lys Val
            165                 170                 175

His Ser Arg Thr Arg Leu Leu Asn Ser Asp Glu Leu Leu Glu Gln Leu
        180                 185                 190

Pro Ala Leu Gln Gln Leu Leu Tyr Arg Leu Ile Gly Cys Gln Pro Glu
    195                 200                 205

Gly Ala Ala Tyr Ser Asn Tyr Leu Ile Gln Tyr Ala Leu Ala Leu Val
210                 215                 220

Leu Lys Glu Ser Phe Lys Ile Tyr Cys Ala Ile Asn Asp Gly Ile Ile
225                 230                 235                 240

Asn Leu Val Asp Met Phe Phe Asp Met Pro Arg His Asp Ala Val Lys
            245                 250                 255

Ala Leu Asn Ile Tyr Lys Arg Ala Ser Asn Gln Ala Glu Asn Leu Ala
        260                 265                 270

Asp Phe Tyr Glu Tyr Cys Lys Gly Leu Glu Leu Ala Arg Thr Phe Gln
    275                 280                 285

Phe Pro Thr Leu Lys Gln Pro Pro Ser Phe Leu Ala Thr Met Glu
290                 295                 300

Glu Tyr Ile Arg Glu Ala Pro Gln Thr Gly Ser Val Asn Lys Arg Leu
305                 310                 315                 320

Glu Tyr Arg Glu Ala Glu Leu Leu Thr His Lys Pro Glu Pro Glu
            325                 330                 335

Glu Pro Thr Glu Thr Glu Lys Lys Val Glu Asn Val Asp Asp Glu
        340                 345                 350

Pro Leu Val Ala Thr Glu Glu Pro Gln Gln Lys Glu Glu Val
    355                 360                 365

Ala Glu Pro Pro Pro Leu Ile Ala Thr Asp Asn Thr Ser Asp Leu Leu
370                 375                 380

Gly Leu Ser Glu Ile Asn Pro Arg Ala Ala Glu Ile Glu Glu Ser Asn
385                 390                 395                 400

Ala Leu Ala Leu Ala Ile Val Thr Pro Gly Asn Asp Thr Ser Ser Ser
            405                 410                 415

Ser Arg Ala Leu His Asp Ile Gly Gly Thr Arg Gly Trp Glu Leu Ala
        420                 425                 430

Leu Val Thr Thr Pro Ser Asn Asn Thr Gly Pro Met Val Asp Ser Lys
    435                 440                 445

Leu Ala Gly Gly Phe Asp Lys Leu Leu Leu Asp Ser Leu Tyr Glu Asp
450                 455                 460

Glu His Ala Arg Arg His Leu Gln Leu Gln Asn Ala Gly Tyr Gly Thr
465                 470                 475                 480

Tyr Gly Glu Met Ser Val Gln Asn Pro Phe Glu Gln His Gln His Asp
            485                 490                 495

Pro Phe Ala Met Ser Ser Gly Val Ala Pro Pro Asn Val Gln Met
        500                 505                 510

Ala Met Met Gln Gln Gln Gln Met Leu Leu Gln His Gln Gln Gln
    515                 520                 525

Gln Leu Gln Pro Asn Ala Phe Pro Gln His Gln Gln His Pro
530                 535                 540

Asn Asp Ser Met Met Met Val Pro Tyr Gln Gln Leu Pro Gln Tyr
545                 550                 555                 560

Pro Gln Gln Gln Gln Gln Met Gln Gln Leu Gly Pro Ser Asn Pro
            565                 570                 575
```

Phe Gly Asp Pro Phe Leu Ser Phe Pro Gln Thr Ser Val Pro Pro Arg
        580                 585                 590

Gly Asn His Asn Leu Ile
        595

<210> SEQ ID NO 9
<211> LENGTH: 1821
<212> TYPE: DNA
<213> ORGANISM: Cucurbita maxima
<220> FEATURE:
<223> OTHER INFORMATION: CLARP1

<400> SEQUENCE: 9

| | | | | | |
|---|---|---|---|---|---|
| atgggcacat | ttcagagctt | ccgcaaagct | tatggagctc | tcaaggactc | caccaaggtc | 60 |
| ggcctcgcca | aggtcaatag | cgaattcaag | gatttggata | tcgccattgt | taaggctacc | 120 |
| aatcatgttg | aatgtccgcc | taaagaacgt | catgttcgga | aaatatttac | ggcgacgtcc | 180 |
| gttgtgaggc | ctcgggcgga | tgtggcgtat | tgcattcatg | cattggcgaa | gagattgtca | 240 |
| aagacgcgga | actggatcgt | tgccttgaag | acgttgatag | ttgtacatag | gacattgaga | 300 |
| gagggtgatc | caactttcag | ggaagaactt | ctcaactatt | cacaaaaagg | acaagttctc | 360 |
| caaatatcaa | attttaagga | tgattcaagt | cctcttgctt | gggattgttc | tgcatgggta | 420 |
| aggacctatg | cccttttttct | agaagagcga | cttgaatgtt | acagagtctt | gaagtatgat | 480 |
| attgaatcgg | aacgtctaac | aaaaacatcg | ccgggatcaa | cgaaggtaca | tagtaggaca | 540 |
| cgcttgctga | actctgatga | gctgctggac | cagctacccg | cattgcagca | ggttctctac | 600 |
| cgccttatgg | gatgtcagcc | agaaggagca | gcgtatagta | attatcttat | ccagtacgcc | 660 |
| ctggctctcg | tactcaaaga | gagctttaaa | atctattgtg | caataaatga | tggaataata | 720 |
| aaccttgtgg | acatgttctt | tggcatgcca | aggcatgatg | cagttaaagc | tctcaatata | 780 |
| tacaaaagag | ccagccacca | ggctgaaaat | cttgcggatt | tttatgaata | ttgtaaggga | 840 |
| ttggaacttg | ctagaacttt | tcagtttccc | atattgaagc | agccgcctcc | atcatttctt | 900 |
| gcaacaatgg | aagaatatat | aagagaagca | ccccagacag | cttctgttaa | taagagactg | 960 |
| gaataccgag | tggcagagga | gatgactgag | aaaccggaag | agcctgagga | acctgctgaa | 1020 |
| attgaaaagg | aggttgaaaa | tgttgacaac | aaacctcttg | aggaaacaga | ggaagaaccc | 1080 |
| caacagaaag | aagagagtgt | ccctgaacct | ccacctctaa | tagcaactga | ggatacaagt | 1140 |
| gattttctgg | gtcttaagga | aataaatcct | aggattgcag | aaattgagca | taacaatgct | 1200 |
| ttagcccttg | ctatagtttc | aaatgggaat | gatccttctt | ctgcaaatcc | tgctttgagt | 1260 |
| gactttggcg | gtagtggttg | ggagctatcc | cttgttacca | caccaaccaa | taatgctggt | 1320 |
| tcaactgtcg | gaagcaaact | ggcgggcggg | ttcgacaagc | tactgctcga | tagcttgtac | 1380 |
| gaagatgaac | atgccagaag | aaatattcag | cttcaaaatg | caggatatgg | aacatacggt | 1440 |
| gaaatgtatg | tgcagaatcc | attccaacag | cagaacgacc | catttgcgat | gtcgagcagt | 1500 |
| atagcgcctc | cttcgaacgt | gcaattagca | atgatggctc | agcagcagca | aatgctttac | 1560 |
| caacagcaac | aacagcagca | gcatcaagcg | ttacaaacaa | acgcgttccc | tcagcaacaa | 1620 |
| cagttgcatt | tagatgagtc | tatgatgatg | gtacctcatc | aacaacagtt | gcctcagagt | 1680 |
| aagtaccctc | aacagcaaca | aatacagcag | caacaacgcc | aacaaatgca | acaatttggt | 1740 |
| cagtctaatc | cttttggaga | ccctttttgtt | ccctttcctc | agaattctgt | accgccgggg | 1800 |
| ggaaatcata | atctaatcta | g | | | | 1821 |

<210> SEQ ID NO 10
<211> LENGTH: 606
<212> TYPE: PRT
<213> ORGANISM: Cucurbita maxima
<220> FEATURE:
<223> OTHER INFORMATION: CLARP1

<400> SEQUENCE: 10

```
Met Gly Thr Phe Gln Ser Phe Arg Lys Ala Tyr Gly Ala Leu Lys Asp
1               5                   10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Thr Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser Gln Lys Gly Gln Val Leu Gln Ile Ser Asn Phe Lys Asp Asp
        115                 120                 125

Ser Ser Pro Leu Ala Trp Asp Cys Ser Ala Trp Val Arg Thr Tyr Ala
    130                 135                 140

Leu Phe Leu Glu Glu Arg Leu Glu Cys Tyr Arg Val Leu Lys Tyr Asp
145                 150                 155                 160

Ile Glu Ser Glu Arg Leu Thr Lys Thr Ser Pro Gly Ser Thr Lys Val
                165                 170                 175

His Ser Arg Thr Arg Leu Leu Asn Ser Asp Glu Leu Leu Asp Gln Leu
            180                 185                 190

Pro Ala Leu Gln Gln Val Leu Tyr Arg Leu Met Gly Cys Gln Pro Glu
        195                 200                 205

Gly Ala Ala Tyr Ser Asn Tyr Leu Ile Gln Tyr Ala Leu Ala Leu Val
    210                 215                 220

Leu Lys Glu Ser Phe Lys Ile Tyr Cys Ala Ile Asn Asp Gly Ile Ile
225                 230                 235                 240

Asn Leu Val Asp Met Phe Phe Gly Met Pro Arg His Asp Ala Val Lys
                245                 250                 255

Ala Leu Asn Ile Tyr Lys Arg Ala Ser His Gln Ala Glu Asn Leu Ala
            260                 265                 270

Asp Phe Tyr Glu Tyr Cys Lys Gly Leu Glu Leu Ala Arg Thr Phe Gln
        275                 280                 285

Phe Pro Ile Leu Lys Gln Pro Pro Ser Phe Leu Ala Thr Met Glu
    290                 295                 300

Glu Tyr Ile Arg Glu Ala Pro Gln Thr Ala Ser Val Asn Lys Arg Leu
305                 310                 315                 320

Glu Tyr Arg Val Ala Glu Glu Met Thr Glu Lys Pro Glu Glu Pro Glu
                325                 330                 335

Glu Pro Ala Glu Ile Glu Lys Glu Val Glu Asn Val Asp Asn Lys Pro
            340                 345                 350

Leu Glu Glu Thr Glu Glu Glu Pro Gln Gln Lys Glu Glu Ser Val Pro
        355                 360                 365

Glu Pro Pro Pro Leu Ile Ala Thr Glu Asp Thr Ser Asp Phe Leu Gly
```

```
                    370                 375                 380
Leu Lys Glu Ile Asn Pro Arg Ile Ala Glu Ile His Asn Asn Ala
385                 390                 395                 400

Leu Ala Leu Ala Ile Val Ser Asn Gly Asn Asp Pro Ser Ala Asn
                405                 410                 415

Pro Ala Leu Ser Asp Phe Gly Gly Ser Gly Trp Glu Leu Ser Leu Val
                420                 425                 430

Thr Thr Pro Thr Asn Asn Ala Gly Ser Thr Val Gly Ser Lys Leu Ala
                435                 440                 445

Gly Gly Phe Asp Lys Leu Leu Leu Asp Ser Leu Tyr Glu Asp Glu His
                450                 455                 460

Ala Arg Arg Asn Ile Gln Leu Gln Asn Ala Gly Tyr Gly Thr Tyr Gly
465                 470                 475                 480

Glu Met Tyr Val Gln Asn Pro Phe Gln Gln Asn Asp Pro Phe Ala
                485                 490                 495

Met Ser Ser Ser Ile Ala Pro Pro Ser Asn Val Gln Leu Ala Met Met
                500                 505                 510

Ala Gln Gln Gln Gln Met Leu Tyr Gln Gln Gln Gln Gln Gln Gln His
                515                 520                 525

Gln Ala Leu Gln Thr Asn Ala Phe Pro Gln Gln Gln Leu His Leu
                530                 535                 540

Asp Glu Ser Met Met Met Val Pro His Gln Gln Gln Leu Pro Gln Ser
545                 550                 555                 560

Lys Tyr Pro Gln Gln Gln Ile Gln Gln Gln Arg Gln Gln Met
                565                 570                 575

Gln Gln Phe Gly Gln Ser Asn Pro Phe Gly Asp Pro Phe Val Pro Phe
                580                 585                 590

Pro Gln Asn Ser Val Pro Pro Gly Gly Asn His Asn Leu Ile
                595                 600                 605

<210> SEQ ID NO 11
<211> LENGTH: 1785
<212> TYPE: DNA
<213> ORGANISM: Citrullus lanatus
<220> FEATURE:
<223> OTHER INFORMATION: CLARP1

<400> SEQUENCE: 11
atgggcacat tcagagctt ccgcaaagct tatggcgctc tcaaagactc caccaaggtc      60
ggcctcgcta aggtcaacag cgaattcaag gatttggata tcgccattgt caaggctacc    120
aatcatgttg aatgtccgcc taaagaacgt catgttcgaa aaatatttc ggccacgtct     180 gtggtgaggc ctagggcgga tgtggcgtat tgtattcatg cattggcgaa gagattgtcg    240
aagacgcgga attggatcgt tgccttgaag acgttgatag ttgtacatag acattgaga    300 gagggtgatc caaccttcag ggaagaactt ctcaattatt cacacagagg acatattctc    360
caaatatcaa attttaagga tgattcaagt cctcttgctt gggattgttc tgcatgggta    420
aggacatatg ccctttttct agaagagaga cttgaatgtt acagaatctt gaagtatgac    480
attgaatcgg aacgcctaac caaaacatca ccaggatcga cgaaggtaca tagtaggaca    540
cggttgctga actgtgatga gctactggag cagctacccg cattgcagca gcttctctac    600
cgccttatgg gatgtcagcc agaaggagga gcttacagca attatctcat ccagtatgca    660
ctggctctgg tactcaaaga gagctttaaa atatattgtg cgataaatga tggaataata    720
aatcttgtgg acatgttctt tgatatgcca aggcacgatg cagttaaagc tctcaatata    780
```

```
tacaaaagag caagcaacca ggctgaaaat cttgcggatt tttacgaata ttgtaaggga    840
ttggaacttg ctagaacttt tcagtttccc acattgaagc agccacctcc atcatttctt    900
tcaacaatgg aagagtatat aagagaagca ccacagacag gttctgttaa taagagactg    960
gaataccgag aggcagagca aactcaagaa ccggagaagc cgaagaacc tggcgaaatt    1020
gaaaaggaag ttgaaaatgt tgaggacaac aaaccactgg ttgaaacaga ggaagaaccc    1080
caacacaagg aagaggaggt cgttgaacct ccacctctaa tagcaaccga cacaagtgat    1140
cttctgggtc tgaatgaaat aaatcctaaa gctgcagaaa tagaaaaaag caatgcttta    1200
gctcttgcta taattacaga tgggaatgat ccatcttcgt caagtcgtgc tttgggtgaa    1260
attggcggta gtggttggga gctagcgctt gttaccacac caagcaataa tgctggtcca    1320
acggtcgaaa gcagactggc cggtggtttt gacaagctat tgcttgatag cttgtatgaa    1380
gatgaacatg ccagaagaca tcttcagctg cagaatgctg atatggacc atacggcgaa    1440
atgatggtgc agaatccatt cgaacagcac gacccgtttt caatgtcgag caacatagcg    1500
cctcccccaa acgtgcaaat ggcaatgatg gctcaacaac atcaaatgct tttccaacac    1560
cagcaacaac aaccattaca aagcaacgcc ttccctcagc aacaacagca acagcagcaa    1620
ttacattcaa atgactccat gatgatggta ccttatcaac aacaattgcc acagtaccct    1680
caacaacaaa tgcaacaact tggtccttct aatccatttg gtgacccgtt tctttccttt    1740
cctcaaactt cagtaccccc aggaggaaat cataatctaa tctag                    1785
```

<210> SEQ ID NO 12
<211> LENGTH: 594
<212> TYPE: PRT
<213> ORGANISM: Citrullus lanatus
<220> FEATURE:
<223> OTHER INFORMATION: CLARP1

<400> SEQUENCE: 12

```
Met Gly Thr Phe Gln Ser Phe Arg Lys Ala Tyr Gly Ala Leu Lys Asp
1               5                   10                  15

Ser Thr Lys Val Gly Leu Ala Lys Val Asn Ser Glu Phe Lys Asp Leu
            20                  25                  30

Asp Ile Ala Ile Val Lys Ala Thr Asn His Val Glu Cys Pro Pro Lys
        35                  40                  45

Glu Arg His Val Arg Lys Ile Phe Ser Ala Thr Ser Val Val Arg Pro
    50                  55                  60

Arg Ala Asp Val Ala Tyr Cys Ile His Ala Leu Ala Lys Arg Leu Ser
65                  70                  75                  80

Lys Thr Arg Asn Trp Ile Val Ala Leu Lys Thr Leu Ile Val Val His
                85                  90                  95

Arg Thr Leu Arg Glu Gly Asp Pro Thr Phe Arg Glu Glu Leu Leu Asn
            100                 105                 110

Tyr Ser His Arg Gly His Ile Leu Gln Ile Ser Asn Phe Lys Asp Asp
        115                 120                 125

Ser Ser Pro Leu Ala Trp Asp Cys Ser Ala Trp Val Arg Thr Tyr Ala
    130                 135                 140

Leu Phe Leu Glu Glu Arg Leu Glu Cys Tyr Arg Ile Leu Lys Tyr Asp
145                 150                 155                 160

Ile Glu Ser Glu Arg Leu Thr Lys Thr Ser Pro Gly Ser Thr Lys Val
                165                 170                 175

His Ser Arg Thr Arg Leu Leu Asn Cys Asp Glu Leu Leu Glu Gln Leu
```

```
            180             185             190
Pro Ala Leu Gln Gln Leu Leu Tyr Arg Leu Met Gly Cys Gln Pro Glu
        195                 200                 205

Gly Gly Ala Tyr Ser Asn Tyr Leu Ile Gln Tyr Ala Leu Ala Leu Val
210                 215                 220

Leu Lys Glu Ser Phe Lys Ile Tyr Cys Ala Ile Asn Asp Gly Ile Ile
225                 230                 235                 240

Asn Leu Val Asp Met Phe Phe Asp Met Pro Arg His Asp Ala Val Lys
                245                 250                 255

Ala Leu Asn Ile Tyr Lys Arg Ala Ser Asn Gln Ala Glu Asn Leu Ala
            260                 265                 270

Asp Phe Tyr Glu Tyr Cys Lys Gly Leu Glu Leu Ala Arg Thr Phe Gln
        275                 280                 285

Phe Pro Thr Leu Lys Gln Pro Pro Ser Phe Leu Ser Thr Met Glu
    290                 295                 300

Glu Tyr Ile Arg Glu Ala Pro Gln Thr Gly Ser Val Asn Lys Arg Leu
305                 310                 315                 320

Glu Tyr Arg Glu Ala Glu Gln Thr Gln Glu Pro Glu Lys Pro Glu Glu
                325                 330                 335

Pro Gly Glu Ile Glu Lys Glu Val Glu Asn Val Glu Asp Asn Lys Pro
            340                 345                 350

Leu Val Glu Thr Glu Glu Pro Gln His Lys Glu Glu Val Val
        355                 360                 365

Glu Pro Pro Pro Leu Ile Ala Thr Asp Thr Ser Asp Leu Leu Gly Leu
    370                 375                 380

Asn Glu Ile Asn Pro Lys Ala Ala Glu Ile Glu Lys Ser Asn Ala Leu
385                 390                 395                 400

Ala Leu Ala Ile Ile Thr Asp Gly Asn Asp Pro Ser Ser Ser Ser Arg
                405                 410                 415

Ala Leu Gly Glu Ile Gly Gly Ser Gly Trp Glu Leu Ala Leu Val Thr
            420                 425                 430

Thr Pro Ser Asn Asn Ala Gly Pro Thr Val Glu Ser Arg Leu Ala Gly
        435                 440                 445

Gly Phe Asp Lys Leu Leu Leu Asp Ser Leu Tyr Glu Asp His Ala
    450                 455                 460

Arg Arg His Leu Gln Leu Gln Asn Ala Gly Tyr Gly Pro Tyr Gly Glu
465                 470                 475                 480

Met Met Val Gln Asn Pro Phe Glu Gln His Asp Pro Phe Ser Met Ser
                485                 490                 495

Ser Asn Ile Ala Pro Pro Asn Val Gln Met Ala Met Met Ala Gln
            500                 505                 510

Gln His Gln Met Leu Phe Gln His Gln Gln Gln Pro Leu Gln Ser
        515                 520                 525

Asn Ala Phe Pro Gln Gln Gln Gln Gln Gln Leu His Ser Asn
    530                 535                 540

Asp Ser Met Met Met Val Pro Tyr Gln Gln Leu Pro Gln Tyr Pro
545                 550                 555                 560

Gln Gln Gln Met Gln Leu Gly Pro Ser Asn Pro Phe Gly Asp Pro
                565                 570                 575

Phe Leu Ser Phe Pro Gln Thr Ser Val Pro Pro Gly Gly Asn His Asn
            580                 585                 590

Leu Ile
```

```
<210> SEQ ID NO 13
<211> LENGTH: 19
<212> TYPE: DNA
<213> ORGANISM: Cucumis melo
<220> FEATURE:
<223> OTHER INFORMATION: Forward primer CLARP1 with
      c.1599_1600insCAGCAACAA

<400> SEQUENCE: 13
ttccaacacc aacaacaac                                              19

<210> SEQ ID NO 14
<211> LENGTH: 19
<212> TYPE: DNA
<213> ORGANISM: Cucumis melo
<220> FEATURE:
<223> OTHER INFORMATION: Reverse primer CLARP1 with
      c.1599_1600insCAGCAACAA

<400> SEQUENCE: 14
aggaaaggaa agaaaaggg                                              19

<210> SEQ ID NO 15
<211> LENGTH: 10
<212> TYPE: DNA
<213> ORGANISM: Cucumis melo
<220> FEATURE:
<223> OTHER INFORMATION: CLARP1 insertion

<400> SEQUENCE: 15
tcagcaacaa                                                        10
```

CYSDV RESISTANCE IN MEMBERS OF THE CUCURBITACEAE FAMILY

RELATED APPLICATIONS AND INCORPORATION BY REFERENCE

This application is a continuation-in-part application of international patent application Serial No. PCT/EP2019/070534 filed 30 Jul. 2019, which published as PCT Publication No. WO 2020/025631 on 6 Feb. 2020, which claims benefit of international patent application Serial No. PCT/EP2018/070904 filed 1 Aug. 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named Y7954_00477SL.txt and is 44.4 kbytes in size.

FIELD OF THE INVENTION

The present invention relates to a modified gene that provides resistance to Cucurbit Yellow Stunting Disorder virus (CYSDV) when present in a plant of the Cucurbitaceae family. The invention further relates to progeny, seed, and fruit of the plant that is resistant against CYSDV. The invention also relates to propagation material suitable for producing the plant that is resistant to CYSDV. Additionally, the invention relates to methods for producing, identifying, and selecting a plant of the Cucurbitaceae family having resistance against CYSDV.

BACKGROUND OF THE INVENTION

With rising concerns of a global food shortage in the future, plant viral diseases pose a major threat to world agriculture and the ability for sustained food production. CYSDV, a member of the genus Crinivirus belonging to the family Closteroviridae, is one of the most widely distributed viruses amongst members of the Cucurbitaceae family, including melons, watermelons, summer and winter squash, pumpkins, gourds and cucumbers. CYSDV has the potential to cause significant damage to Cucurbit production, and is presently an economic problem in countries such as the United States, Southern Europe and countries in the Middle East.

Symptoms of CYSDV in melon and cucumbers, for example, include severe yellowing symptoms that characteristically begin with the appearance of interveinal chlorosis or mottling that intensifies with leaf aging. Eventually the entire leaf becomes yellow except for the veins. Plants are often stunted or severely stunted. Fruits from CYSDV-infected plants have reduced quality, reduced size and yield.

CYSDV is spread from infected to uninfected plant by the whitefly (*Bemisia tabaci* Genn.) biotypes A, B and Q. Epidemics of CYSDV infection are driven by heavy infestations of whiteflies and overwintering of the virus in symptomless alterative host species such as alfalfa and lettuce. Since the life cycle of CYSDV is strongly dependent on its vector, management of the infection has mainly concentrated on combating the whitefly. However to have an effective means of controlling the disease, a two-pronged approach is required that not only looks at ways of controlling the vector, but also developing host resistance.

Details about CYSDV entry, replication and spread are not well characterized in the art. One way in which viruses may gain access to the plant cell is through a cellular process called clathrin-mediated endocytosis (CME). CME is known to occur in both animal and plant cells. CME is utilized by the cell to absorb biomolecules by the inward budding of plasma membrane vesicles containing receptors specific to the biomolecules. Viruses such as CYSDV may hijack this natural cellular process such that they are internalized inside these clathrin-coated vesicles in order to breach the plasma membrane, and gain entry into the cell where they can replicate and spread. The process of CME involves a number of proteins, kinases and lipids to facilitate the invagination and budding of the clathrin coated vesicles.

While sources of CYSDV resistance for various members of the Cucurbitaceae family are known to exist, no gene(s) have previously been described that are responsible for the genetic basis of this resistance.

Citation or identification of any document in this application is not an admission that such document is available as prior art to the present invention.

SUMMARY OF THE INVENTION

It is an object of the present invention to provide a gene(s) that leads to CYSDV resistance in a plant of the Cucurbitaceae family, in particular melon (*Cucumis melo*) plants.

In the research that led to the present invention, novel plants of the Cucurbitaceae family, in particular *Cucumis melo* plants, were developed that are highly resistant to CYSDV. It was surprisingly found that the resistance resulted from modifications in a clathrin assembly protein gene herein abbreviated as CLAPR1.

Based on its conserved signature domains, it is predicted by the present inventors that CLAPR1 has a role in the CME process that results in the assembly of clathrin triskelia into the ordered structure known as a clathrin cage (e.g. clathrin coat assembly; Gene Ontology Accession: GO:0048268). Based on the present invention, it is hypothesized that modifications to the CLAPR1 gene and/or the encoded protein will lead to a disruption of CME, preventing the virus from utilizing CME to gain entry into the cell and hence, provide resistance to CYSDV. Modifications to the CLAPR1 gene and the resultant resistance to CYSDV, like those that were found in the present research, would be widely applicable to other members of the Cucurbitaceae family in which an orthologous CLAPR1 gene with a similar function exists.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a *Cucumis melo* plant comprising the modified CLAPR1 gene of the invention in its genome and which confers resistance to CYSDV were deposited under accession number NCIMB 42992 on 27 Mar. 2018 with NCIMB Ltd. (Ferguson Building, Craibstone Estate, Bucksburn, Aberdeen, AB21 9YA). The Deposit with NCIMB Ltd., under deposit accession number NCIMB 42992 was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Multiple sequence alignment of orthologous CLAPR1 protein sequences of *Cucumis melo* (melon)—SEQ ID NO: 2; *Cucumis sativus* (cucumber)—SEQ ID NO: 6; *Momordica charantia* (bitter melon)—SEQ ID NO: 8; *Cucurbita maxima* (squash)—SEQ ID NO: 10; and *Citrullus lanatus* (watermelon)—SEQ ID NO: 12.

The following symbols are used below the alignment:
* all residues in that column are identical
: conserved substitutions have been observed
. semi-conserved substitutions have been observed
  no match (space)

Figure 4:
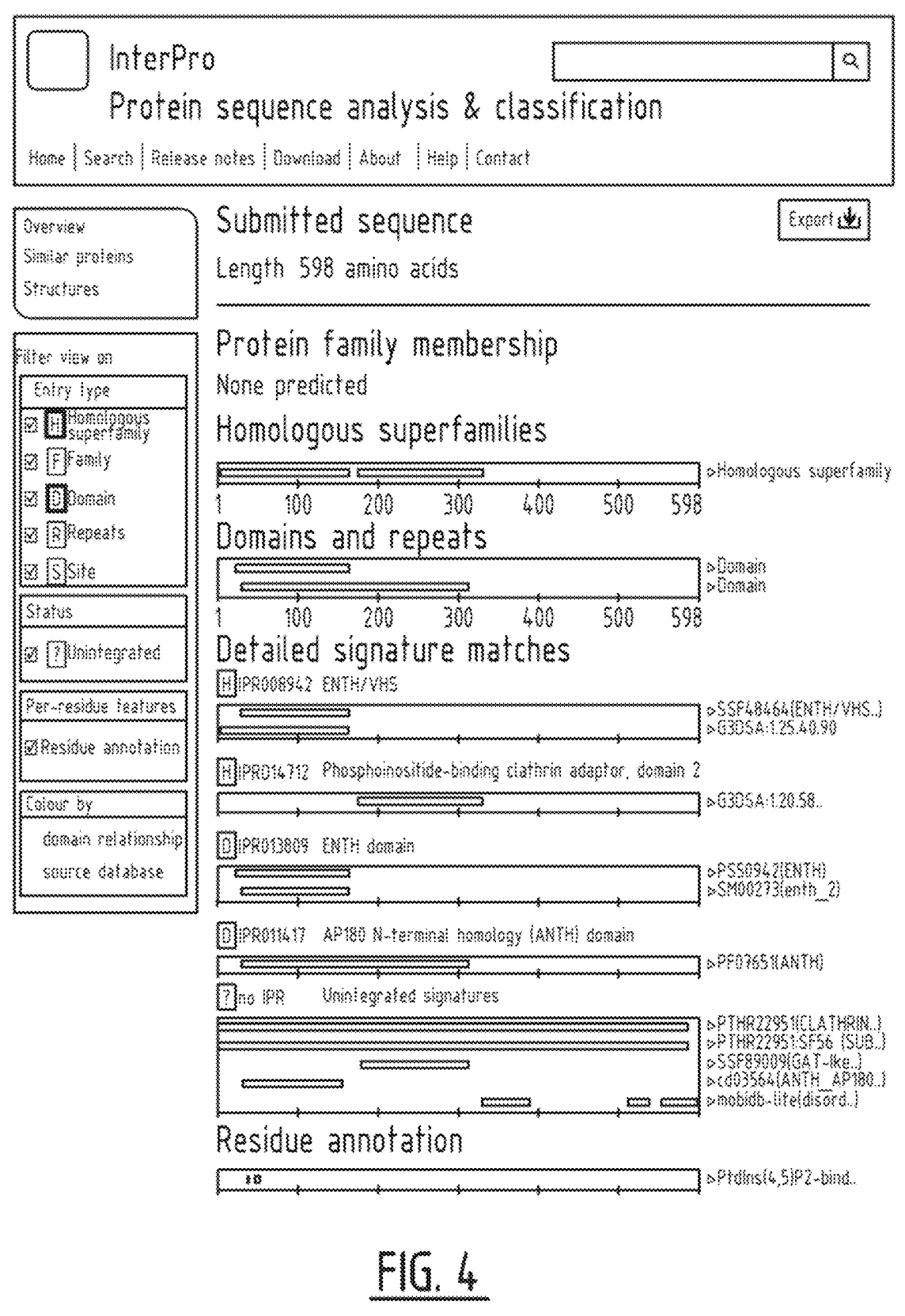
Figure 6:
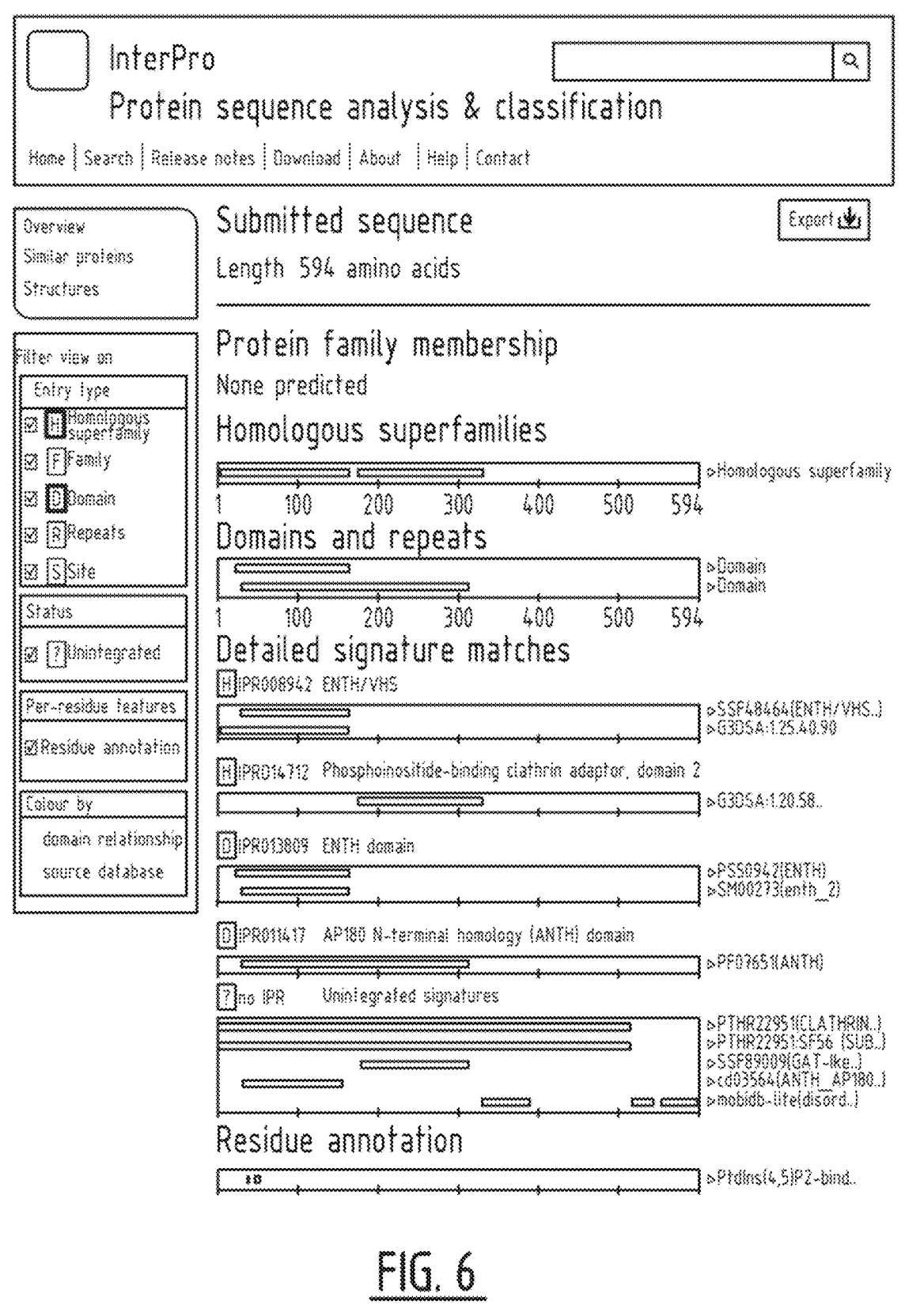

FIGS. 2-6: Functional analysis of orthologous CLAPR1 protein sequences of *Cucumis melo* (melon)—SEQ ID NO: 2; *Cucumis sativus* (cucumber)—SEQ ID NO: 6; *Momordica charantia* (bitter melon)—SEQ ID NO: 8; *Cucurbita maxima* (squash)—SEQ ID NO: 10; and *Citrullus lanatus* (watermelon)—SEQ ID NO: 12 using InterProScan. All CLAPR1 protein orthologs comprise an ENTH/VHS domain (IPR008942), Phosphoinositide-binding clathrin adaptor domain 2 (IPR014712), ENTH domain (IPR013809) and an AP180 N-terminal homology (ANTH) domain (IPR013809). CLAPR1 is predicted to have a role in clathrin coat assembly (Gene Ontology Accession: GO:0048268).

Figure 3:
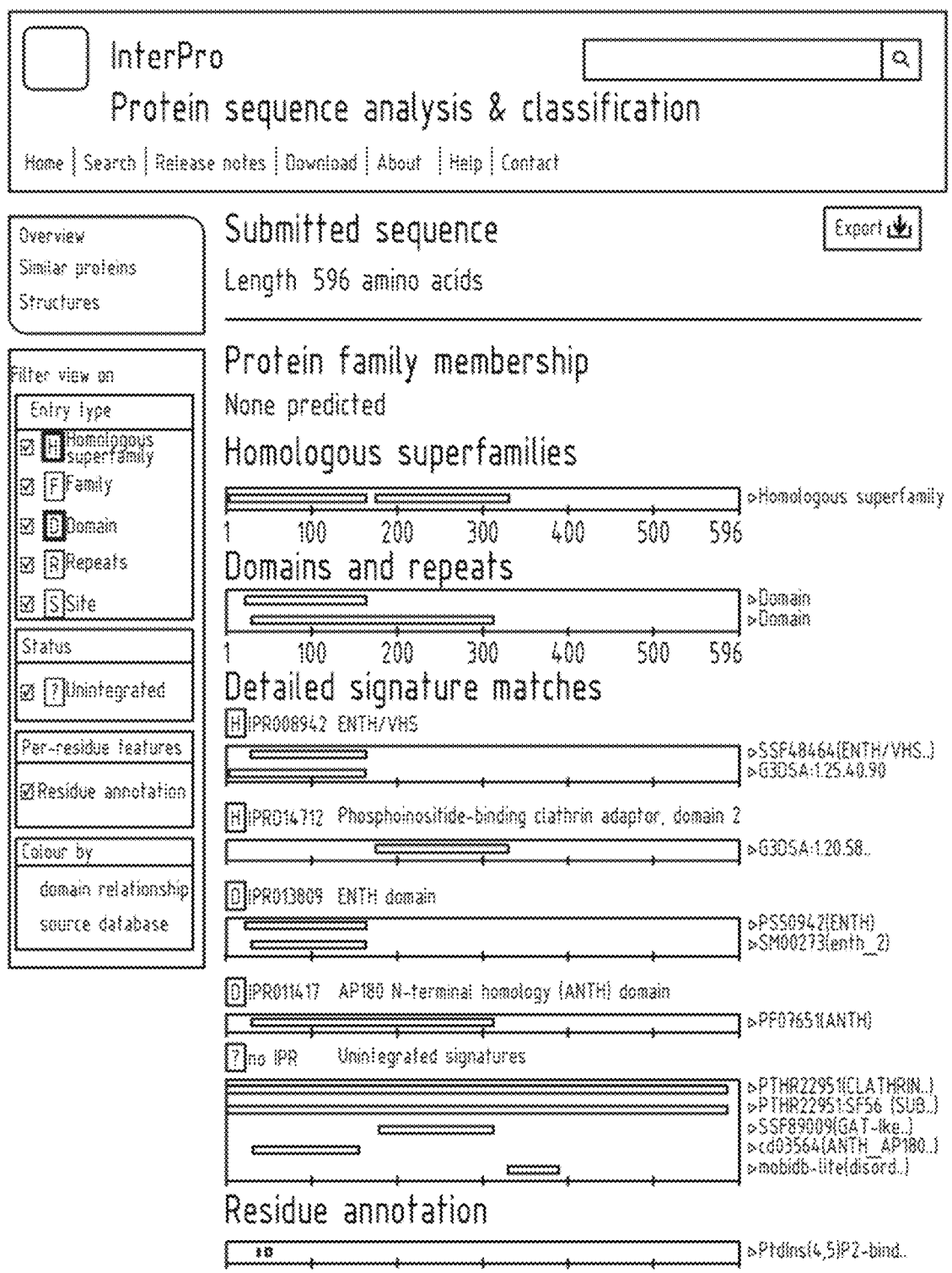
Figure 5:
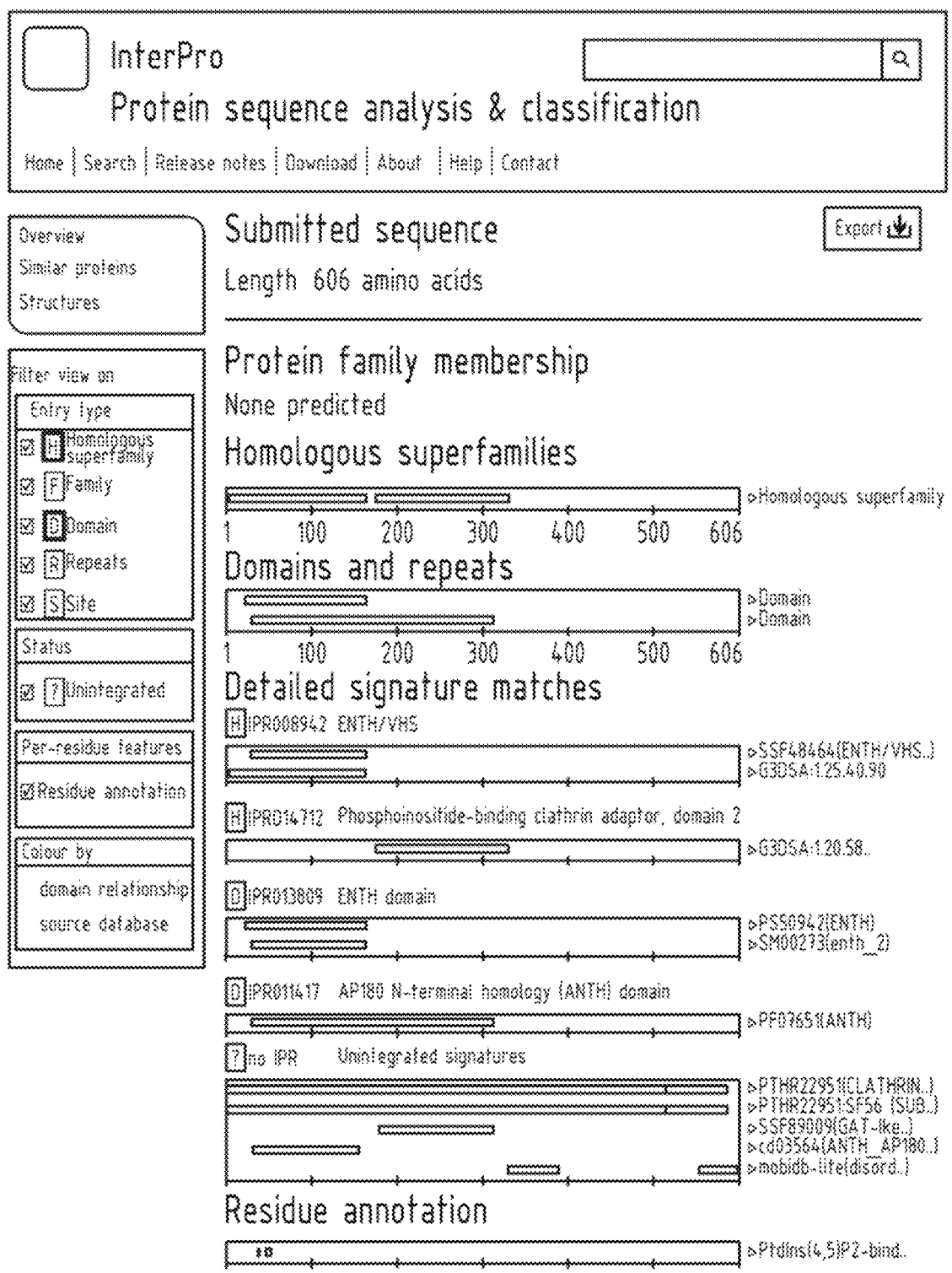
Figure 7:
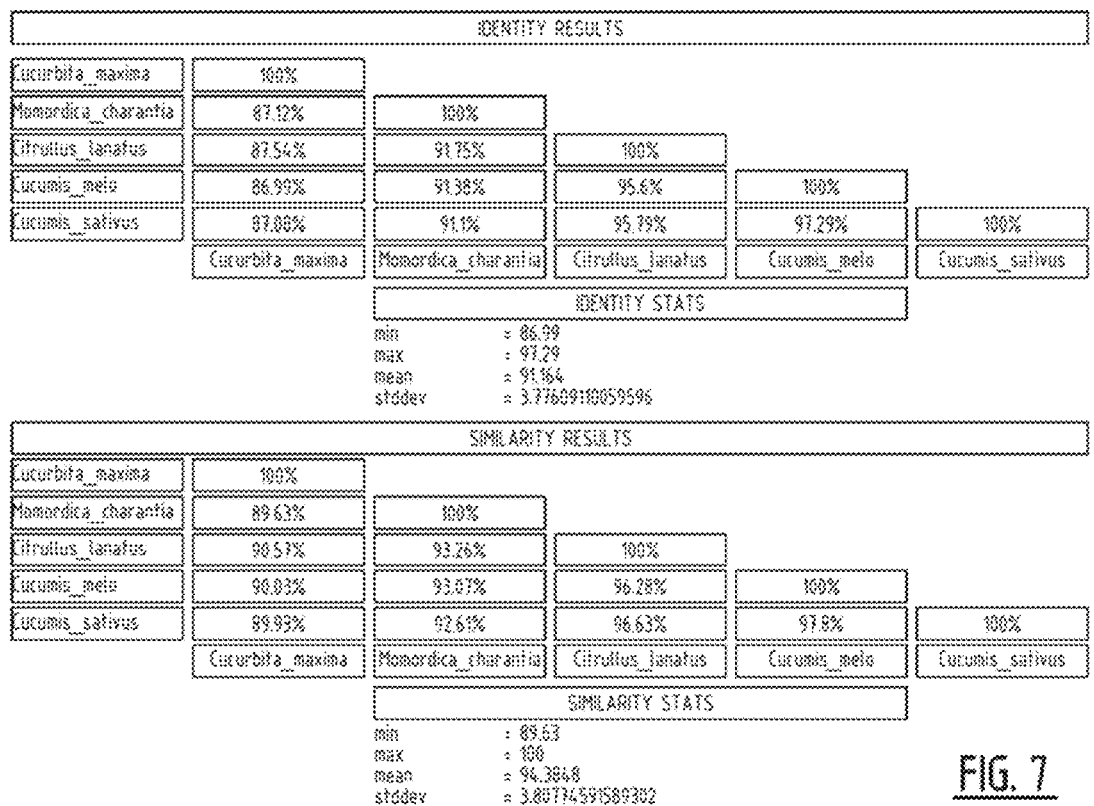

FIG. 7: Sequence identity and sequence similarity of the wild type CLAPR1 proteins of *Cucumis melo* (melon)—SEQ ID NO: 2; *Cucumis sativus* (cucumber)—SEQ ID NO: 6; *Momordica charantia* (bitter melon)—SEQ ID NO: 8; *Cucurbita maxima* (squash)—SEQ ID NO: 10; and *Citrullus lanatus* (watermelon)—SEQ ID NO: 12. Sequence identity is calculated using a method taking the gaps into account; sequence similarity is calculated based on grouping of amino acids having similar properties. See SIAS method for both options.

DETAILED DESCRIPTION OF THE INVENTION

Figure 1:
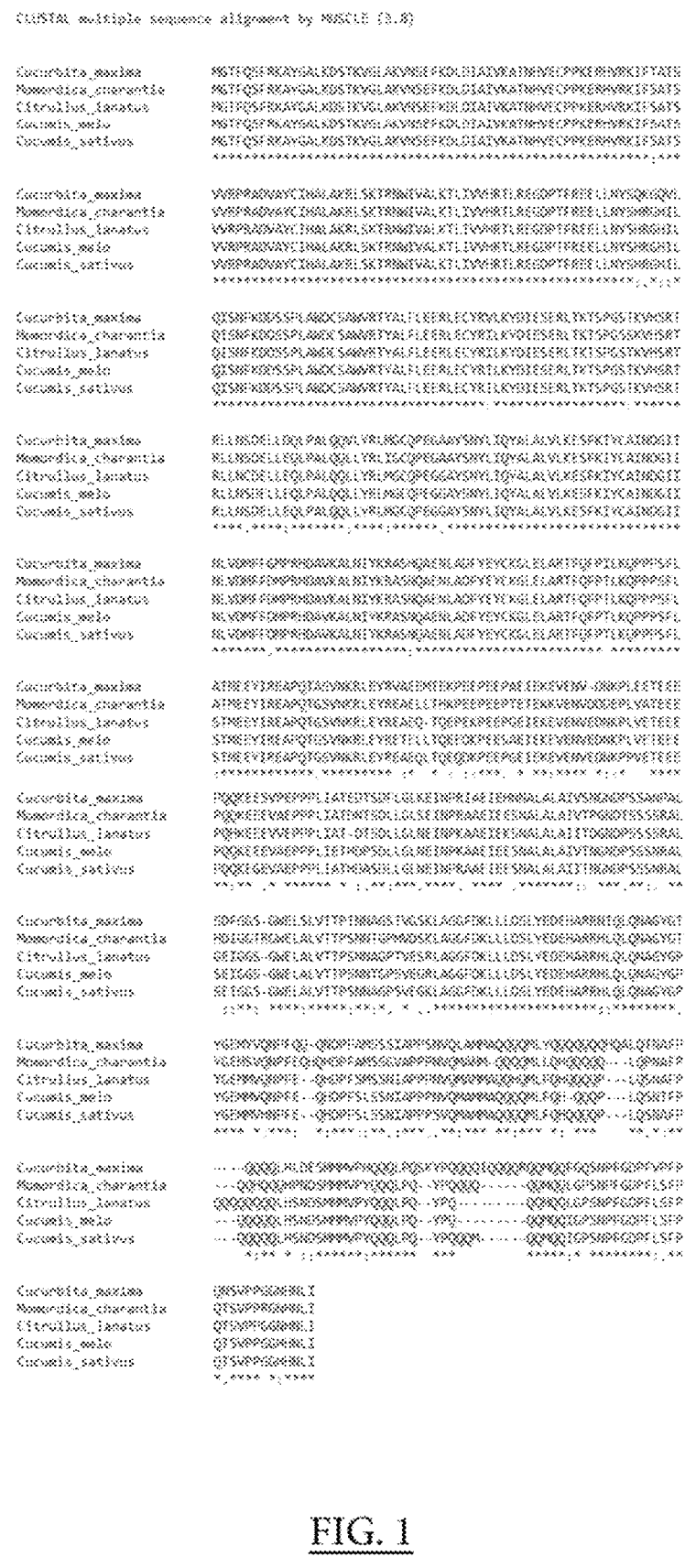

The present invention is thus broadly applicable to members of the Cucurbitaceae family that comprise a CLAPR1 gene and are naturally susceptible to CYSDV. The CLAPR1 genes in other species are herein referred to as "orthologs" or "orthologous" CLAPR1 genes. Identification of CLAPR1 orthologs can be performed in different crop species, methods of which are known in the art. In the present research, orthologs of the CLAPR1 gene were identified using a Basic Local Alignment Search Tool (BLAST) to compare the *Cucumis melo* CLAPR1 DNA (SEQ ID NO: 1) and protein sequence (SEQ ID NO: 2) with the genome of other Cucurbitaceae species. Using this method, 1-2 best hits per species were identified as candidate CLAPR1 orthologous genes. DNA and protein sequences of the CLAPR1 orthologs that were identified through this method are shown in Table 1, SEQ ID NOS: 5-12. Multiple sequence alignments (MSA) of the predicted protein sequences confirmed that these were orthologous CLAPR1 genes (FIG. 1). Furthermore, the wild type CLAPR1 protein of *Cucumis sativus* (cucumber), *Cucurbita maxima* (squash), *Momordica charantia* (bitter melon), and *Citrullus lanatus* (watermelon) has a high sequence identity and sequence similarity to the wild type CLAPR1 protein of *Cucumis melo* (melon) (FIG. 7).

Multiple sequence alignments (MSA) between orthologous CLAPR1 protein (FIG. 1) and functional analysis of the orthologous CLAPR1 protein sequences (InterProScan: Jones et al. (2014) Bioinformatics, 30(9): 1236-1240) revealed the protein's function, the protein families that the protein belongs to, and highly conserved domains that it contains. All CLAPR1 orthologs comprise an ENTH/VHS domain (IPR008942), Phosphoinositide-binding clathrin adaptor domain 2 (IPR014712), ENTH domain (IPR013809) and an AP180 N-terminal homology (ANTH) domain (IPR013809) (FIGS. 2-6). Based on these highly conserved signature domains, CLAPR1 is predicted to have a role in clathrin coat assembly (Gene Ontology Accession: GO:0048268).

Once the DNA sequence of the orthologous CLAPR1 genes are known, this information may be used to modulate or modify the expression of said genes by methods herein described.

The invention relates to a modified CLAPR1 gene that encodes a modified protein which may comprise one or more modifications, which modified protein leads to CYSDV resistance when present in a plant. This modified CLAPR1 gene is referred to herein as "the modified CLAPR1 gene of the invention".

The CYSDV resistance of the invention is controlled by modification(s) to the CLAPR1 gene, the inheritance of which is consistent with that of a monogenic recessive trait. The term "recessive trait" is to mean in the context of this application that the fully achievable trait is observed when the modified CLAPR1 gene is homozygously present in the genome such that both alleles of the CLAPR1 gene comprise the modification. When the modified CLAPR1 gene is heterozygously present in the genome, only one allele of the CLAPR1 gene is modified and therefore does not confer resistance to CYSDV. Since the inheritance of the trait is comparable to that of a monogenic trait, it is advantageous in that the trait can easily be incorporated into various plant types for a given plant species.

A "gene" in the context of this application may comprise exonic sequences and regulatory sequences such as a promotor sequence, and if present also may comprise intronic sequences. In this application the term "modification" or "modified" refers to a change in the sequence of the wild type CLAPR1 gene that results in an altered version of the wild type gene. A change or modification to the coding sequence of the gene and/or the regulatory sequences of the gene in turn leads to a change in the amino acid sequence of the encoded protein and/or the transcription of the gene, such that the resultant modified CLAPR1 protein has a reduced level, reduced activity or is completely absent as compared to the wild type protein. As used herein, "wild type" refers to the form of an organism, strain, gene, protein, characteristic or trait as it would occur in nature, and is in contrast to a mutated or modified form for example. As used herein, the "coding sequence" is the portion of the gene's DNA composed of exons that code for protein. Modifications to the gene when recessive are to be present in the homozygous state to be visible. Some of the modifications described herein are recessive and thus only confer CYSDV resistance in the homozygous form, however, the heterozygous form in which there is a modification to a single allele of the CLAPR1 gene, also forms part of this invention.

The modified CLAPR1 gene of the invention encodes a modified protein which may comprise one or more modifications in the wild type protein sequence of SEQ ID NO: 2 or in a protein sequence having at least 86% sequence identity to SEQ ID NO: 2, preferably 87%, 88%, 89%, 90%, 91%, 92%, 93%, 94%, 95%, 96%, 97%, 98%, or 99% sequence identity. The skilled person is familiar with methods for calculating sequence identity. Suitably sequence identity is calculated using the Sequence Identities and Similarities (SIAS) tool, which can be accessed at imed.med.ucm.es/Tools/sias.html. SIAS calculates pairwise sequence identity and sequence similarity from multiple sequence alignments. Sequence identity is calculated using a method taking the gaps into account; sequence similarity is calculated based on grouping of amino acids having similar properties. For calculations, default settings for SIM percentage, similarity amino acid grouping, sequence length, normalized similarity score, matrix and gap penalties are used.

The one or more modifications may be selected from an amino acid substitution, a premature stop codon, an insertion or deletion of one or more amino acids, or a combination thereof.

The DNA sequence of a gene may be altered in a number of ways, and will have varying effects depending on where the modification(s) occur and whether they alter the function of the encoded protein. Examples of such modifications include amino acid substitutions, premature stop codons, insertions, deletions, or frameshift mutations.

An insertion changes the number of DNA bases in a gene by adding a piece of DNA. A deletion changes the number of DNA bases by removing one or a few base pairs, or even an entire gene or neighboring genes. These types of modifications may alter the function of the resulting protein.

Frame shift mutations are caused by insertion or deletion of one or more base pairs in a DNA sequence encoding a protein. When the number of inserted or deleted base pairs at a certain position is not a multiple of 3, the triplet codon encoding the individual amino acids of the protein sequence become shifted relative to the original open reading frame, and then the encoded protein sequence changes dramatically. Protein translation will result in an entirely different amino acid sequence than that of the originally encoded protein, and often a frameshift can lead to a premature stop codon in the open reading frame. The overall result is that the encoded protein no longer has the same biological function as the originally encoded protein.

An amino acid substitution in an encoded protein sequence arises when the mutation of one or more base pairs in the coding sequence results in an altered triplet codon, often encoding a different amino acid. Due to the redundancy of the genetic code not all point mutations lead to amino acid changes. Such mutations are termed "silent mutations". Some amino acid changes are "conservative", i.e. they lead to the replacement of one amino acid by another amino acid with comparable properties, such that the mutation is unlikely to dramatically change the folding of the mature protein, or influence its function. Conservative amino acid substitutions may be made on the basis of chemical properties, for example similarity in polarity, charge, solubility, hydrophobicity, hydrophilicity or amphipathic nature of the residues, in which case the resulting protein may still function normally. Other amino acid changes are non-silent, non-conservative amino acid changes in domains that play a role in substrate recognition, the active site of enzymes, interaction domains or in major structural domains (such as transmembrane helices) may partly or completely destroy the functionality of an encoded protein, without thereby necessarily affecting the expression level of the encoding gene. As used herein, a "non-conservative amino acid change" occurs when there is an amino acid substitution at a well conserved or invariant position that is essential for the structure and/or function of the protein, or substitutions with amino acids that do not share conserved chemical properties (e.g. hydrophobic vs. charged vs. polar), which may lead to detrimental stability, functionality and/or structural effects of the encoded protein.

Mutations in the regulatory sequences such as the promotor sequence of a gene, may also perturb the biological function of the encoded protein, as such mutations may lead to a complete lack of transcription of the gene (e.g. subsequently resulting in a complete absence of the encoded protein), or to a significantly decreased and biologically inadequate level of transcription (e.g. subsequently resulting in a reduced level of the encoded protein). Mutations in splice sites may also perturb the biological function of the encoded protein, because if a splice site is destroyed by a mutation the amino acid sequence encoded in the mature mRNA transcribed from the gene will not be correct, and it may easily contain frame shifts and/or premature stop codons. In either case the protein sequence translated from such an mRNA will not be identical to the wild type protein sequence, which will most likely have serious consequences.

Any modification to the CLAPR1 gene that leads to a modified CLAPR1 protein having a reduced level, reduced activity or is completely absent as compared to the wild type protein is envisioned as part of this invention.

The presence of a modified CLAPR1 gene and/or modified CLAPR1 protein, optionally in isolated form, leading to CYSDV resistance may be detected using routine methods known to the skilled person such as RT-PCR, PCR, antibody-based assays, sequencing and genotyping assays, or combinations thereof. Such methods may be used to determine for example, a reduction or absence of the expression of the wild type CLAPR1 gene, a reduction or absence of the wild type CLAPR1 protein, the presence of a modified mRNA, cDNA or genomic DNA encoding a modified CLAPR1 protein, or the presence of a modified CLAPR1 protein, in plant material or plant parts, or DNA or RNA or protein derived therefrom.

In the course of the research that led to the present invention, an insertion was identified in the CLAPR1 gene of CYSDV resistant *Cucumis melo* plants. The nine base pair insertion starting at position c.1599_1600insCAGCAACAA in SEQ ID. No. 1 (the CAGCAACAA insertion is shown in SEQ ID NO: 3) encodes a modified protein which may comprise a three glutamine (Q) insertion at position p.533_534 insQQQ in SEQ ID. No. 2 (the QQQ insertion is shown in SEQ ID NO: 4). The 3Q insertion occurs in a polyQ tract of the encoded protein, causing its expansion.

The invention thus relates to a modified CLAPR1 gene, wherein the modified CLAPR1 gene encodes a modified protein which may comprise an insertion of at least one glutamine (Q), preferably three glutamines (Q). Alternatively or additionally, the modified CLAPR1 gene of the invention encodes a modified protein which may comprise one or more amino acid changes or a premature stop codon in its ENTH/VHS domain, ENTH domain, ANTH domain or Phosphoinositide binding clathrin adaptor domain 2.

In one embodiment the invention relates to a modified CLAPR1 gene, wherein the modified gene encodes a modified protein that may comprise an insertion of at least one glutamine (Q) at position p. 533_534insQ of SEQ ID NO: 2. Preferably, the modified protein may comprise three glutamine (Q) insertions at position p.533_534 insQQQ in SEQ ID. No. 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2. The modified protein provides resistance to CYSDV when present in a *Cucumis melo* plant.

In one embodiment the invention relates to a modified CLAPR1 gene, wherein the modified gene encodes a modified protein that may comprise an insertion of at least one glutamine (Q) at position p. 534_535insQ in SEQ ID NO: 6. Preferably, the modified protein may comprise three glutamine (Q) insertions at position p. 534_535insQQQ in SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6. The modified protein provides resistance to CYSDV when present in a *Cucumis sativus* plant.

In one embodiment the invention relates to a modified CLAPR1 gene, wherein the modified gene encodes a modified protein that may comprise an insertion of at least one glutamine (Q) at position p. 536_537insQ in SEQ ID NO: 8. Preferably, the modified protein may comprise three glutamine (Q) insertions at position p. 536_537insQQQ in SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8. The modified protein provides resistance to CYSDV when present in a *Momordica charantia* plant.

In one embodiment the invention relates to a modified CLAPR1 gene, wherein the modified gene encodes a modified protein that may comprise an insertion of at least one glutamine (Q) at position p. 537_538insQ in SEQ ID NO: 10. Preferably, the modified protein may comprise three glutamine (Q) insertions at position p. 537_538insQQQ in SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10. The modified protein provides resistance to CYSDV when present in a *Cucurbita maxima* plant.

In one embodiment the invention relates to a modified CLAPR1 gene, wherein the modified gene encodes a modified protein that may comprise an insertion of at least one glutamine (Q) at position p. 532_533insQ in SEQ ID NO: 12. Preferably, the modified protein may comprise three glutamine (Q) insertions at position p. 532_533insQQQ in SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12. The modified protein provides resistance to CYSDV when present in a *Citrullus lanatus* plant.

Such modifications or mutations of the CLAPR1 gene can be introduced randomly by means of one or more chemical compounds, such as ethyl methane sulphonate (EMS), nitrosomethylurea, hydroxylamine, proflavine, N-methly-N-nitrosoguanidine, N-ethyl-N-nitrosourea, N-methyl-N-nitronitrosoguanidine, diethyl sulphate, ethylene imine, sodium azide, formaline, urethane, phenol and ethylene oxide, and/or by physical means, such as UV-irradiation, fast neutron exposure, X-rays, gamma irradiation, and/or by insertion of genetic elements, such as transposons, T-DNA, retroviral elements.

Mutagenesis also may comprise the more specific, targeted introduction of at least one modification by means of homologous recombination, oligonucleotide-based mutation introduction, zinc-finger nucleases (ZFN), transcription activator-like effector nucleases (TALENs) or Clustered Regularly Interspaced Short Palindromic Repeat (CRISPR) systems.

Modifying a wild type CLAPR1 gene could also comprise the step of targeted genome editing, wherein the sequence of a wild type CLAPR1 gene is modified, or wherein a wild type CLAPR1 gene is replaced by another CLAPR1 gene that is optionally modified. This can be achieved by means of any method known in the art for modifying DNA in the genome of a plant, or by means of methods for gene replacement. Such methods include genome editing techniques and homologous recombination.

Homologous recombination allows the targeted insertion of a nucleic acid construct into a genome, and the targeting is based on the presence of unique sequences that flank the targeted integration site. For example, the wild type locus of a CLAPR1 gene could be replaced by a nucleic acid construct which may comprise a modified CLAPR1 gene.

Modifying a wild type CLAPR1 gene can involve inducing double strand breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered to make double-strand breaks at specific recognition sequences in the genome of a plant, another organism, or a host cell.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, Fok I. The unique, modular TAL effector DNA binding domain allows for the design of proteins with potentially any given DNA recognition specificity. Thus, the DNA binding domains of the TAL effector nucleases can be engineered to recognise specific DNA target sites and thus, used to make double-strand breaks at desired target sequences.

ZFNs can be used to make double-strand breaks at specific recognition sequences in the genome of a plant for gene modification or gene replacement through homologous recombination. The Zinc Finger Nuclease (ZFN) is a fusion protein which may comprise the part of the Fok I restriction endonuclease protein responsible for DNA cleavage and a zinc finger protein which recognizes specific, designed genomic sequences and cleaves the double-stranded DNA at those sequences, thereby producing free DNA ends (Urnov et al, 2010, *Nat. Rev. Genet.* 11:636-46; Carroll, 2011, *Genetics* 188:773-82).

The CRISPR/Cas nuclease system can also be used to make double-strand breaks at specific recognition sequences in the genome of a plant for gene modification or gene replacement through homologous recombination. The CRISPR/Cas nuclease system is an RNA-guided DNA endonuclease system performing sequence-specific double-stranded breaks in a DNA segment homologous to the designed RNA. It is possible to design the specificity of the sequence (Jinek et al, 2012, *Science* 337: 816-821; Cho et al, 2013, *Nat. Biotechnol.* 31:230-232; Cong et al, 2013, *Science* 339:819-823; Mali et al., 2013, *Science* 339:823-826; Feng et al, 2013, *Cell Res.* 23:1229-1232). Cas9 is an RNA-guided endonuclease that has the capacity to create double-stranded breaks in DNA in vitro and in vivo, also in eukaryotic cells. It is part of an RNA-mediated adaptive defence system known as Clustered Regularly Interspaced Short Palindromic Repeats (CRISPR) in bacteria and archaea. Cas9 gets sequence-specificity when it associates with a guide RNA molecule, which can target sequences present in an organism's DNA based on their sequence. Cas9 requires the presence of a Protospacer Adjacent Motif (PAM) immediately following the DNA sequence that is targeted by the guide RNA. The Cas9 enzyme has been first isolated from *Streptococcus pyogenes* (SpCas9), but functional homologues from many other bacterial species have been reported, such as *Neisseria meningitides, Treponema denticola, Streptococcus thermophilus, Francisella novicida, Staphylococcus aureus*, etcetera. For SpCas9, the PAM sequence is 5'-NGG-3', whereas various Cas9 proteins from other bacteria have been shown to recognise different PAM sequences. In nature, the guide RNA is a duplex between crRNA and tracrRNA, but a single guide RNA (sgRNA) molecule which may comprise both crRNA and tracrRNA has been shown to work equally well (Jinek et al, 2012, *Science* 337: 816-821). The advantage of using an sgRNA is that it reduces the complexity of the CRISPR-Cas9 system down to two components, instead of three. For use in an experimental setup (in vitro or in vivo) this is an important simplification.

An alternative for Cas9 is, for example, Cpf1, which does not need a tracrRNA to function, which recognises a different PAM sequence, and which creates sticky end cuts in the DNA, whereas Cas9 creates blunt ends.

On the one hand, genetic modification techniques can be applied to express a site-specific nuclease, such as an RNA-guided endonuclease and/or guide RNAs, in eukaryotic cells. One or more DNA constructs encoding an RNA-guided endonuclease and at least one guide RNA can be introduced into a cell or organism by means of stable transformation (wherein the DNA construct is integrated into the genome) or by means of transient expression (wherein the DNA construct is not integrated into the genome, but it expresses an RNA-guided endonuclease and at least one guide RNA in a transient manner). This approach requires the use of a transformation vector and a suitable promoter for expression in said cell or organism. Organisms into which foreign DNA has been introduced are considered to be Genetically Modified Organisms (GMOs), and the same applies to cells derived therefrom and to offspring of these organisms. In important parts of the worldwide food market, transgenic food is not allowed for human consumption, and not appreciated by the public. There is however also an alternative, "DNA-free" delivery method of CRISPR-Cas components into intact plants, that does not involve the introduction of DNA constructs into the cell or organism.

For example, introducing the mRNA encoding Cas9 into a cell or organism has been described, after in vitro transcription of said mRNA from a DNA construct encoding an RNA-guided endonuclease, together with at least one guide RNA. This approach does not require the use of a transformation vector and a suitable promoter for expression in said cell or organism.

Another known approach is the in vitro assembly of ribonucleoprotein (RNP) complexes, which may comprise an RNA-guided endonuclease protein (for example Cas9) and at least one guide RNA, and subsequently introducing the RNP complex into a cell or organism. In animals and animal cell and tissue cultures, RNP complexes have been introduced by means of, for example, injection, electroporation, nanoparticles, vesicles, and with the help of cell-penetrating peptides. In plants, the use of RNPs has been demonstrated in protoplasts, for example with polyethylene glycol (PEG) transfection (Woo et al, 2015, *Nat. Biotech.* 33: 1162-1164). After said modification of a genomic sequence has taken place, the protoplasts or cells can be used to produce plants that harbour said modification in their genome, using any plant regeneration method known in the art (such as in vitro tissue culture).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

In the context of this application, the "trait of the invention" as used herein is CYSDV resistance as a result of the presence of a modified CLAPR1 gene and/or a modified CLAPR1 protein. "Trait of the invention", "trait", or "phenotypic trait", may be used interchangeably.

Based on differences in CYSDV symptoms presenting on plants exposed to CYSDV infection, a skilled person is able to visually assess symptoms and relate the symptoms or a lack thereof, to whether a plant is resistant or susceptible to CYSDV. For example, CYSDV symptoms on melon plants are described in Table 2, when measured under the conditions as described in Example 1. In general, melon plants exhibiting the trait of the invention (e.g. CYSDV resistance) present no symptoms or minimal virus symptoms such as subtle localized yellow spotting in one part of the leaves and an otherwise healthy plant character. In contrast, a melon plant that is susceptible to CYSDV will in general present severe virus symptoms on one or more leaves including: yellow interveinal chlorosis while veins remain relatively green, leaf curling, and/or fragile leaves.

The modified CLAPR1 gene of the invention as herein described, encodes a modified protein which may comprise one or more modifications. The invention thus also relates to a modified CLAPR1 protein. This modified CLAPR1 protein is also referred to herein as the "modified protein of the invention" and as a result of the one or more modifications, provides resistance to CYSDV when present in a plant.

In one embodiment, the modified CLAPR1 protein of the invention may comprise an insertion of at least one glutamine (Q) at position p. 533_534insQ of SEQ ID NO: 2. Preferably, the modified protein may comprise three glutamine (Q) insertions at position p.533_534insQQQ in SEQ ID. No. 2. Alternatively or additionally, the modified protein of the invention may comprise one or more amino acid changes or a premature stop codon in its ENTH/VHS domain, ENTH domain, ANTH domain or Phosphoinositide binding clathrin adaptor domain 2 in SEQ ID NO: 2. The modified protein of the invention provides resistance to CYSDV when present in a *Cucumis melo* plant.

In one embodiment, the modified CLAPR1 protein of the invention may comprise an insertion of at least one glutamine (Q) at position p. 534_535insQ in SEQ ID NO: 6. Preferably, the modified protein may comprise three glutamine (Q) insertions at position p. 534_535insQQQ in SEQ ID NO: 6. Alternatively or additionally, the modified protein of the invention may comprise one or more amino acid changes or a premature stop codon in its ENTH/VHS domain, ENTH domain, ANTH domain or Phosphoinositide binding clathrin adaptor domain 2 in SEQ ID NO: 6. The modified protein of the invention provides resistance to CYSDV when present in a *Cucumis sativus* plant.

In one embodiment, the modified CLAPR1 protein of the invention may comprise an insertion of at least one glutamine (Q) at position p. 536_537insQ in SEQ ID NO: 8. Preferably, the modified protein may comprise three glutamine (Q) insertions at position p. 536_537insQQQ in SEQ ID NO: 8. Alternatively or additionally, the modified protein of the invention may comprise one or more amino acid changes or a premature stop codon in its ENTH/VHS domain, ENTH domain, ANTH domain or Phosphoinositide binding clathrin adaptor domain 2 in SEQ ID NO: 8. The modified protein provides resistance to CYSDV when present in a *Momordica charantia* plant.

In one embodiment the invention relates to a modified CLAPR1 protein, wherein the modified protein may comprise an insertion of at least one glutamine (Q) at position p. 537_538insQ in SEQ ID NO: 10. Preferably, the modified protein may comprise three glutamine (Q) insertions at position p. 537_538insQQQ in SEQ ID NO: 10. Alternatively or additionally, the modified protein of the invention may comprise one or more amino acid changes or a premature stop codon in its ENTH/VHS domain, ENTH domain, ANTH domain or Phosphoinositide binding clathrin adaptor domain 2 in SEQ ID NO: 10. The modified protein of the invention provides resistance to CYSDV when present in a *Cucurbita maxima* plant.

In one embodiment the invention relates to a modified CLAPR1 protein, wherein the modified protein may comprise an insertion of at least one glutamine (Q) at position p. 532_533insQ in SEQ ID NO: 12. Preferably, the modified protein of the invention may comprise three glutamine (Q) insertions at position p. 532_533insQQQ in SEQ ID NO: 12. Alternatively or additionally, the modified protein may comprise one or more amino acid changes or a premature stop codon in its ENTH/VHS domain, ENTH domain, ANTH domain or Phosphoinositide binding clathrin adaptor domain 2 in SEQ ID NO: 12. The modified protein provides resistance to CYSDV when present in a *Citrullus lanatus* plant.

The invention also relates to a plant which may comprise in its genome the modified CLAPR1 gene of the invention. This plant is referred to herein as a "plant of the invention". A plant of the invention can comprise the modified CLAPR1 gene of the invention heterozygously, in which case the plant is not resistant to CYSDV but is useful for transferring the modified CLAPR1 gene of the invention to another plant. A plant of the invention can also comprise the modified CLAPR1 gene of the invention homozygously, in which case the plant is resistant to CYSDV. A plant of the invention can be a plant of an inbred line, a hybrid, a doubled haploid or a plant of a segregating population. Preferably the plant of the invention is non-transgenic.

In one embodiment, the plant of the invention is a melon plant (*Cucumis melo*), which may comprise in its genome the modified CLAPR1 gene of the invention, wherein the modified CLAPR1 gene encodes a modified protein which may comprise one or more modifications in the wild type protein sequence of SEQ ID NO: 2. This plant is also referred to herein as a "melon plant (*Cucumis melo*) of the invention". If the melon plant of the invention may comprise the modified CLAPR1 gene of the invention homozygously, the plant is resistant to CYSDV as a result of the presence of the modified protein.

Preferably, the melon (*Cucumis melo*) plant of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534 insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2.

The modified CLAPR1 gene encoding a modified protein which may comprise an insertion of three glutamines (Q) at position p.533_534 insQQQ of SEQ ID NO: 2 is homozygously present in a plant grown from a seed deposited under NCIMB accession number 42992.

The phrase "present in" may also mean "found in" or "contained in" or "obtainable from" (the genome of) plants grown from seeds of the deposit or the deposited seeds themselves. The phrases are intended to indicate that the modified CLAPR1 gene of the invention is the same or essentially the same as the modified CLAPR1 gene in the genome of the deposited material. "Essentially the same" means that the sequence of the modified CLAPR1 gene need not be identical in sequence but has in any case to perform the same function in causing the resistance to CYSDV. In other words, the modified CLAPR1 gene may comprise polymorphisms (i.e. variation in the sequence) as compared to the modified CLAPR1 gene of the invention but these polymorphisms do not have any bearing on the function of the modified CLAPR1 gene in causing the resistance phenotype. For example, polymorphic SNPs in the CLAPR1 gene were identified through sequencing of various melon lines, at positions c.513T>C, c.651C>T, and c.1767T>C but these changes are expected to result in synonymous changes in the encoded protein at p.Pro171Pro, p.Ile217Ile, and p.His589His respectively, and do not correlate with CYSDV resistance. A polymorphic SNP was also identified at c.1024G>C in the CLAPR1 gene leading to a non-synonymous amino acid change at position p.Glu342Gln in the encoded protein, but this modification also did not correlate with CYSDV resistance.

In one embodiment, the plant of the invention is a cucumber plant (*Cucumis sativus*), which may comprise in its genome the modified CLAPR1 gene of the invention, wherein the modified CLAPR1 gene encodes a modified protein which may comprise one or more modifications in the wild type protein sequence of SEQ ID NO: 6. This plant is also referred to herein as a "cucumber plant (*Cucumis sativus*) of the invention". If the cucumber plant of the invention may comprise the modified CLAPR1 gene of the invention homozygously, the plant is resistant to CYSDV as a result of the presence of the modified protein.

Preferably, the cucumber (*Cucumis sativus*) plant of the invention may comprise in its genome a modified CLAPR1 gene, wherein the modified CLAPR1 gene encodes a modified protein which may comprise an insertion of at least one glutamine (Q) at position p. 534_535insQ of SEQ ID NO: 6. More preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the plant of the invention is a bitter melon plant (*Momordica charantia*), which may comprise in its genome the modified CLAPR1 gene of the invention, wherein the modified CLAPR1 gene encodes a modified protein which may comprise one or more modifications in the wild type protein sequence of SEQ ID NO: 8. This plant is also referred to herein as a "bitter melon plant (*Momordica charantia*) of the invention". If the bitter melon plant of the invention may comprise the modified CLAPR1 gene of the invention homozygously, the plant is resistant to CYSDV as a result of the presence of the modified protein.

Preferably, the bitter melon plant (*Momordica charantia*) plant of the invention may comprise in its genome a modified CLAPR1 gene, wherein the modified CLAPR1 gene encodes a modified protein which may comprise an insertion of at least one glutamine (Q) at position p. 536_537insQ of SEQ ID NO: 8. More preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the plant of the invention is a squash plant (*Cucurbita maxima*), which may comprise in its genome the modified CLAPR1 gene of the invention, wherein the modified CLAPR1 gene encodes a modified protein which may comprise one or more modifications in the wild type protein sequence of SEQ ID NO: 10. This plant is also referred to herein as a "squash plant (*Cucurbita maxima*) of the invention". If the squash plant of the invention may comprise the modified CLAPR1 gene of the invention homozygously, the plant is resistant to CYSDV as a result of the presence of the modified protein.

Preferably, the squash (*Cucurbita maxima*) plant of the invention may comprise in its genome a modified CLAPR1 gene, wherein the modified CLAPR1 gene encodes a modified protein which may comprise an insertion of at least one glutamine (Q) at p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the plant of the invention is a watermelon plant (*Citrullus lanatus*), which may comprise in its genome the modified CLAPR1 gene of the invention, wherein the modified CLAPR1 gene encodes a modified protein which may comprise one or more modifications in the wild type protein sequence of SEQ ID NO: 12. This plant is also referred to herein as a "watermelon plant (*Citrullus lanatus*) of the invention". If the watermelon plant of the invention may comprise the modified CLAPR1 gene of the invention homozygously, the plant is resistant to CYSDV as a result of the presence of the modified protein.

Preferably, the watermelon (*Citrullus lanatus*) plant of the invention may comprise in its genome a modified CLAPR1 gene, wherein the modified CLAPR1 gene encodes a modified protein which may comprise an insertion of at least one glutamine (Q) at p. 532_533insQ of SEQ ID NO: 12. More preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention also encompasses a seed which may comprise the modified CLAPR1 gene of the invention. The seed as described is also referred herein as "the seed of the invention". A plant grown from this seed may comprise the modified CLAPR1 gene of the invention and is thus a plant of the invention. The invention also relates to seeds produced by a plant of the invention. These seeds comprise a modified CLAPR1 gene, and as such, a plant grown from said seed is a plant of the invention. If the plant of the invention grown from this seed may comprise the modified CLAPR1 gene of the invention homozygously, the plant is resistant to CYSDV as a result of the presence of the modified protein.

In one embodiment, the seed of the invention is a melon seed (*Cucumis melo*) which may comprise in its genome the modified CLAPR1 gene of the invention, wherein the modified CLAPR1 gene encodes a modified protein which may comprise one or more modifications in the wild type protein sequence of SEQ ID NO: 2. This seed is also referred to herein as a "melon seed (*Cucumis melo*) of the invention". If the melon seed of the invention may comprise the modified CLAPR1 gene of the invention homozygously, the plant grown from the seed is resistant to CYSDV.

Preferably, the melon seed (*Cucumis melo*) of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2. Representative seed which may comprise a modified CLAPR1 gene that encodes a modified protein which may comprise an insertion of three glutamines (Q) at position p.533_534insQQQ of SEQ ID NO: 2 has been deposited under NCIMB accession number 42992.

In one embodiment, the seed of the invention is a cucumber seed (*Cucumis sativus*) which may comprise in its genome the modified CLAPR1 gene of the invention, wherein the modified CLAPR1 gene encodes a modified protein which may comprise one or more modifications in the wild type protein sequence of SEQ ID NO: 6. This seed is also referred to herein as a "cucumber seed (*Cucumis sativus*) of the invention". If the cucumber seed of the invention may comprise the modified CLAPR1 gene of the invention homozygously, the plant grown from the seed is resistant to CYSDV.

Preferably, the cucumber seed may comprise in its genome a modified CLAPR1 gene, wherein the modified CLAPR1 gene encodes a modified protein which may comprise an insertion of at least one glutamine (Q) at position p. 534_535insQ of SEQ ID NO: 6. More preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the seed of the invention is a bitter melon seed (*Momordica charantia*), which may comprise in its genome the modified CLAPR1 gene of the invention, wherein the modified CLAPR1 gene encodes a modified protein which may comprise one or more modifications in the wild type protein sequence of SEQ ID NO: 8. This seed is also referred to herein as a "bitter melon seed (*Momordica charantia*) of the invention". If the bitter melon seed of the invention may comprise the modified CLAPR1 gene of the invention homozygously, the plant grown form the seed is resistant to CYSDV as a result of the presence of the modified protein.

Preferably, the bitter melon seed (*Momordica charantia*) of the invention may comprise in its genome a modified CLAPR1 gene, wherein the modified CLAPR1 gene encodes a modified protein which may comprise an insertion of at least one glutamine (Q) at position p. 536_537insQ of SEQ ID NO: 8. More preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the seed of the invention is a squash seed (*Cucurbita maxima*), which may comprise in its genome the modified CLAPR1 gene of the invention, wherein the modified CLAPR1 gene encodes a modified protein which may comprise one or more modifications in the wild type protein sequence of SEQ ID NO: 10. This seed is also referred to herein as a "squash seed (*Cucurbita maxima*) of the invention". If the squash seed of the invention may comprise the modified CLAPR1 gene of the invention homozygously, the plant grown from the seed is resistant to CYSDV as a result of the presence of the modified protein.

Preferably, the squash (*Cucurbita maxima*) seed of the invention may comprise in its genome a modified CLAPR1 gene, wherein the modified CLAPR1 gene encodes a modified protein which may comprise an insertion of at least one glutamine (Q) at p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the seed of the invention is a watermelon seed (*Citrullus lanatus*), which may comprise in its genome the modified CLAPR1 gene of the invention, wherein the modified CLAPR1 gene encodes a modified protein which may comprise one or more modifications in the wild type protein sequence of SEQ ID NO: 12. This seed is also referred to herein as a "watermelon seed (*Citrullus lanatus*) of the invention". If the watermelon seed of the invention may comprise the modified CLAPR1 gene of the invention homozygously, the plant grown from the seed is resistant to CYSDV as a result of the presence of the modified protein.

Preferably, the watermelon (*Citrullus lanatus*) seed of the invention may comprise in its genome a modified CLAPR1 gene, wherein the modified CLAPR1 gene encodes a modified protein which may comprise an insertion of at least one glutamine (Q) at p. 532_533insQ of SEQ ID NO: 12. More preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention further relates to progeny of the plants, cells, tissues and seeds of the invention, which progeny may comprise a modified CLAPR1 gene that leads to CYSDV resistance. Such progeny can in itself be plants, cells, tissues or seeds.

"Progeny" or "progeny plant of the invention" also encompass plants that comprise a modified CLAPR1 gene of the invention as herein described, and are obtained from other plants, or progeny of plants by vegetative propagation or multiplication or are plants grown from the seed of the invention. Progeny of the invention comprise a modified CLAPR1 gene in their genomes and exhibit resistance to CYSDV. As used herein "progeny" is intended to mean the first and all further descendants from a cross with a plant of the invention.

In one embodiment, the progeny plant is a progeny plant of the melon plant (*Cucumis melo*) of the invention or a progeny plant grown from the melon seed (*Cucumis melo*) of the invention, which may comprise in its genome a modified CLAPR1 gene of the invention, wherein the modified CLAPR1 gene encodes a modified protein which may comprise one or more modifications in the wild type protein sequence of SEQ ID NO: 2. This progeny plant is also referred to herein as a "melon progeny plant (*Cucumis melo*) of the invention". If the melon progeny plant of the invention may comprise the modified CLAPR1 gene of the invention homozygously, the plant is resistant to CYSDV as a result of the presence of the modified protein.

Preferably, the melon progeny plant (*Cucumis melo*) of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2.

In one embodiment, the progeny plant is a progeny plant of the cucumber plant (*Cucumis sativus*) of the invention or a progeny plant grown from a cucumber seed (*Cucumis sativus*) of the invention, which may comprise in its genome the modified CLAPR1 gene of the invention, wherein the modified CLAPR1 gene encodes a modified protein which may comprise one or more modifications in the wild type protein sequence of SEQ ID NO: 6. This progeny plant is also referred to herein as a "cucumber progeny plant (*Cucumis sativus*) of the invention". If the cucumber progeny plant of the invention may comprise the modified CLAPR1 gene of the invention homozygously, the plant is resistant to CYSDV as a result of the presence of the modified protein.

Preferably, the cucumber progeny plant of the invention may comprise in its genome a modified CLAPR1 gene, wherein the modified CLAPR1 gene encodes a modified protein which may comprise an insertion of at least one glutamine (Q) at position p. 534_535insQ of SEQ ID NO: 6. More, preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the progeny plant is a progeny plant of the bitter melon plant (*Momordica charantia*) of the invention or a progeny plant grown from the bitter melon seed (*Momordica charantia*) of the invention, which may comprise in its genome the modified CLAPR1 gene of the invention, wherein the modified CLAPR1 gene encodes a modified protein which may comprise one or more modifications in the wild type protein sequence of SEQ ID NO: 8. This plant is also referred to herein as a "bitter melon progeny plant (*Momordica charantia*) of the invention". If the bitter melon progeny plant of the invention may comprise the modified CLAPR1 gene of the invention homozygously, the plant is resistant to CYSDV as a result of the presence of the modified protein.

Preferably, the bitter melon progeny plant of the invention may comprise in its genome a modified CLAPR1 gene, wherein the modified CLAPR1 gene encodes a modified protein which may comprise an insertion of at least one glutamine (Q) at p. 536_537insQ of SEQ ID NO: 8. More preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the progeny plant is a progeny plant of the squash plant (*Cucurbita maxima*) of the invention or a progeny plant grown from the squash seed (*Cucurbita maxima*) of the invention, which may comprise in its genome the modified CLAPR1 gene of the invention, wherein the modified CLAPR1 gene encodes a modified protein which may comprise one or more modifications in the wild type protein sequence of SEQ ID NO: 10. This progeny plant is also referred to herein as a "squash progeny plant (*Cucurbita maxima*) of the invention". If the squash progeny plant of the invention may comprise the modified CLAPR1 gene of the invention homozygously, the plant is resistant to CYSDV as a result of the presence of the modified protein.

Preferably, the squash progeny plant of the invention which is resistant to CYSDV, may comprise in its genome a modified CLAPR1 gene, wherein the modified CLAPR1 gene encodes a modified protein which may comprise an insertion of at least one glutamine (Q) at p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the progeny plant is a progeny plant of the watermelon plant (*Citrullus lanatus*) of the invention or a progeny plant grown from the watermelon seed (*Citrullus lanatus*), which may comprise in its genome the modified CLAPR1 gene of the invention, wherein the modified CLAPR1 gene encodes a modified protein which may comprise one or more modifications in the wild type protein sequence of SEQ ID NO: 12. This plant is also referred to herein as a "watermelon progeny plant (*Citrullus lanatus*) of the invention". If the watermelon progeny plant of the invention may comprise the modified CLAPR1 gene of the invention homozygously, the plant is resistant to CYSDV as a result of the presence of the modified protein.

Preferably, the watermelon progeny plant of the invention which is resistant to CYSDV, may comprise in its genome a modified CLAPR1 gene, wherein the modified CLAPR1 gene encodes a modified protein which may comprise an insertion of at least one glutamine (Q) at p. 532_533insQ of SEQ ID NO: 12. More preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

CYSDV infection leads to reduced fruit yield and reduced fruit quality. For example in melons, CYSDV infection causes a reduction in the BRIX content in the harvested melon fruit, leading to unmarketable melons.

The invention thus also relates to a fruit harvested from a plant of the invention or from a plant grown from a seed of the invention. This fruit is referred herein as a "fruit of the invention" and may comprise the modified CLAPR1 gene of the invention.

In one embodiment, the fruit of the invention is a melon fruit, which may comprise in its genome a modified CLAPR1 gene of the invention, wherein the modified CLAPR1 gene encodes a modified protein which may comprise one or more modifications in the wild type protein sequence of SEQ ID NO: 2. This melon fruit is referred herein as "the melon fruit of the invention". If the melon fruit of the invention may comprise the modified CLAPR1 gene of the invention homozygously, the fruit is resistant to CYSDV as a result of the presence of the modified protein and thus the fruit has normal fruit characteristics that are agronomically acceptable. The seeds of this fruit also comprise the modified CLAPR1 gene of the invention and therefore also form a part of the invention.

Preferably, the melon fruit of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2.

In one embodiment, the fruit of the invention is a cucumber fruit, which may comprise in its genome a modified CLAPR1 gene of the invention, wherein the modified CLAPR1 gene encodes a modified protein which may comprise one or more modifications in the wild type protein sequence of SEQ ID NO: 6. This cucumber fruit is referred herein as "the cucumber fruit of the invention". If the cucumber fruit of the invention may comprise the modified CLAPR1 gene of the invention homozygously, the fruit is resistant to CYSDV as a result of the presence of the modified protein and thus the fruit has normal fruit characteristics that are agronomically acceptable. The seeds of this fruit also comprise the modified CLAPR1 gene of the invention and therefore also form a part of the invention.

Preferably, the cucumber fruit of the invention may comprise in its genome a modified CLAPR1 gene, wherein the modified CLAPR1 gene encodes a modified protein which may comprise an insertion of at least one glutamine (Q) at position p. 534_535insQ of SEQ ID NO: 6. More preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the fruit of the invention is a bitter melon fruit, which may comprise in its genome a modified CLAPR1 gene of the invention, wherein the modified CLAPR1 gene encodes a modified protein which may comprise one or more modifications in the wild type protein sequence of SEQ ID NO: 8. This bitter melon fruit is referred herein as "the bitter melon fruit of the invention". If the bitter melon fruit of the invention may comprise the modified CLAPR1 gene of the invention homozygously, the fruit is resistant to CYSDV as a result of the presence of the modified protein and thus the fruit has normal fruit characteristics that are agronomically acceptable. The seeds of this fruit also comprise the modified CLAPR1 gene of the invention and therefore also form a part of the invention.

Preferably, the bitter melon fruit of the invention may comprise in its genome a modified CLAPR1 gene, wherein the modified CLAPR1 gene encodes a modified protein which may comprise an insertion of at least one glutamine (Q) at p. 536_537insQ of SEQ ID NO: 8. More preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the fruit of the invention is a squash fruit, which may comprise in its genome a modified CLAPR1 gene of the invention, wherein the modified CLAPR1 gene encodes a modified protein which may comprise one or more modifications in the wild type protein sequence of SEQ ID NO: 10. This squash fruit is referred herein as "the squash fruit of the invention". If the squash fruit of the invention may comprise the modified CLAPR1 gene of the invention homozygously, the fruit is resistant to CYSDV as a result of the presence of the modified protein and thus the fruit has normal fruit characteristics that are agronomically acceptable. The seeds of this fruit also comprise the modified CLAPR1 gene of the invention and therefore also form a part of the invention.

Preferably, the squash fruit of the invention may comprise in its genome a modified CLAPR1 gene, wherein the modified CLAPR1 gene encodes a modified protein which may comprise an insertion of at least one glutamine (Q) at p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the fruit of the invention is a watermelon fruit, which may comprise in its genome a modified CLAPR1 gene of the invention, wherein the modified CLAPR1 gene encodes a modified protein which may comprise one or more modifications in the wild type protein sequence of SEQ ID NO: 12. This watermelon fruit is referred herein as "the watermelon fruit of the invention". If the watermelon fruit of the invention may comprise the modified CLAPR1 gene of the invention homozygously, the fruit is resistant to CYSDV as a result of the presence of the modified protein and thus the fruit has normal fruit characteristics that are agronomically acceptable. The seeds of this fruit also comprise the modified CLAPR1 gene of the invention and therefore also form a part of the invention.

Preferably, the watermelon fruit of the invention may comprise in its genome a modified CLAPR1 gene, wherein the modified CLAPR1 gene encodes a modified protein which may comprise an insertion of at least one glutamine (Q) at p. 532_533insQ of SEQ ID NO: 12. Preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention further relates to a food product or processed food product which may comprise the fruit of the invention or part thereof. The food product may have undergone one or more processing steps. Such a processing step might comprise but is not limited to any one of the following treatments or combinations thereof: peeling, cutting, washing, juicing, cooking, cooling or preparing a salad mixture which may comprise the fruit of the invention. The processed form that is obtained is also part of this invention.

The invention further relates to a cell of a plant of the invention. Such a cell may either be in isolated form or a part of the complete plant or parts thereof and still constitutes a cell of the invention because such a cell harbours the genetic information that leads to the resistance to CYSDV of a plant of the invention. Each cell of a plant of the invention carries the genetic information that leads to CYSDV resistance. A cell of the invention may also be a regenerable cell that can regenerate into a new plant of the invention. The presence of genetic information as used herein is the presence of a modified CLAPR1 gene as defined herein.

In one embodiment, the cell of the invention is a melon cell (*Cucumis melo*), which may comprise in its genome a modified CLAPR1 gene of the invention, wherein the modified CLAPR1 gene encodes a modified protein which may comprise one or more modifications in the wild type protein sequence of SEQ ID NO: 2. This melon cell is referred herein as a "melon cell (*Cucumis melo*) of the invention". The melon cell of the invention provides genetic information that leads to CYSDV resistance.

Preferably, the melon cell of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2.

In one embodiment, the cell of the invention is a cucumber cell (*Cucumis sativus*), which may comprise in its genome the modified CLAPR1 gene of the invention, wherein the modified CLAPR1 gene encodes a modified protein which may comprise one or more modifications in the wild type protein sequence of SEQ ID NO: 6. This cucumber cell is also referred to herein as a "cucumber cell (*Cucumis sativus*) of the invention". The cucumber cell of the invention provides genetic information that leads to CYSDV resistance.

Preferably, the cucumber cell of the invention may comprise in its genome a modified CLAPR1 gene, wherein the modified CLAPR1 gene encodes a modified protein which may comprise an insertion of at least one glutamine (Q) at position p. 534_535insQ of SEQ ID NO: 6. More preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the cell of the invention is a bitter melon cell (*Momordica charantia*), which may comprise in its genome the modified CLAPR1 gene of the invention, wherein the modified CLAPR1 gene encodes a modified protein which may comprise one or more modifications in the wild type protein sequence of SEQ ID NO: 8. This bitter melon cell is also referred to herein as a "bitter melon cell (*Momordica charantia*) of the invention". The bitter melon cell of the invention provides genetic information that leads to CYSDV resistance.

Preferably, the bitter melon cell of the invention may comprise in its genome a modified CLAPR1 gene, wherein the modified CLAPR1 gene encodes a modified protein which may comprise an insertion of at least one glutamine (Q) at p. 536_537insQ of SEQ ID NO: 8. More, preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the cell of the invention is a squash cell (*Cucurbita maxima*), which may comprise in its genome the modified CLAPR1 gene of the invention, wherein the modified CLAPR1 gene encodes a modified protein which may comprise one or more modifications in the wild type protein sequence of SEQ ID NO: 10. This squash cell is also referred to herein as a "squash cell (*Cucurbita maxima*) of the invention". The squash cell of the invention provides genetic information that leads to CYSDV resistance.

Preferably, the squash cell of the invention may comprise in its genome a modified CLAPR1 gene, wherein the modified CLAPR1 gene encodes a modified protein which may comprise an insertion of at least one glutamine (Q) at p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the cell of the invention is a watermelon cell (*Citrullus lanatus*), which may comprise in its genome the modified CLAPR1 gene of the invention, wherein the modified CLAPR1 gene encodes a modified protein which may comprise one or more modifications in the wild type protein sequence of SEQ ID NO: 12. This watermelon cell is also referred to herein as a "watermelon cell (*Citrullus lanatus*) of the invention". The watermelon cell of the invention provides genetic information that leads to CYSDV resistance.

Preferably, the watermelon cell of the invention may comprise in its genome a modified CLAPR1 gene, wherein the modified CLAPR1 gene encodes a modified protein which may comprise an insertion of at least one glutamine (Q) at p. 532_533insQ of SEQ ID NO: 12. More, preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention further relates to a tissue culture of a plant of the invention, wherein the tissue culture may comprise the modified CLAPR1 gene of the invention that leads to the CYSDV resistance of the invention. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant which may comprise the modified CLAPR1 gene, wherein the regenerated plant expresses the CYSDV resistance of the invention. The regenerated plant is also part of the invention.

In one embodiment, the invention relates to a tissue culture of a melon plant of the invention, wherein the tissue culture may comprise a modified CLAPR1 gene that encodes a modified protein which may comprise one or more modifications in the wild type protein sequence of SEQ ID NO: 2. This melon tissue culture is referred herein as a "melon tissue culture (*Cucumis melo*) of the invention". The melon tissue culture of the invention provides genetic information that leads to CYSDV resistance. Preferably, the melon tissue culture of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 2.

In one embodiment, the invention relates to a tissue culture of a cucumber plant of the invention, wherein the tissue culture may comprise a modified CLAPR1 gene that encodes a modified protein which may comprise one or more modifications in the wild type protein sequence of SEQ ID NO: 6. This cucumber tissue culture is referred herein as a "cucumber tissue culture (*Cucumis sativus*) of the invention". The cucumber tissue culture of the invention provides genetic information that leads to CYSDV resistance.

Preferably, the tissue culture of the invention may comprise in its genome a modified CLAPR1 gene, wherein the modified CLAPR1 gene encodes a modified protein which may comprise an insertion of at least one glutamine (Q) at position p. 534_535insQ in SEQ ID NO: 6. more preferably, the modified CLAPR1 gene encodes a modified protein which may comprise an insertion of three glutamines (Q) at position p. 534_535insQQQ in SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the invention relates to a tissue culture of a bitter melon plant of the invention, wherein the tissue culture may comprise a modified CLAPR1 gene that encodes a modified protein which may comprise one or more modifications in the wild type protein sequence of SEQ ID NO: 8. This bitter melon tissue culture is referred herein as a "bitter melon tissue culture (*Momordica charantia*) of the invention". The bitter melon tissue culture of the invention provides genetic information that leads to CYSDV resistance.

Preferably, the bitter melon tissue culture of the invention may comprise in its genome a modified CLAPR1 gene, wherein the modified CLAPR1 gene encodes a modified protein which may comprise an insertion of at least one glutamine (Q) at position p. 536_537insQ of SEQ ID NO: 8. Preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8. In one embodiment, the invention relates to a tissue culture of a squash plant of the invention, wherein the tissue culture may comprise a modified CLAPR1 gene that encodes a modified protein which may comprise one or more modifications in the wild type protein sequence of SEQ ID NO: 10. This squash tissue culture is referred herein as a "squash tissue culture (*Cucurbita maxima*) of the invention". The squash tissue culture of the invention provides genetic information that leads to CYSDV resistance.

Preferably, the squash tissue culture of the invention may comprise in its genome a modified CLAPR1 gene, wherein the modified CLAPR1 gene encodes a modified protein which may comprise an insertion of at least one glutamine (Q) at position p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the invention relates to a tissue culture of a watermelon plant of the invention, wherein the tissue culture may comprise a modified CLAPR1 gene that encodes a modified protein which may comprise one or more modifications in the wild type protein sequence of SEQ ID NO: 12. This watermelon tissue culture is referred herein as a "watermelon tissue culture (*Citrullus lanatus*) of the invention". The watermelon tissue culture of the invention provides genetic information that leads to CYSDV resistance.

Preferably, the watermelon tissue culture of the invention may comprise in its genome a modified CLAPR1 gene, wherein the modified CLAPR1 gene encodes a modified protein which may comprise an insertion of at least one glutamine (Q) at position p. 532_533insQ in SEQ ID NO: 12. Preferably, the modified CLAPR1 gene encodes a modified protein which may comprise an insertion of three glutamines (Q) at position p. 532_533insQQQ in SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention also relates to propagation material suitable for producing a plant of the invention, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material and the plant produced from the propagation material may comprise the modified CLAPR1 gene of the invention that confers resistance to CYSDV. This propagation material is referred herein as "propagation material of the invention". A plant of the invention may be used as a source of the propagation material.

In one embodiment, the propagation material of the invention is suitable for producing a melon plant of the invention, wherein the propagation material may comprise a modified CLAPR1 gene that encodes a modified protein which may comprise one or more modifications in the wild type protein sequence of SEQ ID NO: 2. This melon propagation material is referred herein as "melon propagation material (*Cucumis melo*) of the invention". A plant produced from the melon propagation material of the invention may comprise the modified CLAPR1 gene of the invention that confers resistance to CYSDV.

Preferably, the melon propagation material of the invention may comprise in its genome a modified CLAPR1 gene, wherein the modified CLAPR1 gene encodes a modified protein which may comprise an insertion of at least one glutamine (Q) at position p. 533_534insQ of SEQ ID NO: 2. More, preferably, the modified CLAPR1 gene encodes a modified protein which may comprise an insertion of three glutamines (Q) at position p.533_534insQQQ of SEQ ID NO: 2. Alternatively or additionally, the modified CLAPR1 gene encodes a modified protein comprising one or more amino acid changes or a premature stop codon in its ENTH/VHS domain, ENTH domain, ANTH domain or Phosphoinositide binding clathrin adaptor domain 2 in SEQ ID NO: 2.

In one embodiment, the propagation material of the invention is suitable for producing a cucumber plant of the invention, wherein the propagation material may comprise a modified CLAPR1 gene that encodes a modified protein which may comprise one or more modifications in the wild type protein sequence of SEQ ID NO: 6. This cucumber propagation material is referred herein as "cucumber propagation material (*Cucumis sativus*) of the invention". A plant produced from the cucumber propagation material of the invention may comprise the modified CLAPR1 gene of the invention that confers resistance to CYSDV. Preferably, the propagation material suitable for producing a cucumber plant of the invention may comprise in its genome a modified CLAPR1 gene, wherein the modified CLAPR1 gene encodes a modified protein comprising an insertion of at least one glutamine (Q) at position p. 534_535insQ of SEQ ID NO: 6. More preferably, the modified CLAPR1 gene encodes a modified protein which may comprise an insertion of three glutamines (Q) at position p. 534_535insQQQ of SEQ ID NO: 6. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 6.

In one embodiment, the propagation material of the invention is suitable for producing a bitter melon plant of the invention, wherein the propagation material may comprise a modified CLAPR1 gene that encodes a modified protein which may comprise one or more modifications in the wild type protein sequence of SEQ ID NO: 8. This bitter melon propagation material is referred herein as "bitter melon propagation material (*Momordica charantia*) of the invention". A plant produced from the bitter melon propagation material of the invention may comprise the modified CLAPR1 gene of the invention that confers resistance to CYSDV.

Preferably, the propagation material suitable for producing a bitter melon plant of the invention may comprise in its genome a modified CLAPR1 gene, wherein the modified CLAPR1 gene encodes a modified protein which may comprise an insertion of at least one glutamine (Q) at position p. 536_537insQ of SEQ ID NO: 8. More preferably, the modified CLAPR1 gene encodes a modified protein which may comprise an insertion of three glutamines (Q) at position p. 536_537insQQQ of SEQ ID NO: 8. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 8.

In one embodiment, the propagation material of the invention is suitable for producing a squash plant of the invention, wherein the propagation material may comprise a modified CLAPR1 gene that encodes a modified protein which may comprise one or more modifications in the wild type protein sequence of SEQ ID NO: 10. This squash propagation material is referred herein as "squash propagation material (*Cucurbita maxima*) of the invention". A plant produced from the squash propagation material of the invention may comprise the modified CLAPR1 gene of the invention that confers resistance to CYSDV.

Preferably, the propagation material suitable for producing a squash plant of the invention may comprise in its genome a modified CLAPR1 gene, wherein the modified CLAPR1 gene encodes a modified protein which may comprise an insertion of at least one glutamine (Q) at position p. 537_538insQ of SEQ ID NO: 10. More preferably, the modified CLAPR1 gene encodes a modified protein which may comprise an insertion of three glutamines (Q) at position p. 537_538insQQQ of SEQ ID NO: 10. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 10.

In one embodiment, the propagation material of the invention is suitable for producing a watermelon plant of the invention, wherein the propagation may comprise a modified CLAPR1 gene that encodes a modified protein which may comprise one or more modifications in the wild type protein sequence of SEQ ID NO: 12. This watermelon propagation material is referred herein as "watermelon propagation material (*Citrullus lanatus*) of the invention". A plant produced from the watermelon propagation material of the invention may comprise the modified CLAPR1 gene of the invention that confers resistance to CYSDV.

Preferably, the propagation material suitable for producing a watermelon plant of the invention which is resistant to CYSDV, may comprise in its genome a modified CLAPR1 gene, wherein the modified CLAPR1 gene encodes a modified protein which may comprise an insertion of at least one glutamine (Q) at position p. 532_533insQ of SEQ ID NO: 12. More preferably, the modified CLAPR1 gene encodes a modified protein which may comprise an insertion of three glutamines (Q) at position p. 532_533insQQQ of SEQ ID NO: 12. Alternatively or additionally, the modified CLAPR1 gene encodes a modified protein which may comprise one or more amino acid changes or a premature stop codon in its ENTH/VHS domain, ENTH domain, ANTH domain or Phosphoinositide binding clathrin adaptor domain 2 in SEQ ID NO: 12.

The invention further relates to plant tissue of a plant of the invention. The tissue can be undifferentiated tissue or already differentiated tissue. Undifferentiated tissues are for example stem tips, anthers, petals, pollen and can be used in micropropagation to obtain new plantlets that are grown into plants of the invention. The tissue can also be grown from a cell of the invention.

The invention further relates to parts of a plant of the invention that are suitable for sexual reproduction. Such parts are for example selected from the group consisting of microspores, pollen, ovaries, ovules, embryo sacs, and egg cells. Additionally the invention relates to parts of a plant of the invention that are suitable for vegetative reproduction, which are in particular cuttings, roots, stems, cells, protoplasts. The parts of the plants as previously mentioned are considered propagation material. The plant that is produced from the propagation material may comprise a modified CLAPR1 gene that leads to CYSDV resistance.

The invention further relates to the germplasm of plants of the invention. The germplasm is constituted by all inherited characteristics of an organism and according to the invention encompasses at least the trait of the invention. The germplasm can be used in a breeding program for the development of plants resistant to CYSDV. The use of germplasm that may comprise a modified CLAPR1 gene leading to CYSDV resistance in breeding is also part of the present invention.

The invention additionally further relates to the use of a plant of the invention in plant breeding. The invention thus relates to a breeding method for the development of plants that are resistant to CYSDV wherein the germplasm which may comprise said resistance is used. In one embodiment, seed being representative for the germplasm was deposited with NCIMB under accession number NCIMB 42992.

The invention also relates to the use of a modified CLAPR1 gene for producing a plant that is resistant to CYSDV, preferably a plant of the species *Cucumis melo, Cucumis sativus, Momordica charantia, Cucurbita maxima*, or *Citrullus lanatus*. The CYSDV resistant plant may be produced by introducing the modified CLAPR1 gene into its genome, by means of mutagenesis or introgression, or combinations thereof.

The invention further relates to plants of the invention that have acquired a modified CLAPR1 gene from a suitable source, either by conventional breeding, or genetic modification, in particular by cisgenesis or transgenesis. Cisgenesis is a genetic modification of plants with a natural gene, encoding a (agricultural trait) from the crop plant itself or from a sexually compatible donor plant. Transgenesis is a genetic modification of a plant with a gene from a non-crossable species or with a synthetic gene.

The source from which a modified CLAPR1 gene can be acquired, is formed by plants grown from seeds of which a representative sample was deposited under accession number NCIMB 42992, or from the deposited seeds NCIMB 42992, or from sexual or vegetative descendants thereof, or from another source which may comprise the modified CLAPR1 gene as defined herein that leads to resistance to CYSDV, or from any combination of these sources.

To obtain a modified CLAPR1 gene from a source in which it is heterozygously present, a seed of such a plant may be grown and flowers pollinated from the same plant or from another plant that also has a heterozygous modified CLAPR1 gene to obtain a fruit with seeds. When these seeds are sown, the resulting plants will segregate according to normal segregation ratios, which means about 25% of the plants will have the modified CLAPR1 gene homozygously present, about 50% of the plants will have the modified CLAPR1 gene heterozygously present and about 25% of the plants will not have the modified CLAPR1 gene. For the selection of a preferred plant having a modified CLAPR1 gene either homozygously or heterozygously, the presence of a modified CLAPR1 gene can be determined by sequencing the CLAPR1 gene or by markers developed based on the sequences that are described herein. Alternatively, plants can be phenotypically observed and visually selected for the presence of resistance to CYSDV. The skilled person is aware of how to work with genes in heterozygous and homozygous form using known breeding and selection procedures.

The invention also relates to a method for producing a plant of any one of the following members of the Cucurbitaceae family: *Cucumis melo* (melon), *Cucumis sativus* (cucumber), *Momordica charantia* (bitter melon), *Cucurbita maxima* (squash), or *Citrullus lanatus* (watermelon), in particular a *Cucumis melo* plant, which plant is resistant against CYSDV, said method which may comprise:

(a) crossing a plant which may comprise a modified CLAPR1 gene of the invention with another plant to obtain an F1 population;
(b) optionally performing one or more rounds of selfing and/or crossing a plant from the F1 to obtain a further generation population;
(c) selecting from the population a plant that may comprise the modified CLAPR1 gene and is resistant against CYSDV.

The invention also relates to a method for producing a plant of any one of the following members of the Cucurbitaceae family: *Cucumis melo* (melon), *Cucumis sativus* (cucumber), *Momordica charantia* (bitter melon), *Cucurbita maxima* (squash), or *Citrullus lanatus* (watermelon), in particular a *Cucumis melo* plant, which plant is resistant against CYSDV, said method which may comprise:
(a) introducing one or more mutations in a population of plants;
(b) selecting a plant showing resistance to CYSDV;
(c) verifying if the plant selected in step (b) has a mutation in its CLAPR1 gene, and selecting a plant which may comprise such a mutation;
(d) growing the plant obtained in step (c), wherein the wild type CLAPR1 gene encodes a protein which may comprise at least 86% sequence identity, preferably 87%, 88%, 89%, 90%, 91%, 92%, 93%, 94%, 95%, 96%, 97%, 98%, or 99% sequence identity to SEQ ID NO: 2.

The invention further relates to a method for the production of a melon plant which is resistant to CYSDV, said method which may comprise:
(a) crossing a melon plant of the invention which may comprise a modified CLAPR1 gene of the invention with another melon parent plant not which may comprise the modified CLAPR1 gene, to obtain an F1 population;
(b) optionally performing selfing an F1 plant to obtain an F2 population;
(c) backcrossing an F1 or an F2 plant with the preferred parent to obtain a BC1 population; and
(d) optionally selfing a BC1 plant to obtain a BC1F2 population;
(e) selecting in the BC1 or BC1F2 population for a melon plant that may comprise the modified CLAPR1 gene and is resistant to CYSDV, suitably by sequencing the CLAPR1 gene. The plant can also be phenotypically selected for having resistance to CYSDV. The backcrossing, selfing and selection steps may optionally be repeated one to ten more times to produce further backcross progeny which may comprise the modified CLAPR1 gene and which is resistant against CYSDV.

The plant of the invention used in the above methods for the production of a *Cucumis melo* plant which is resistant to CYSDV, can be any plant of the invention as described herein, and may be a plant grown from seed deposited under NCIMB accession number 42992 for the production of a melon plant.

Preferably, the modified CLAPR1 gene in the above methods for the production of a *Cucumis melo* plant which is resistant to CYSDV, may comprise an insertion of at least three nucleotides, which corresponds to an insertion of at least one glutamine (Q) at position 533_534insQ of SEQ ID NO: 2 in the encoded protein, more in particular, the modified CLAPR1 gene may comprise an insertion of nine nucleotides, which corresponds to an insertion of three glutamines (Q) at position 533_534insQQQ of SEQ ID NO: 2 in the encoded protein.

The invention further relates to a method of introducing another desired trait into a melon plant which may comprise resistance to CYSDV, which may comprise:
(a) crossing a melon plant of the invention which may comprise a modified CLAPR1 gene with a second melon plant that may comprise the other desired trait to produce F1 progeny;
(b) selecting an F1 progeny that may comprise the modified CLAPR1 gene and the desired trait;
(c) crossing the selected F1 progeny which may comprise the modified CLAPR1 gene with either parent, to produce backcross progeny;
(d) selecting backcross progeny which may comprise the modified CLAPR1 gene and the other desired trait; and
(e) optionally repeating steps c) and d) one or more times in succession to produce selected fourth or higher backcross progeny that may comprise the desired trait and has resistance to CYSDV.

Optionally, selfing steps are performed after any one of the crossing or backcrossing steps. Selection of a plant which may comprise a modified CLAPR1 gene of the invention and the other desired trait can alternatively be done following any crossing or selfing step of the method. The desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a melon plant produced by this method and the melon fruit and see obtained therefrom.

The plant of the invention used in the method of introducing another desired trait into a melon plant which may comprise resistance to CYSDV may be a plant grown from seed deposited under NCIMB accession number 42992.

The invention further relates to a method for the production of a melon plant which may comprise a modified CLAPR1 gene that leads to resistance to CYSDV, by using tissue culture of plant material that may comprise a modified CLAPR1 gene in its genome.

The invention further relates to a method for the production of a melon plant which may comprise a modified CLAPR1 gene that leads to resistance to CYSDV, by using vegetative reproduction of plant material that may comprise a modified CLAPR1 gene in its genome.

The invention further provides a method for the production of a melon plant having resistance to CYSDV as defined herein by using doubled haploid generation techniques to generate a doubled haploid line that homozygously may comprise a modified CLAPR1 gene and is resistant against CYSDV.

The invention further relates to a method for the production of a melon plant which may comprise a modified CLAPR1 gene that leads to resistance to CYSDV, which method may comprise growing a seed which may comprise a modified CLAPR1 gene into said melon plant. The seed used in the method may be seed deposited under NCIMB accession number 42992, or progeny seed thereof.

The invention further relates to a method for seed production which may comprise growing melon plants from seeds of the invention, allowing the plants to produce melon fruits with seeds, and harvesting those seeds. Production of the seeds is suitably done by crossing or selfing. Preferably the melon seeds that are so produced have the capability to grow into melon plants that are resistant to CYSDV.

The invention further relates to hybrid seed and to a method for producing said hybrid seed, which may comprise crossing a first parent plant with a second parent plant and harvesting the resultant hybrid seed, wherein the first parent plant and/or the second parent plant is a plant of the invention. The resultant hybrid plant which may comprise a modified CLAPR1 gene of the invention and which exhibits resistance to CYSDV is also a plant of the invention.

It is clear that the parent that provides the trait of the invention is not necessarily a plant grown directly from the deposited seeds. The parent can also be a progeny plant from the seed or a progeny plant from sees that are identified to have the trait of the invention by other means.

Introgression of a modified CLAPR1 gene as used herein means introduction of the modified CLAPR1 gene from a donor plant which may comprise said modified CLAPR1 gene into a recipient plant not carrying said modified CLAPR1 gene by standard breeding techniques wherein selection for plants which may comprise the modified CLAPR1 gene can be performed phenotypically by means of observation of the resistance to CYSDV, or selection can be performed with the use of markers through marker assisted breeding, or combinations of these. Selection is started in the F1 or any further generation from a cross between the recipient plant and the donor plant, suitably by using markers developed based on the sequence of the modified CLAPR1 gene. The skilled person is familiar with creating and using molecular markers that can be used to identify or are linked to the trait of the invention. Development and use of such markers for identifying and selecting plants of the invention also form part of the invention.

The invention also relates to a method for identifying or selecting a plant of any one of the following members of the Cucurbitaceae family: *Cucumis melo* (melon), *Cucumis sativus* (cucumber), *Momordica charantia* (bitter melon), *Cucurbita maxima* (squash), or *Citrullus lanatus* (watermelon), in particular a *Cucumis melo*, which plant is resistant against CYSDV, said method which may comprise:
  (a) assaying genomic nucleic acids of a plant of the Cucurbitaceae family for the presence of one or more modifications in the CLAPR1 gene;
  (b) identifying or selecting a plant if one or more modifications in the CLAPR1 gene are present as a plant of the Cucurbitaceae family that is resistant to CYSDV; and
  (c) optionally verifying if the plant is resistant to CYSDV.

Preferably, the one or more modifications in the CLAPR1 gene is an insertion of at least three nucleotides, which corresponds to an insertion of at least one glutamine (Q) at position 533_534insQ of SEQ ID NO: 2 in the encoded protein, more in particular, an insertion of nine nucleotides, which corresponds to an insertion of three glutamines (Q) at position 533_534insQQQ of SEQ ID NO: 2 in the encoded protein. Such a modification to the CLAPR1 gene can be identified by means of the Polymerase Chain Reaction (PCR), using a primer pair to amplify the genomic DNA region surrounding the insertion. The forward primer is preferably a nucleic acid molecule having the sequence of SEQ ID NO: 13 and the reverse primer is preferably a nucleic acid molecule having the sequence of SEQ ID NO: 14.

PCR conditions for amplifying an insertion of at least three nucleotides in the CLAPR1 gene, which corresponds to an insertion of at least one glutamine (Q) at position 533_534insQ of SEQ ID NO: 2 in the encoded protein, more in particular, an insertion of nine nucleotides, which corresponds to an insertion of three glutamines (Q) at position 533_534insQQQ of SEQ ID NO: 2 in the encoded protein, using primers having SEQ ID NO: 13 and SEQ ID NO: 14 are as follows, using Platinum Taq enzyme (Thermo Fisher Scientific): 5 minutes at 95° C. (initial denaturing step); 35 amplification cycles, each cycle consisting of: 30 seconds denaturation at 94° C., 30 seconds annealing at 55° C., and 30 seconds extension at 72° C.; 1 minutes at 72° C. (final extension step).

The presence of the one or more modifications in the CLAPR1 gene can also suitably be identified for example by sequencing the modified CLAPR1 gene of a given member of the Cucurbitaceae family described herein and comparing it with its respective wild type CLAPR1 gene sequence (SEQ ID NO: 1, 5, 7, 9 or 11). The skilled person is familiar with techniques available in the art for determining the genomic DNA or the coding DNA sequence. These techniques are for example PCR amplification followed by Sanger sequencing or whole genome sequencing. Additionally the modifications in the CLAPR1 gene can also suitably be identified by using markers developed based on the sequence of the modified CLAPR1 gene. The skilled person is familiar with creating and using molecular markers that can be used to identify or are linked to the trait of the invention.

TABLE 1

| | Sequence Information |
|---|---|
| SEQ ID NO: 1<br>CDS of *C. melo*<br>CLAPR1 gene | ATGGGCACATTTCAGAGCTTCCGCAAAGCTTATGGCGCTCTCA<br>AAGATTCCACCAAGGTCGGCCTCGCTAAGGTCAACAGCGAAT<br>TCAAGGATTTGGATATCGCCATCGTTAAGGCTACCAATCACGT<br>TGAATGTCCGCCTAAAGAACGTCATGTTCGAAAAATTTTTTCG<br>GCTACGTCCGTTGTGAGACCTCGGGCAGATGTGGCGTATTGTA<br>TTCATGCATTGGCGAAGAGATTGTCGAAGACGCGGAATTGGA<br>TCGTTGCCTTGAAGACGTTGATAGTTGTACATAGGACATTGAG<br>AGAGGGAGATCCCACCTTCAGGGAAGAACTTCTTAATTATTCA<br>CACAGAGGACATATTCTCCAAATATCCAATTTTAAGGATGATT<br>CGAGTCCTCTTGCTTGGGATTGTTCTGCTTGGGTAAGGACATA<br>TGCCCTTTTTCTAGAAGAGAGACTTGAATGTTATAGAATCTTG<br>AAGTATGATATTGAATCGGAACGTCTAACGAAAACATCACCT<br>GGATCGACGAAGGTCCATAGTAGGACACGATTGCTGAACTCT<br>GATGAGCTACTGGAGCAGCTACCCGCATTGCAGCAACTTCTCT<br>ACCGCCTTATGGGATGTCAGCCAGAAGGAGGAGCTTACAGCA<br>ACTATCTTATCCAGTATGCCCTGGCTTTGGTACTCAAAGAGAG<br>CTTTAAAATATATTGTGCGATAAATGATGGAATAATAAATCTT<br>GTGGACATGTTCTTTGATATGCCAAGGCATGATGCAGTTAAAG<br>CTCTCAATATATACAAAAGAGCAAGCAACCAGGCTGAAAATC<br>TTGCGGATTTTTACGAATACTGTAAGGGATTGGAACTTGCTAG |

TABLE 1-continued

Sequence Information

|  |  |
|---|---|
|  | AACTTTTCAGTTTCCCACTTTGAAGCAGCCACCTCCATCATTTC<br>TTTCAACAATGGAGGAGTATATAAGAGAAGCACCACAGACTG<br>GTTCTGTTAATAAGAGACTGGAATACCGAGAGACAGAGCTAT<br>TGACACAGGAAGAGGATAAGCCCGAAGAATCAGCCGAAATTG<br>AAAAGGAGGTTGAAATGTTGAGGACAACAAACCACTGGTTG<br>AAACAGAGGAAGAACCCCAACAGAAGGAAGAGGAGGTTGCT<br>GAACCTCCACCTCTAATAGAAACCCACGACCCAAGTGATCTTC<br>TGGGTCTGAATGAAATAAATCCCAAAGCTGCAGAAATAGAAG<br>AAAGCAATGCTTTAGCTCTTGCTATTGTTACAAATGGGAATGA<br>CCCATCTTCTTCAAATCGTGCATTGAGTGAAATTGGCGGTAGT<br>GGTTGGGAGCTAGCGCTTGTTACCACACCAAGCAATAATACT<br>GGTCCTTCTGTCGAAGGCAGACTGGCCGGGGGCTTTGACAAG<br>CTATTGCTTGATAGCTTGTATGAAGATGAACATGCCAGAAGAC<br>ATCTTCAGCTTCAGAATGCTGGATATGGACCATACGGGGAAA<br>TGATGGTACAGAATCCATTCGAACAGCATGACCCGTTTTCATT<br>GTCGAGCAACATAGCGCCTCCTCCGAACGTGCAAATGGCAAT<br>GATGGCTCAACAACAACAAATGCTTTTCCAACACCAACAACA<br>ACCATTACAAAGCAATACCTTCCCTCAGCAACAACAGCAGTT<br>ACATTCAAATGACTCAATGATGATGGTTCCTTATCAACAACAG<br>TTGCCTCAATACCCACAACAACAAATGCAACAAATTGGTCCTT<br>CTAATCCATTTGGTGACCCTTTTCTTTCCTTTCCTCAAACTTCA<br>GTACCCCCAGGAGGACATCATAATCTAATCTAG |
| SEQ ID NO: 2<br>C. melo<br>CLAPR1 protein sequence | MGTFQSFRKAYGALKDSTKVGLAKVNSEFKDLDIAIVKATNHVE<br>CPPKERHVRKIFSATSVVRPRADVAYCIHALAKRLSKTRNWIVAL<br>KTLIVVHRTLREGDPTFREELLNYSHRGHILQISNFKDDSSPLAW<br>DCSAWVRTYALFLEERLECYRILKYDIESERLTKTSPGSTKVHSR<br>TRLLNSDELLEQLPALQQLLYRLMGCQPEGGAYSNYLIQYALAL<br>VLKESPKIYCAINDGIINLVDMFFDMPRHDAVKALNIYKRASNQA<br>ENLADFYEYCKGLELARTFQFPTLKQPPPSFLSTMEEYIREAPQTG<br>SVNKRLEYRETELLTQEEDKPEESAEIEKEVENVEDNKPLVETEE<br>EPQQKEEEVAEPPPLIETHDPSDLLGLNEINPKAAEIEESNALALAI<br>VTNGNDPSSSNRALSEIGGSGWELALVTTPSNNTGPSVEGRLAGG<br>FDKLLLDSLYEDEHARRHLQLQNAGYGPYGEMMVQNPFEQHDP<br>FSLSSNIAPPPNVQMAMMAQQQQMLFQHQQQPLQSNTFPQQQQ<br>QLHSNDSMMMVPYQQQLPQYPQQQMQQIGPSNPFGDPFLSFPQT<br>SVPPGGHHNLI |
| SEQ ID NO: 3<br>CDS of C. melo<br>CLAPR1 gene with<br>c.1599_1600insCAGCAACAA<br>(bold and underlined) | ATGGGCACATTTCAGAGCTTCCGCAAAGCTTATGGCGCTCTCA<br>AAGATTCCACCAAGGTCGGCCTCGCTAAGGTCAACAGCGAAT<br>TCAAGGATTTGGATATCGCCATCGTTAAGGCTACCAATCACGT<br>TGAATGTCCGCCTAAAGAACGTCATGTTCGAAAAATTTTTTCG<br>GCTACGTCCGTTGTGAGACCTCGGGCAGATGTGGCGTATTGTA<br>TTCATGCATTGGCGAAGAGATTGTCGAAGACGCGAATTGAA<br>TCGTTGCCTTGAAGACGTTGATAGTTGTACATAGGACATTGAG<br>AGAGGGAGATCCCACCTTCAGGGAAGAACTTCTTAATTATTCA<br>CACAGAGGACATATTCTCCAAATATCCAATTTTAAGGATGATT<br>CGAGTCCTCTTGCTTGGGATTGTTCTGCTTGGGTAAGGACATA<br>TGCCCTTTTTCTAGAAGAGAGACTTGAATGTTATAGAATCTTG<br>AAGTATGATATTGAATCGGAACGTCTAACGAAAACATCACCT<br>GGATCGACGAAGGTCCATAGTAGGACACGATTGCTGAACTCT<br>GATGAGCTACTGGAGCAGCTACCCGCATTGCAGCAACTTCTCT<br>ACCGCCTTATGGGATGTCAGCCAGAAGGAGGAGCTTACAGCA<br>ACTATCTTATCCAGTATGCCCTGGCTTTGGTACTCAAAGAGAG<br>CTTTAAAATATATTGTGCGATAAATGATGGAATAATAAATCTT<br>GTGGACATGTTCTTTGATATGCCAAGGCATGATGCAGTTAAAG<br>CTCTCAATATATACAAAAGAGCAAGCAACCAGGCTGAAAATC<br>TTGCGGATTTTTACGAATACTGTAAGGGATTGGAACTTGCTAG<br>AACTTTTCAGTTTCCCACTTTGAAGCAGCCACCTCCATCATTTC<br>TTTCAACAATGGAGGAGTATATAAGAGAAGCACCACAGACTG<br>GTTCTGTTAATAAGAGACTGGAATACCGAGAGACAGAGCTAT<br>TGACACAGGAAGAGGATAAGCCCGAAGAATCAGCCGAAATTG<br>AAAAGGAGGTTGAAATGTTGAGGACAACAAACCACTGGTTG<br>AAACAGAGGAAGAACCCCAACAGAAGGAAGAGGAGGTTGCT<br>GAACCTCCACCTCTAATAGAAACCCACGACCCAAGTGATCTTC<br>TGGGTCTGAATGAAATAAATCCCAAAGCTGCAGAAATAGAAG<br>AAAGCAATGCTTTAGCTCTTGCTATTGTTACAAATGGGAATGA<br>CCCATCTTCTTCAAATCGTGCATTGAGTGAAATTGGCGGTAGT<br>GGTTGGGAGCTAGCGCTTGTTACCACACCAAGCAATAATACT<br>GGTCCTTCTGTCGAAGGCAGACTGGCCGGGGGCTTTGACAAG<br>CTATTGCTTGATAGCTTGTATGAAGATGAACATGCCAGAAGAC<br>ATCTTCAGCTTCAGAATGCTGGATATGGACCATACGGGGAAA<br>TGATGGTACAGAATCCATTCGAACAGCATGACCCGTTTTCATT<br>GTCGAGCAACATAGCGCCTCCTCCGAACGTGCAAATGGCAAT<br>GATGGCTCAACAACAACAAATGCTTTTCCAACACCAACAACA<br>ACCATTACAAAGCAATACCTTCCCTCAGCAACAACAGCAACA<br>ACAGCAGTTACATTCAAATGACTCAATGATGATGGTTCCTTAT<br>CAACAACAGTTGCCTCAATACCCACAACAACAAATGCAACAA |

TABLE 1-continued

| | Sequence Information |
|---|---|
| | ATTGGTCCTTCTAATCCATTTGGTGACCCTTTTCTTTCCTTTCCT<br>CAAACTTCAGTACCCCCAGGAGGACATCATAATCTAATCTAG |
| SEQ ID NO: 4<br>C. melo<br>CLAPR1 protein<br>sequence with<br>p.533_534insQQQ<br>(bold and<br>underlined) | MGTFQSFRKAYGALKDSTKVGLAKVNSEFKDLDIAIVKATNHVE<br>CPPKERHVRKIFSATSVVRPRADVAYCIHALAKRLSKTRNWIVAL<br>KTLIVVHRTLREGDPTFREELLNYSHRGHILQISNFKDDSSPLAW<br>DCSAWVRTYALFLEERLECYRILKYDIESERLTKTSPGSTKVHSR<br>TRLLNSDELLEQLPALQQLLYRLMGCQPEGGAYSNYLIQYALAL<br>VLKESFKIYCAINDGIINLVDMFFDMPRHDAVKALNIYKRASNQA<br>ENLADFYEYCKGLELARTFQFPTLKQPPPSFLSTMEEYIREAPQTG<br>SVNKRLEYRETELLTQEEDKPEESAEIEKEVENVEDNKPLVETEE<br>EPQQKEEEVAEPPPLIETHDPSDLLGLNEINPKAAEIEESNALALAI<br>VTNGNDPSSSNRALSEIGGSGWELALVTTPSNNTGPSVEGRLAGG<br>FDKLLLDSLYEDEHARRHLQLQNAGYGPYGEMMVQNPFEQHDP<br>FSLSSNIAPPPNVQMAMMAQQQQMLFQHQQQPLQSNTFPQQQQ<br>QQQQLHSNDSMMMVPYQQQLPQYPQQQMQQIGPSNPFGDPFLS<br>FPQTSVPPGGHHNLI |
| SEQ ID NO: 5<br>CDS of C. sativus<br>CLAPR1 gene | ATGGGCACATTTCAGAGCTTTCGCAAAGCTTATGGGGCTCTCA<br>AAGATTCCACCAAGGTCGGCCTCGCTAAGGTCAACAGCGAGT<br>TCAAGGATTTGGATATCGCCATTGTTAAGGCTACCAATCACGT<br>TGAATGTCCGCCTAAGGAACGTCATGTTCGAAAAATTTTTTCG<br>GCTACGTCCGTTGTGAGACCTAGGGCAGATGTGGCGTATTGTA<br>TTCATGCATTGGCGAAGAGATTGTCGAAGACGCGGAATTGGA<br>TCGTTGCCTTGAAGACGTTGATAGTTGTACATAGGACATTGAG<br>AGAGGGAGATCCAACCTTCAGGGAAGAACTTCTCAATTATTC<br>ACACAGAGGACATATTCTCCAAATATCAAATTTTAAGGATGAT<br>TCAAGTCCTCTTGCTTGGGATTGTTCAGCTTGGGTAAGGACAT<br>ATGCCCTTTTTCTAGAAGAGAGACTTGAATGTTATAGAATCTT<br>GAAGTATGATATTGAATCGGAACGTCAACGAAAACATCACC<br>TGGATCAACGAAGGTCCATAGTAGGACACGATTGCTGAACTC<br>TGATGAGCTACTGGAGCAGCTACCCGCATTGCAGCAACTTCTC<br>TACCGCCTTATGGGATGTCAGCCAGAAGGAGGAGCTTACAGC<br>AATTATCTTATCCAATATGCCCTGGCTTTGGTACTCAAAGAGA<br>GCTTTAAAATATATTGTGCGATAAATGATGGAATAATAAATCT<br>TGTGGACATGTTCTTTGATATGCCAAGGCATGATGCAGTTAAA<br>GCTCTCAATATATACAAAAGAGCAAGCAACCAGGCTGAAAAT<br>CTTGCGGATTTTTACGAATACTGTAAGGGATTGGAACTTGCTA<br>GAACTTTTCAGTTTCCCACATTGAAGCAGCCACCTCCATCATT<br>TCTTTCAACAATGGAGGAGTATATAAGAAGCACCACAAC<br>TGGTTCTGTTAATAAGAGACTAGAATACCGAGAGGCAGAGCA<br>ATTGACACAGGAACAAGATAAGCCCGAAGAACCAGGCGAAA<br>TTGAAAAGGAAGTTGAAATGTTGAGGACAACAAACCACCGG<br>TTGAAACAGAGGAAGAACCCCAACAGAAGGAAGGGGAGGTT<br>GCTGAACCTCCACCTCTAATAGCAACCCACGACGCAAGTGAT<br>CTTCTGGGTCTGAATGAAATAAATCCCAGAGCTGCAGAAATA<br>GAAGAAAGCAATGCTTTAGCTCTTGCTATTATTACAAATGGGA<br>ATGATCCATCTTCTTCAAATCGTGCATTGAGTGAAATTGGCGG<br>TAGTGGTTGGGAGCTAGCGCTTGTTACCACACCAAGCAATAAT<br>GCTGGTCCTTCTGTCGAAGGCAAACTGGCCGGGGGCTTTGACA<br>AGCTATTGCTTGATAGCTTGTATGAAGATGAACATGCCAGAA<br>GACATCTTCAGCTTCAGAATGCCGGATATGGACCTTACGGAG<br>AAATGATGGTACATAATCCATTTGAACAGCATGACCCGTTTTC<br>ATTGTCGAGCAACATAGCGCCTCCTCCGAGCGTGCAAATGGC<br>AATGATGGCTCAACAACAACAAATGCTTTTCCAACACCAACA<br>ACAACAACCATTACAAAGCAATGCCTTCCCTCAGCAACAACA<br>ACAATTACATTCAAATGACTCAATGATGATGGTTCCTTATCAA<br>CAACAGTTGCCTCAATACCCTCAACAACAAATGCAACAAATG<br>CAACAAATTGGTCCTTCTAATCCATTTGGTGACCCTTTTCTTTC<br>CTTTCCTCAAACTTCAGTACCCCCAGGAGGACATCATAATCTA<br>ATCTAG |
| SEQ ID NO: 6<br>C. sativus<br>CLAPR1 protein | MGTFQSFRKAYGALKDSTKVGLAKVNSEFKDLDIAIVKATNHVE<br>CPPKERHVRKIFSATSVVRPRADVAYCIHALAKRLSKTRNWIVAL<br>KTLIVVHRTLREGDPTFREELLNYSHRGHILQISNFKDDSSPLAW<br>DCSAWVRTYALFLEERLECYRILKYDIESERLTKTSPGSTKVHSR<br>TRLLNSDELLEQLPALQQLLYRLMGCQPEGGAYSNYLIQYALAL<br>VLKESFKIYCAINDGIINLVDMFFDMPRHDAVKALNIYKRASNQA<br>ENLADFYEYCKGLELARTFQFPTLKQPPPSFLSTMEEYIREAPQTG<br>SVNKRLEYREAEQLTQEQDKPEEPGEIEKEVENVEDNKPPVETEE<br>EPQQKEGEVAEPPPLIATHDASDLLGLNEINPRAAEIEESNALALA<br>IITNGNDPSSSNRALSEIGGSGWELALVTTPSNNAGPSVEGKLAG<br>GFDKLLLDSLYEDEHARRHLQLQNAGYGPYGEMMVHNPFEQHD<br>PFSLSSNIAPPPSVQMAMMAQQQQMLFQHQQQQPLQSNAFPQQ<br>QQQLHSNDSMMMVPYQQQLPQYPQQQMQQMQQIGPSNPFGDP<br>FLSFPQTSVPPGGHHNLI |

TABLE 1-continued

Sequence Information

SEQ ID NO: 7
CDS of *M. charantia* CLAPR1 gene

ATGGGCACGTTTCAGAGCTTTCGCAAAGCTTATGGAGCTCTCA
AGGACTCCACCAAGGTCGGTCTCGCCAAGGTCAACAGCGAGT
TCAAGGATTTGGATATCGCCATTGTTAAGGCCACCAATCACGT
CGAGTGCCCTCCTAAAGAGCGTCATGTTCGAAAAATATTTTCC
GCGACGTCGGTGGTGAGGCCTCGGGCGGATGTGGCGTATTGC
ATTCATGCGTTGGCGAAGAGATTGTCGAAGACGCGGAACTGG
ATCGTTGCCTTGAAGACGTTGATAGTTGTACATAGGACATTGA
GAGAGGGTGATCCAACCTTCAGGGAGGAACTTCTCAACTATT
CACACAGAGGACACATTCTTCAAATATCTAATTTTAAGGACGA
TTCAAGTCCTCTTGCTTGGGATTGTTCTGCATGGGTAAGGACG
TATGCCCTTTTTCTAGAAGAGCGACTTGAATGTTACAGAATCT
TGAAGTATGATATCGAATCAGAACGTTTAACGAAAACATCAC
CAGGATCAAGCAAGGTACATAGTAGGACACGCTTGCTGAATT
CTGATGAGCTACTGGAACAGTTACCCGCATTGCAGCAGCTTCT
TTACCGCCTAATTGGATGTCAGCCAGAAGGAGCAGCTTACAG
TAATTATCTGATCCAGTATGCCCTGGCTCTGGTACTTAAAGAG
AGCTTTAAGATATATTGTGCGATAAATGACGGAATAATAAAT
CTTGTGGACATGTTCTTTGATATGCCAAGGCACGATGCAGTTA
AAGCTCTCAATATATACAAAAGAGCCAGCAACCAGGCTGAAA
ATCTTGCAGATTTTTATGAATATTGTAAGGGATTGGAACTTGC
TAGAACTTTTCAGTTTCCCACGTTGAAGCAGCCACCTCCATCA
TTTCTTGCAACAATGGAAGAATATATAAGAGAGGCACCACAG
ACAGGTTCTGTTAACAAGAGACTGGAATACCGAGAGGCAGAG
CTATTGACTCACAAACCAGAAGAGCCTGAAGAACCCACCGAA
ACCGAAAAGAAGGTTGAGAATGTTGATGATGACGAACCACTG
GTGGCAACAGAGGAAGAACCCCAACAGAAGGAAGAGGAGGT
CGCAGAACCTCCACCTCTTATAGCAACTGATAATACTAGTGAT
CTTCTGGGTCTGAGTGAAATAAATCCTAGAGCCGCAGAAATA
GAGGAAAGTAATGCTTTAGCTCTTGCGATAGTTACACCTGGGA
ATGATACGTCTTCTTCAAGTCGTGCTTTACATGACATCGGTGG
AACTAGAGGTTGGGAGCTAGCCCTTGTTACCACACCAAGCAA
TAATACTGGTCCAATGGTCGACAGCAAACTGGCCGGTGGGTT
CGACAAGCTATTGCTCGATAGCTTGTATGAAGATGAACATGCC
AGAAGACATCTTCAGCTGCAGAACGCAGGATATGGAACATAT
GGCGAAATGTCAGTGCAGAATCCATTCGAACAACACCAACAC
GACCCGTTTGCAATGTCAAGCGGAGTAGCGCCTCCCCCGAAC
GTGCAAATGGCAATGATGCAGCAGCAGCAAATGCTTTTACAA
CACCAGCAGCAACAACAGTTACAACCAAACGCATTCCCACAG
CAGCATCAGCAGCAACATCCAAATGACTCCATGATGATGGTA
CCTTATCAACAACAGTTGCCTCAGTACCCTCAGCAGCAACAAC
AACAAATGCAGCAACTTGGCCCTTCTAATCCATTTGGTGACCC
TTTTCTTTCCTTTCCTCAAACCTCGGTACCGCCCCGAGGAAATC
ATAATCTAATCTAA

SEQ ID NO: 8
*M. charantia* CLAPR1 protein sequence

MGTFQSFRKAYGALKDSTKVGLAKVNSEFKDLDIAIVKATNHVE
CPPKERHVRKIFSATSVVRPRADVAYCIHALAKRLSKTRNWIVAL
KTLIVVHRTLREGDPTFREELLNYSHRGHILQISNFKDDSSPLAW
DCSAWVRTYALFLEERLECYRILKYDIESERLTKTSPGSSKVHSR
TRLLNSDELLEQLPALQQLLYRLIGCQPEGAAYSNYLIQYALALV
LKESFKIYCAINDGIINL VDMFFDMPRHDAVKALNIYKRASNQAE
NLADFYEYCKGLELARTFQFPTLKQPPPSFLATMEEYIREAPQTG
SVNKRLEYREAELLTHKPEEPEEPTETEKK VENVDDDEPLVATEE
EPQQKEEEVAEPPPLIATDNTSDLLGLSEINPRAAEIEESNALALAI
VTPGNDTSSSSRALHDIGGTRGWELALVTTPSNNTGPMVDSKLA
GGFDKLLLDSLYEDEHARRHLQLQNAGYGTYGEMSVQNPFEQH
QHDPFAMSSGVAPPPNVQMAMMQQQQMLLQHQQQQLQPNAF
PQQHQQQHPNDSMMMVPYQQQLPQYPQQQQQMQQLGPSNPF
GDPFLSFPQTSVPPRGNHNLI

SEQ ID NO: 9
CDS of *C. maxima* CLAPR1 gene

ATGGGCACATTTCAGAGCTTCCGCAAAGCTTATGGAGCTCTCA
AGGACTCCACCAAGGTCGGCCTCGCCAAGGTCAATAGCGAAT
TCAAGGATTTGGATATCGCCATTGTTAAGGCTACCAATCATGT
TGAATGTCCGCCTAAAGAACGTCATGTTCGGAAAATATTTACG
GCGACGTCCGTTGTGAGGCCTCGGGCGGATGTGGCGTATTGC
ATTCATGCATTGGCGAAGAGATTGTCAAAGACGCGGAACTGG
ATCGTTGCCTTGAAGACGTTGATAGTTGTACATAGGACATTGA
GAGAGGGTGATCCAACCTTCAGGGAAGAACTTCTCAACTATTC
ACAAAAAGGACAAGTTCTCCAAATATCAAATTTTAAGGATGA
TTCAAGTCCTCTTGCTTGGGATTGTTCTGCATGGGTAAGGACC
TATGCCCTTTTTCTAGAAGAGCGACTTGAATGTTACAGAGTCT
TGAAGTATGATATTGAATCGGAACGTCTAACAAAAACATCGC
CGGGATCAACGAAGGTACATAGTAGGACACGCTTGCTGAACT
CTGATGAGCTGCTGGACCAGCTACCCGCATTGCAGCAGGTTCT
CTACCGCCTATGGGATGTCAGCCAGAAGGAGCAGCGTATAG
TAATTATCTTATCCAGTACGCCCTGGCTCTCGTACTCAAAGAG
AGCTTTAAAATCTATTGTGCAATAAATGATGGAATAATAAACC
TTGTGGACATGTTCTTTGGCATGCCAAGGCATGATGCAGTTAA

TABLE 1-continued

Sequence Information

|  |  |
|---|---|
|  | AGCTCTCAATATATACAAAAGAGCCAGCCACCAGGCTGAAAA<br>TCTTGCGGATTTTTATGAATATTGTAAGGGATTGGAACTTGCT<br>AGAACTTTTCAGTTTCCCATATTGAAGCAGCCGCCTCCATCAT<br>TTCTTGCAACAATGGAAGAATATATAAGAGAAGCACCCCAGA<br>CAGCTTCTGTTAATAAGAGACTGGAATACCGAGTGGCAGAGG<br>AGATGACTGAGAAACCGGAAGAGCCTGAGGAACCTGCTGAAA<br>TTGAAAAGGAGGTTGAAAATGTTGACAACAAACCTCTTGAGG<br>AAACAGAGGAAGAACCCCAACAGAAAGAAGAGAGTGTCCCT<br>GAACCTCCACCTCTAATAGCAACTGAGGATACAAGTGATTTTC<br>TGGGTCTTAAGGAAATAAATCCTAGGATTGCAGAAATTGAGC<br>ATAACAATGCTTTAGCCCTTGCTATAGTTTCAAATGGGAATGA<br>TCCTTCTTCTGCAAATCCTGCTTTGAGTGACTTTGGCGGTAGTG<br>GTTGGGAGCTATCCCTTGTTACCACACCAACCAATAATGCTGG<br>TTCAACTGTCGGAAGCAAACTGGCGGGCGGGTTCGACAAGCT<br>ACTGCTCGATAGCTTGTACGAAGATGAACATGCCAGAAGAAA<br>TATTCAGCTTCAAAATGCAGGATATGGAACATACGGTGAAAT<br>GTATGTGCAGAATCCATTCCAACAGCAGAACGACCCATTTGC<br>GATGTCGAGCAGTATAGCGCCTCCTTCGAACGTGCAATTAGCA<br>ATGATGGCTCAGCAGCAGCAAATGCTTTACCAACAGCAACAA<br>CAGCAGCAGCATCAAGCGTTACAAACAAACGCGTTCCCTCAG<br>CAACAACAGTTGCATTTAGATGAGTCTATGATGATGGTACCTC<br>ATCAACAACAGTTGCCTCAGAGTAAGTACCCTCAACAGCAAC<br>AAATACAGCAGCAACAACGCCAACAAATGCAACAATTTGGTC<br>AGTCTAATCCTTTTGGAGACCCTTTTGTTCCCTTTCCTCAGAAT<br>TCTGTACCGCCGGGGGGAAATCATAATCTAATCTAG |
| SEQ ID NO: 10<br>*C. maxima*<br>CLAPR1 protein sequence | MGTFQSFRKAYGALKDSTKVGLAKVNSEFKDLDIAIVKATNHVE<br>CPPKERHVRKIFTATSVVRPRADVAYCIHALAKRLSKTRNWIVAL<br>KTLIVVHRTLREGDPTFREELLNYSQKGQVLQISNFKDDSSPLAW<br>DCSAWVRTYALFLEERLECYRVLKYDIESERLTKTSPGSTKVHSR<br>TRLLNSDELLDQLPALQQVLYRLMGCQPEGAAYSNYLIQYALAL<br>VLKESFKIYCAINDGIINLVDMFFGMPRHDAVKALNIYKRASHQA<br>ENLADFYEYCKGLELARTFQFPILKQPPPSFLATMEEYIREAPQTA<br>SVNKRLEYRVAEEMTEKPEEPEEPAEIEKEVENVDNKPLEETEEE<br>PQQKEESVPEPPPLIATEDTSDFLGLKEINPRIAEIEHNNALALAIV<br>SNGNDPSSANPALSDFGGSGWELSLVTTPTNNAGSTVGSKLAGG<br>FDKLLLDSLYEDEHARRNIQLQNAGYGTYGEMYVQNPFQQQND<br>PFAMSSSIAPPSNVQLAMMAQQQQMLYQQQQQQQHQALQTNA<br>FPQQQQLHLDESMMMVPHQQQLPQSKYPQQQQIQQQQRQQMQ<br>QFGQSNPFGDPFVPFPQNSVPPGGNHNLI |
| SEQ ID NO: 11<br>CDS of *C. lanatus*<br>CLAPR1 gene | ATGGGCACATTTCAGAGCTTCCGCAAAGCTTATGGCGCTCTCA<br>AAGACTCCACCAAGGTCGGCCTCGCTAAGGTCAACAGCGAAT<br>TCAAGGATTTGGATATCGCCATTGTCAAGGCTACCAATCATGT<br>TGAATGTCCGCCTAAAGAACGTCATGTTCGAAAAATATTTTCG<br>GCCACGTCTGTGGTGAGGCCTAGGGCGGATGTGGCGTATTGT<br>ATTCATGCATTGGCGAAGAGATTGTCGAAGACGCGGAATTGG<br>ATCGTTGCCTTGAAGACGTTGATAGTTGTACATAGGACATTGA<br>GAGAGGGTGATCCAACCTTCAGGGAAGAACTTCTCAATTATTC<br>ACACAGAGGACATATTCTCCAAATATCAAATTTTAAGGATGAT<br>TCAAGTCCTCTTGCTTGGGATTGTTCTGCATGGGTAAGGACAT<br>ATGCCCTTTTTCTAGAAGAGAGACTTGAATGTTACAGAATCTT<br>GAAGTATGACATTGAATCGGAACGCCTAACCAAAACATCACC<br>AGGATCGACGAAGGTACATAGTAGGACACGGTTGCTGAACTG<br>TGATGAGCTACTGGAGCAGCTACCCGCATTGCAGCAGCTTCTC<br>TACCGCCTTATGGGATGTCAGCCAGAAGGAGGAGCTTACAGC<br>AATTTATCTCATCCAGTATGCACTGGCTCTGGTACTCAAAGAGA<br>GCTTTAAAATATATTGTGCGATAAATGATGGAATAATAAATCT<br>TGTGGACATGTTCTTTGATATGCCAAGGCACGATGCAGTTAAA<br>GCTCTCAATATATACAAAAGAGCAAGCAACCAGGCTGAAAAT<br>CTTGCGGATTTTTACGAATATTGTAAGGGATTGGAACTTGCTA<br>GAACTTTTCAGTTTCCCACATTGAAGCAGCCACCTCCATCATT<br>TCTTTCAACAATGGAAGAGTATATAAGAGAAGCACCACAGAC<br>AGGTTCTGTTAATAAGAGACTGGAATACCGAGAGGCAGAGCA<br>AACTCAAGAACCGGAAGAGCCCGAAGAACCTGGCGAAATTGA<br>AAAGGAAGTTGAAAATGTTGAGGACAACAAACCACTGGTTGA<br>AACAGAGGAAGAACCCCAACACAAGGAAGAGGAGGTCGTTG<br>AACCTCCACCTCTAATAGCAACCGACACAAGTGATCTTCTGGG<br>TCTGAATGAAATAAATCCTAAAGCTGCAGAAATAGAAAAAAG<br>CAATGCTTTAGCTCTTGCTATAATTACAGATGGGAATGATCCA<br>TCTTCGTCAAGTCGTGCTTTGGGTGAAATTGGCGGTAGTGGTT<br>GGGAGCTAGCGCTTGTTACCACACCAAGCAATAATGCTGGTC<br>CAACGGTTCGAAAGCAGACTGGCCGGTGGTTTTGACAAGCTAT<br>TGCTTGATAGCTTGTATGAAGATGAACATGCCAGAAGACATCT<br>TCAGCTGCAGAATGCTGGATATGGACCATACGGCGAAATGAT<br>GGTGCAGAATCCATTCGAACAGCACGACCCGTTTTCAATGTCG<br>AGCAACATAGCGCCTCCCCAAACGTGCAAATGGCAATGATG<br>GCTCAACAACATCAAATGCTTTTCCAACACCAGCAACAACAA |

TABLE 1-continued

Sequence Information

| | |
|---|---|
| | CCATTACAAAGCAACGCCTTCCCTCAGCAACAACAGCAACAG<br>CAGCAATTACATTCAAATGACTCCATGATGATGGTACCTTATC<br>AACAACAATTGCCACAGTACCCTCAACAACAAATGCAACAAC<br>TTGGTCCTTCTAATCCATTTGGTGACCCGTTTCTTTCCTTTCCT<br>CAAACTTCAGTACCCCCAGGAGGAAATCATAATCTAATCTAG |
| SEQ ID NO: 12<br>C. lanatus<br>CLAPR1 protein sequence | MGTFQSFRKAYGALKDSTKVGLAKVNSEFKDLDIAIVKATNHVE<br>CPPKERHVRKIFSATSVVRPRADVAYCIHALAKRLSKTRNWIVAL<br>KTLIVVHRTLREGDPTFREELLNYSHRGHILQISNFKDDSSPLAW<br>DCSAWVRTYALFLEERLECYRILKYDIESERLTKTSPGSTKVHSR<br>TRLLNCDELLEQLPALQQLLYRLMGCQPEGGAYSNYLIQYALAL<br>VLKESFKIYCAINDGIINLVDMFFDMPRHDAVKALNIYKRASNQA<br>ENLADFYEYCKGLELARTFQFPTLKQPPPSFLSTMEEYIREAPQTG<br>SVNKRLEYREAEQTQEPEKPEEPGEIEKEVENVEDNKPLVETEEE<br>PQHKEEEVVEPPPLIATDTSDLLGLNEINPKAAEIEKSNALALAIIT<br>DGNDPSSSSRALGEIGGSGWELALVTTPSNNAGPTVESRLAGGFD<br>KLLLDSLYEDEHARRHLQLQNAGYGPYGEMMVQNPFEQHDPFS<br>MSSNIAPPPNVQMAMMAQQHQMLFQHQQQQPLQSNAFPQQQQ<br>QQQQLHSNDSMMMVPYQQQLPQYPQQQMQQLGPSNPFGDPFLS<br>FPQTSVPPGGNHNLI |
| SEQ ID NO: 13<br>Forward primer for<br>amplifying C. melo<br>CLAPR1 gene with<br>c.1599_1600insCAGCAACAA | TTCCAACACCAACAACAAC |
| SEQ ID NO: 14<br>Reverse primer for<br>amplifying C. melo<br>CLAPR1 gene with<br>c.1599_1600insCAGCAACAA | AGGAAAGGAAAGAAAAGGG |

CDS = Coding DNA Sequence

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

CYSDV Disease Testing in *Cucumis melo* Plants

Seeds from *Cucumis melo* plants were sown alongside CYSDV susceptible controls in trays. Approximately 8 days after sowing, when the seedlings were at the cotyledon stage, CYSDV was introduced by massive inoculation with viruliferous whiteflies (*Bemisia tabaci*). Inoculation with the CYSDV infected whiteflies was allowed to continue for 3 days to ensure that adequate virus inoculation took place.

Following inoculation, plants were sprayed to remove the whiteflies, transplanted into pots (5 pots per line) and transferred to a greenhouse to grow under controlled conditions (e.g. 12 hour photoperiod; day/night temperature at 28° C.).

Plants were visually assessed at approximately 18 days after sowing. Each plant was scored for the amount of CYSDV symptoms, based on the scale explained in Table 2. A second visual assessment of the plants was performed approximately 1 week later, to confirm the presence/absence of symptoms. Plants were scored as resistant, intermediate resistant, or susceptible based on CYSDV symptoms which included yellowing spots, interveinal chlorosis, mottling of the leaves or leaf curling. Plants exhibiting no or slight viral symptoms and appeared to be healthy, were considered as being resistant in this disease test. Quantitative PCR (qPCR) may be used to further confirm a low/absent viral load in CYSDV inoculated plants not exhibiting viral symptoms (e.g. resistance). The skilled person is familiar with designing a qPCR assay that is specific for detecting and quantifying CYSDV. Results of the CYSDV disease testing are shown in Table 3 (see "Phenotype").

TABLE 2

CYSDV Plant Disease Test for *Cucumis melo*

| Disease Score | CYSDV symptoms on melon plants | Resistance/Susceptibility to CYSDV |
|---|---|---|
| 0 | No or slight virus symptoms: subtle localized yellow spotting in one part of the leaves; otherwise healthy plant | Resistant |
| 1 | Mild virus symptoms on the leaves: interveinal mottling of the leaves; veins remain relatively green | Intermediate resistant |
| 2 | Severe virus symptoms on one or more leaves; yellow interveinal chlorosis; veins remaining relatively green; leaf curling; fragile leaves | Susceptible |

Example 2

Sequencing of the CLAPR1 Gene

QTL mapping studies followed by several rounds of fine mapping were performed on a mapping population derived from a CYSDV resistant melon plant of the invention and a CYSDV susceptible melon plant, in order to identify gene(s)

responsible for the trait of the invention, namely CYSDV resistance. In this study, a gene designated CLAPR1 gene was identified. The CLAPR1 gene of *Cucumis melo* plants of the invention found to be resistant to CYSDV in the CYSDV disease test of Example 1, of which a representative sample of seed was deposited with the NCIMB under NCIMB 42992, was sequenced alongside the wild type CLAPR1 gene from a *Cucumis melo* plant susceptible to CYSDV. The CDS of the wild type CLAPR1 gene is given in SEQ ID. No. 1 and the protein sequence of the encoded wild type protein sequence is given in SEQ ID NO: 2.

Sequencing revealed a modified CLAPR1 gene in the resistant *Cucumis melo* plant of the invention, comprising a nine base pair insertion starting at position c.1599_1600insCAGCAACAA in SEQ ID. No. 1 (the sequence of the modified CLAPR1 gene including the CAGCAACAA insertion is shown in SEQ ID NO: 3) encoding a modified protein comprising a 3 glutamine (Q) insertion at position p.533_534insQQQ in SEQ ID. No. 2 (the sequence of the modified CLAPR1 protein including the QQQ insertion is shown in SEQ ID NO: 4). The 3Q insertion occurs in a polyQ tract of the encoded protein, causing its expansion. CYSDV resistant plants of the invention all comprise the nine base pair insertion c.1599_1600insCAGCAACAA in the CLAPR1 gene (See "CLAPR1 Gene Sequence", Table 3).

TABLE 3

Results of CYSDV Disease Test and CLAPR1 Gene Sequencing

| Line number | CLAPR1 Gene Sequence | Phenotype |
|---|---|---|
| CYSDV Susceptible Control | T | S |
| 102474-02 | TCAGCAACAA | R |
| 102474-04 | TCAGCAACAA | R |
| 102474-08 | TCAGCAACAA | R |
| 102474-09 | TCAGCAACAA | R |
| 102474-13 | TCAGCAACAA | R |
| 102474-15 | T | S |
| 102474-19 | T | S |
| 102474-20 | TCAGCAACAA | R |
| 102474-21 | T | S |
| 102474-22 | T | S |
| 102474-23 | T | S |
| 102474-50 | T | S |
| 102474-51 | T | S |
| 102474-52 | T | S |
| 102474-53 | T | S |
| 102474-54 | T | S |
| 102474-55 | T | S |
| 102474-56 | T | S |
| 102474-57 | T | S |
| 102474-59 | T | S |
| 102474-60 | TCAGCAACAA | R |
| 102474-61 | T | S |
| 102474-62 | TCAGCAACAA | R |
| 102474-63 | TCAGCAACAA | R |
| 102474-64 | T | S |
| 102474-65 | TCAGCAACAA | R |
| 102474-66 | TCAGCAACAA | R |
| 102474-67 | T | S |
| 102474-70 | T | S |
| 102474-71 | T | S |
| 102474-72 | T | S |
| 102474-97 | T | S |
| 102474-98 | T | S |
| 102474-99 | T | S |
| 102474-100 | T | S |
| 102474-101 | T | S |
| 102474-102 | T | S |
| 102474-103 | T | S |
| 102474-104 | T | S |
| 102474-106 | T | S |
| 102474-108 | T | S |
| 102474-109 | TCAGCAACAA | R |
| 102474-110 | T | S |
| 102474-111 | T | S |
| 102474-112 | T | S |
| 102474-113 | T | S |
| 102474-114 | T | S |
| 102474-115 | T | S |

Wild type CLAPR1 gene sequence = T;
Modified CLAPR1 gene sequence = TCAGCAACAA;
S = Susceptible to CYSDV;
R = Resistant to CYSDV Example 3

Introducing the Modified CLAPR1 Gene into a Melon Plant not Comprising the Modified Gene A melon plant comprising the modified CLAPR1 gene homozygously, of which a representative sample of seed was deposited with the NCIMB under accession number 42992, was crossed with a plant of variety Vedrantais which is susceptible to CYSDV and does not comprise the modified CLAPR1 gene, to obtain an F1 generation. Subsequently, an F1 plant was selfed to obtain an F2 population.

Plants of the F2 population were assayed as described in Example 1 for resistance against CYSDV. Approximately 25% of the plants scored completely resistant in the assay, while the remaining plants of the F2 population were susceptible to CYSDV.

Genomic DNA of each plant of the F2 population was isolated and used in a polymerase chain reaction (PCR), using the forward primer TTCCAACACCAACAACAAC (SEQ ID NO: 13) and reverse primer AGGAAAGGAAAGAAAAGGG (SEQ ID NO: 14). The PCR primers were designed based on the sequence information of the CLAPR1 gene obtained from Example 2. The PCR assay could be used to discern between an amplified fragment that comprises the nine base pair insertion (i.e. the modified CLAPR1 gene) or an amplified fragment of the CLAPR1 gene that does not comprise the nine base pair insertion (i.e. the wild type CLAPR1 gene).

PCR conditions for selectively amplifying a region of the CLAPR1 gene using primers having SEQ ID NO: 13 and SEQ ID NO: 14 were as follows, using Platinum Taq enzyme (Thermo Fisher Scientific):

5 minutes at 95° C. (initial denaturation);
35 amplification cycles, each cycle consisting of: 30 seconds denaturation at 94° C., 30 seconds of annealing at 55° C., and 30 seconds extension at 72° C.;
1 minute at 72° C. (final extension)

The PCR products were visualized on an agarose gel (not shown). A PCR product not comprising the 9 bp insertion is approximately 180 bp in length while a PCR product comprising the 9 bp insertion is approximately 189 bp in length. Results indicated that approximately 25% of the samples comprised a fragment of approximately 189 bp, and these samples correlated with the plants that scored as resistant against CYSDV.

Subsequent purification and sequencing of the PCR products confirmed the presence of the 9 bp insertion (CAGCAACAA) in the modified CLAPR1 gene of the CYSDV resistant melon plants of the invention.

Example 4

Identification of CLAPR1 Orthologs

Since CYSDV infection is primarily a problem for members of the Cucurbitaceae family, we focused on identifying the orthologous CLAPR1 gene in these species. Orthologs of the CLAPR1 gene were identified using a Basic Local Alignment Search Tool (BLAST) to compare the *Cucumis melo* CLAPR1 DNA and protein sequences with the genome of other Cucurbitaceae species. Using this method, 1-2 best hits per species were identified as candidate CLAPR1 orthologous genes. DNA and protein sequences of the CLAPR1 orthologs that were identified through this method are shown in Table 1, SEQ ID NOS: 5-12. Multiple sequence alignments (MSA) of the predicted protein sequences confirmed that these were orthologous CLAPR1 genes (FIG. 1). Furthermore, the wild type CLAPR1 protein of *Cucumis sativus* (cucumber), *Momordica charantia* (bitter melon), *Cucurbita maxima* (squash), and *Citrullus lanatus* (watermelon) has a high sequence identity and sequence similarity to the wild type CLAPR1 protein of *Cucumis melo* (melon) (FIG. 7).

Functional analysis of the orthologous CLAPR1 protein sequences was performed using InterProScan (Jones et al. (2014) *Bioinformatics*, 30(9): 1236-1240) in order to predict information about the protein's function, an overview of the families that the protein belongs to, and the domains that it contains. All CLAPR1 orthologs comprise an ENTH/VHS domain (IPR008942), Phosphoinositide-binding clathrin adaptor domain 2 (IPR014712), ENTH domain (IPR013809) and an AP180 N-terminal homology (ANTH) domain (IPR013809) (FIGS. 2-6). Based on these highly conserved signature domains, CLAPR1 is predicted to have a role in clathrin coat assembly (Gene Ontology Accession: GO:0048268).

Example 5

Modifying the CLAPR1 Gene to Produce the CYSDV Resistance Trait

Seeds of the plant species of interest are mutagenized in order to introduce point mutations into the genome. Mutagenesis is achieved using chemical means, such as EMS treatment, or specific targeted means such as CRISPR. The skilled person is familiar with both chemical and targeted means for introducing mutations into a genome.

Mutagenized seed is then germinated, the resultant plants are selfed or crossed to produce M2 seed. A tilling screen for CLAPR1 gene modifications which are responsible for CYSDV resistance is performed. CLAPR1 gene modifications are identified based on comparison to the wild type CLAPR1 DNA sequences listed in SEQ ID's 1, 5, 7, 9 and 11 for the given plant species. The skilled person is also familiar with tilling (McCallum et. al. (2000) *Nature Biotechnology*, 18: 455-457) and techniques for identifying nucleotide changes such as DNA sequencing amongst others.

Plants with a modified CLAPR1 gene are homozygous or made homozygous by selfing, crossing or doubled haploid techniques which are familiar to the skilled person. Plants identified and selected on the basis of modifications to the CLAPR1 gene, especially modifications that effect the polyQ tract of the encoded protein as defined in Example 2 and/or the conserved domains of the CLAPR1 gene as defined in Example 4, can then be tested in a CYSDV disease test to confirm that the CYSDV resistance results from one or more modifications of the CLAPR1 gene.

The invention is further described by the following numbered paragraphs:

1. A modified CLAPR1 gene, wherein the modified CLAPR1 gene encodes a modified protein comprising one or more modifications in the wild type protein sequence of SEQ ID NO: 2 or in a protein sequence having at least 86% sequence identity to SEQ ID NO: 2, preferably 87%, 88%, 89%, 90%, 91%, 92%, 93%, 94%, 95%, 96%, 97%, 98%, or 99% sequence identity.

2. The modified CLAPR1 gene of paragraph 1, wherein the one or more modifications is selected from an amino acid substitution, a premature stop codon, or an insertion or deletion of one or more amino acids.

3. The modified CLAPR1 gene of paragraph 1 or 2, wherein the modified CLAPR1gene encodes a modified protein that comprises an insertion of at least one glutamine at position p. 533_534insQ of SEQ ID NO: 2.

4. The modified CLAPR1 gene of any one of the paragraphs 1-3, wherein the modified gene encodes a modified protein that comprises three glutamine insertions at position p.533_534insQQQ in SEQ ID. No. 2.

5. The modified CLAPR1 gene of any one of the paragraphs 1-4, wherein the modified gene encodes a modified protein that comprises one or more amino acid changes or a premature stop codon in its ENTH/VHS domain, ENTH domain, ANTH domain or Phosphoinositide binding clathrin adaptor domain 2.

6. The modified CLAPR1 gene of any one of the paragraphs 1-5, wherein the modified protein as a result of the one or more modifications, provides resistance to CYSDV when present in a plant.

7. A modified CLAPR1 protein as defined in any one of the paragraphs 1-5.

8. The modified CLAPR1 protein of paragraph 7, wherein the modified protein as a result of the one or more modifications provides resistance to CYSDV when present in a plant.

9. A *Cucumis melo* plant, comprising the modified CLAPR1 gene of any one of the paragraphs 1-6.

10. The *Cucumis melo* plant of paragraph 9, which plant is resistant to CYSDV as a result of the presence of the modified protein.

11. A *Cucumis melo* seed comprising the modified CLAPR1 gene of in any one of the paragraphs 1-6, wherein the plant grown from the seed is resistant to CYSDV as a result of the presence of the modified protein.

12. A progeny plant of the plant of paragraph 9 or 10, or of a plant grown from the seed of paragraph 11, comprising the modified CLAPR1 gene of any one of the paragraphs 1-6, which progeny plant is resistant to CYSDV as a result of the presence of the modified protein.

13. A fruit harvested from the plant of paragraph 9, 10 or 12, or from a plant grown from the seed of paragraph 11, wherein the fruit comprises the modified CLAPR1 gene of any one of the paragraphs 1-6.

14. Propagation material suitable for producing the plant of paragraph 9 or 10, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material comprises the modified CLAPR1 gene of any one of the paragraphs 1-6 that confers resistance to CYSDV.

15. The modified CLAPR1 gene of paragraph 1 or 2, wherein the modified gene encodes a modified protein that comprises an insertion of at least one glutamine at position p. 534_535insQ in SEQ ID NO: 6.

16. The modified CLAPR1 gene of paragraph 15, wherein the modified gene encodes a modified protein that comprises one or more amino acid changes or a premature stop codon in its ENTH/VHS domain, ENTH domain, ANTH domain or Phosphoinositide binding clathrin adaptor domain 2.

17. The modified CLAPR1 gene of paragraph 15 or 16, wherein the modified protein as a result of the one or more modifications, provides resistance to CYSDV when present in a *Cucumis sativus* plant.

18. A modified CLAPR1 protein as defined in any one of the paragraphs 15-17.

19. The modified CLAPR1 protein of paragraph 18, wherein the modified protein provides resistance to CYSDV when present in a *Cucumis sativus* plant.

20. A *Cucumis sativus* plant comprising the modified CLAPR1 gene of any one of the paragraphs 15-17, which plant is resistant to CYSDV as a result of the presence of the modified protein.

21. A *Cucumis sativus* seed comprising the modified CLAPR1 gene of in any one of the paragraphs 15-17, wherein the plant grown from the seed is resistant to CYSDV as a result of the presence of the modified protein.

22. A progeny plant of the plant of paragraph 20 or of a plant grown from the seed of paragraph 21, comprising the modified CLAPR1 gene of any one of the paragraphs 15-17, which progeny plant is resistant to CYSDV as a result of the presence of the modified protein.

23. A fruit harvested from the plant of paragraph 20 or 22, or from a plant grown from the seed of paragraph 21, wherein the fruit comprises the modified CLAPR1 gene of any one of the paragraphs 15-17.

24. Propagation material suitable for producing the plant of paragraph 20, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material comprises the modified CLAPR1 gene of any one of the paragraphs 15-17 that confers resistance to CYSDV.

25. The modified CLAPR1 gene of paragraph 1 or 2, wherein the modified gene encodes a modified protein that comprises an insertion of at least one glutamine at position p. 536_537insQ in SEQ ID NO: 8.

26. The modified CLAPR1 gene of paragraph 25, wherein the modified gene encodes a modified protein that comprises one or more amino acid changes or a premature stop codon in its ENTH domain, ANTH domain or Phosphoinositide binding clathrin adaptor domain 2.

27. The modified CLAPR1 gene of paragraph 25 or 26, wherein the modified protein as a result of the one or more modifications, provides resistance to CYSDV when present in a *Momordica charantia* plant.

28. A modified CLAPR1 protein as defined in any one of the paragraphs 25-27.

29. The modified CLAPR1 protein of paragraph 28, wherein the modified protein provides resistance to CYSDV when present in a *Momordica charantia* plant.

30. A *Momordica charantia* plant comprising the modified CLAPR1 gene of any one of the paragraphs 25-27, which plant is resistant to CYSDV as a result of the presence of the modified protein.

31. A *Momordica charantia* seed comprising the modified CLAPR1 gene of in any one of the paragraphs 25-27, wherein the plant grown from the seed is resistant to CYSDV as a result of the presence of the modified protein.

32. A progeny plant of the plant of paragraph 30 or of a plant grown from the seed of paragraph 31, comprising the modified CLAPR1 gene of any one of the paragraphs 25-27, which progeny plant is resistant to CYSDV as a result of the presence of the modified protein.

33. A fruit harvested from the plant of paragraph 30 or 32, or from a plant grown from the seed of paragraph 31, wherein the fruit comprises the modified CLAPR1 gene of any one of the paragraphs 25-27.

34. Propagation material suitable for producing the plant of paragraph 30, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material comprises the modified CLAPR1 gene of any one of the paragraphs 25-27 that confers resistance to CYSDV.

35. The modified CLAPR1 gene of paragraph 1 or 2, wherein the modified gene encodes a modified protein that comprises an insertion of at least one glutamine at position p. 537_538insQ in SEQ ID NO: 10.

36. The modified CLAPR1 gene of paragraph 35, wherein the modified gene encodes a modified protein that comprises one or more amino acid changes or a premature stop codon in its ENTH domain, ANTH domain or Phosphoinositide binding clathrin adaptor domain 2.

37. The modified CLAPR1 gene of paragraph 35 or 36, wherein the modified protein as a result of the one or more modifications, provides resistance to CYSDV when present in a *Cucurbita maxima* plant.

38. A modified CLAPR1 protein as defined in any one of the paragraphs 35-37.

39. The modified CLAPR1 protein of paragraph 38, wherein the modified protein provides resistance to CYSDV when present in a *Cucurbita maxima* plant.

40. A *Cucurbita maxima* plant comprising the modified CLAPR1 gene of any one of the paragraphs 35-37, which plant is resistant to CYSDV as a result of the presence of the modified protein.

41. A *Cucurbita maxima* seed comprising the modified CLAPR1 gene of in any one of the paragraphs 35-37, wherein the plant grown from the seed is resistant to CYSDV as a result of the presence of the modified protein.

42. A progeny plant of the plant of paragraph 40 or of a plant grown from the seed of paragraph 41, comprising the modified CLAPR1 gene of any one of the paragraphs 35-37, which progeny plant is resistant to CYSDV as a result of the presence of the modified protein.

43. A fruit harvested from the plant of paragraph 40 or 42, or from a plant grown from the seed of paragraph 41, wherein the fruit comprises the modified CLAPR1 gene of any one of the paragraphs 35-37.

44. Propagation material suitable for producing the plant of paragraph 40, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material comprises the modified CLAPR1 gene of any one of the paragraphs 35-37 that confers resistance to CYSDV.

45. The modified CLAPR1 gene of paragraph 1 or 2, wherein the modified gene encodes a modified protein that comprises an insertion of at least one glutamine at position p. 532_533insQ in SEQ ID NO: 12.

46. The modified CLAPR1 gene of paragraph 45, wherein the modified gene encodes a modified protein that comprises one or more amino acid changes or a premature stop codon in its ENTH domain, ANTH domain or Phosphoinositide binding clathrin adaptor domain 2.

47. The modified CLAPR1 gene of paragraph 45 or 46, wherein the modified protein as a result of the one or more modifications, provides resistance to CYSDV when present in a *Citrullus lanatus* plant.

48. A modified CLAPR1 protein as defined in any one of the paragraphs 45-47.

49. The modified CLAPR1 protein of paragraph 48, wherein the modified protein provides resistance to CYSDV when present in a *Citrullus lanatus* plant.

50. A *Citrullus lanatus* plant comprising the modified CLAPR1 gene of any one of the paragraphs 45-47, which plant is resistant to CYSDV as a result of the presence of the modified protein.

51. A *Citrullus lanatus* seed comprising the modified CLAPR1 gene of in any one of the paragraphs 45-47, wherein the plant grown from the seed is resistant to CYSDV as a result of the presence of the modified protein.

52. A progeny plant of the plant of paragraph 50 or of a plant grown from the seed of paragraph 51, comprising the modified CLAPR1 gene of any one of the paragraphs 45-47, which progeny plant is resistant to CYSDV as a result of the presence of the modified protein.

53. A fruit harvested from the plant of paragraph 50 or 52, or from a plant grown from the seed of paragraph 51, wherein the fruit comprises the modified CLAPR1 gene of any one of the paragraphs 45-47.

54. Propagation material suitable for producing the plant of paragraph 50, wherein the propagation material is suitable for sexual reproduction, and is in particular selected from a microspore, pollen, ovary, ovule, embryo sac and egg cell, or is suitable for vegetative reproduction, and is in particular selected from a cutting, root, stem cell, and protoplast, or is suitable for tissue culture of regenerable cells or protoplasts, which regenerable cells or protoplasts are in particular selected from a leaf, pollen, embryo, cotyledon, hypocotyl, meristematic cell, root, root tip, anther, flower and stem, and wherein the propagation material comprises the modified CLAPR1 gene of any one of the paragraphs 45-47 that confers resistance to CYSDV.

55. Use of a modified CLAPR1 gene of any one of the paragraphs 1-6 for producing a plant that is resistant to CYSDV, preferably a plant of the species *Cucumis melo, Cucumis sativus, Cucurbita maxima, Momordica charantia*, or *Citrullus lanatus.*

56. Use of paragraph 55, wherein the plant that is resistant to CYSDV is produced by introducing the modified CLAPR1 gene into its genome, in particular by means of mutagenesis or introgression, or combinations thereof.

57. A method for producing a plant of the Cucurbitaceae family, in particular a *Cucumis melo* plant, which plant is resistant against CYSDV, said method comprising:

(a) crossing a plant comprising a modified CLAPR1 gene with another plant to obtain an F1 population;

(b) optionally performing one or more rounds of selfing and/or crossing a plant from the F1 to obtain a further generation population;

(c) selecting from the population a plant that comprises the modified CLAPR1 gene and is resistant against CYSDV.

58. The method of paragraph 57, wherein the modified CLAPR1 gene is as defined in any one of the paragraphs 1-6.

59. The method of paragraph 58, wherein the plant comprising a modified CLAPR1 gene in step a) is a plant of paragraph 9, 10, 20, 30, 40, or 50.

60. The method of any one of the paragraphs 57-59, wherein the plant comprising a modified CLAPR1 gene in step a) is a plant grown from seed deposited under NCIMB accession number 42992.

61. A method for producing a plant of the Cucurbitaceae family having resistance against CYSDV, said method comprising:

(a) introducing one or more mutations in a population of plants;

(b) selecting a plant showing resistance to CYSDV;

(c) verifying if the plant selected in step (b) has a mutation in its CLAPR1 gene, and selecting a plant comprising such a mutation;

(d) growing the plant obtained in step (c), wherein the wild type CLAPR1 gene encodes a protein comprising at least 86% sequence identity, preferably 87%, 88%, 89%, 90%, 91%, 92%, 93%, 94%, 95%, 96%, 97%, 98%, or 99% sequence identity to SEQ ID NO: 2.

62. The method of paragraph 61, wherein the population of plants in step a) are of the species *Cucumis melo, Cucumis sativus, Cucurbita maxima, Momordica charantia*, or *Citrullus lanatus.*

63. The method of paragraph 61 or 62, wherein the mutation in the CLAPR1 gene is an insertion of at least three nucleotides, which corresponds to an insertion of at least one glutamine at position 533_534insQ of SEQ ID NO: 2 in the encoded protein.

64. The method of any one of the paragraphs 61-63, wherein the mutation in the CLAPR1 gene is an insertion of nine nucleotides, which corresponds to an insertion of three glutamines at position 533_534insQQQ of SEQ ID NO: 2 in the encoded protein.

65. A method for identifying or selecting a plant of the Cucurbitaceae family resistant against CYSDV, said method comprising:

(a) assaying genomic nucleic acids of a plant of the Cucurbitaceae family for the presence of one or more modifications in the CLAPR1 gene;

(b) identifying or selecting a plant if one or more modifications in the CLAPR1 gene are present as a plant of the Cucurbitaceae family that is resistant to CYSDV; and (c) optionally verifying if the plant is resistant to CYSDV.

66. The method of paragraph 65, wherein the plant is a plant of the species *Cucumis melo, Cucumis sativus, Cucurbita maxima, Momordica charantia*, or *Citrullus lanatus*.

67. The method of paragraph 65 or 66, wherein the modification in the modified CLAPR1 gene is an insertion of at least three nucleotides, which corresponds to an insertion of at least one glutamine at position 533_534insQ of SEQ ID NO: 2 in the encoded protein.

68. The method of any one of the paragraphs 65-67, wherein the modification in the modified CLAPR1 gene is an insertion of nine nucleotides, which corresponds to an insertion of three glutamines at position 533_534insQQQ of SEQ ID NO: 2 in the encoded protein.

69. The method of paragraph 67 or 68 wherein the nucleotide insertion is determined by using a primer pair to amplify the insertion, wherein the forward primer is a nucleic acid molecule having the sequence of SEQ ID NO: 13.

70. The method of paragraph 67 or 68, wherein the insertion is determined by using a primer pair to amplify the insertion, wherein the reverse primer is a nucleic acid molecule having the sequence of SEQ ID NO: 14.

71. A primer pair comprising a forward primer which is a nucleic acid molecule having the sequence of SEQ ID NO: 13 and a reverse primer having the sequence of SEQ ID NO: 14.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Cucumis melo* plant, comprising a modified Clathrin Assembly Protein 1 (CLAPR1) gene homozygously, wherein the modified CLAPR1 gene encodes a modified protein comprising an insertion of at least one glutamine between residues corresponding to residues 533 and 534 of the wild type protein sequence of SEQ ID NO: 2, wherein the plant is resistant to Curcurbit Yellow Stunting Disorder Virus (CYSDV) as a result of the homozygous presence of the modified gene.

2. The plant as claimed in claim 1, wherein the modified gene encodes a modified protein that comprises an insertion of three glutamines between residues corresponding to residues 533 and 534 of SEQ ID NO: 2.

3. A *Cucumis melo* seed comprising the modified CLAPR1 gene as defined in claim 1, wherein the plant grown from the seed is resistant to Cucurbit Yellow Stunting Disorder Virus (CYSDV) as a result of the homozygous presence of the modified gene.

4. A progeny plant of the plant as claimed in claim 1, comprising the modified CLAPR1 gene, which progeny plant is resistant to Cucurbit Yellow Stunting Disorder Virus (CYSDV) as a result of the homozygous presence of the modified gene.

5. A fruit harvested from the plant as claimed in claim 1, or from a plant grown from the seed as claimed in claim 3, wherein the fruit comprises the modified CLAPR1 gene.

6. A propagation material capable of producing the plant as claimed in claim 1, wherein the propagation material comprises the modified CLAPR1 gene homozygously that confers resistance to Cucurbit Yellow Stunting Disorder Virus (CYSDV).

7. A method for producing a *Cucumis melo* plant having resistance against Cucurbit Yellow Stunting Disorder Virus (CYSDV), said method comprising:

(a) introducing a mutation in a population of plants;

(b) selecting a plant showing resistance to CYSDV;

(c) verifying if the plant selected in step (b) has a mutation in its Clathrin Assembly Protein 1 (CLAPR1) gene, and selecting a plant comprising such a mutation;

(d) growing the plant obtained in step (c), wherein the wild type CLAPR1 gene encodes a protein comprising SEQ ID NO: 2;

wherein the mutation in the CLAPR1 gene is an insertion of at least three nucleotides, which corresponds to an insertion of at least one glutamine between residues corresponding to residues 533 and 534 of SEQ ID NO: 2 in the encoded protein.

8. A *Cucumis melo* plant grown from the seed as claimed in claim 3, comprising the modified CLAPR1 gene, which plant is resistant to Curcurbit Yellow Stunting Disorder Virus (CYSDV) as a result of the homozygous presence of the modified gene.

9. The method as claimed in claim 7, wherein the mutation in the CLAPR1 gene is an insertion of nine nucleotides, which corresponds to an insertion of three glutamines between residues corresponding to residues 533 and 534 of SEQ ID NO: 2 in the encoded protein.

10. The propagation material of claim 6, wherein the propagation material is selected from a microspore, pollen, ovary, ovule, embryo sac, egg cell, cutting, root, stem cell, regenerable cell or protoplast.

11. The propagation material of claim 10, wherein the regenerable cell or protoplast is selected from a leaf, pollen, embryo, cotyledon, hypocotyl, meristematic cell, root, root tip, anther, flower and stem.

* * * * *